United States Patent [19]
Mattes et al.

[11] Patent Number: 5,985,622
[45] Date of Patent: Nov. 16, 1999

[54] PREPARATION OF ACARIOGENIC SUGAR SUBSTITUTES

[75] Inventors: Ralf Mattes; Kathrin Klein, both of Stuttgart; Hubert Schiweck; Markwart Kunz, both of Worms; Mohammed Munir, Kindenheim, all of Germany

[73] Assignee: Südzucker Aktiengesellschaft, Mannheim/ Ochsenfurt, Germany

[21] Appl. No.: 08/785,396

[22] Filed: Jan. 21, 1997

Related U.S. Application Data

[62] Division of application No. 08/374,155, Jan. 18, 1995.

[30] Foreign Application Priority Data

Jan. 19, 1994 [DE] Germany .......................... 44 01 451
Apr. 22, 1994 [DE] Germany .......................... 44 14 185

[51] Int. Cl.$^6$ .................. C12P 19/12; C12N 9/90
[52] U.S. Cl. ................... 435/100; 435/72; 435/233
[58] Field of Search ................. 435/100, 72, 233

[56] References Cited

U.S. PATENT DOCUMENTS

| | | | |
|---|---|---|---|
| 4,359,531 | 11/1982 | Bucke et al. | 435/97 |
| 4,390,627 | 6/1983 | Lantero, Jr. | 435/180 |
| 4,670,387 | 6/1987 | Bucke et al. | 435/97 |
| 4,788,145 | 11/1988 | Munir | 435/100 |
| 4,857,461 | 8/1989 | Egerer et al. | 435/94 |
| 5,229,276 | 7/1993 | Sugitani et al. | 435/97 |
| 5,336,617 | 8/1994 | Sugitani et al. | 435/252.1 |

OTHER PUBLICATIONS

Tsuyuki K. et al. "Isolation and Characterization of Isomaltulose–and Trehaluose–Producing Bacteria From Thailand Soil," (Jul. 2,1992), vol. 38, pp. 483–490.

Cheetam, P.S.J. et al. "The formation of isomaltulose by immobilized *Erwinia rhapontci*" Nature (Oct. 14, 1982), vol. 299, pp. 628–631.

Miyata, Y. et al. "Isolation and characterization of *Pseudomonas mesoacidophila* producing trehalulose" Bioscience, Biotechnology, and Biochemistry (Oct. 1992), vol. 56, No. 10, pp. 1680–1681.

Nagai, Y. et al., "Characterization of α–Glucosyltransferase from *Pseudomonas MesoacidophilaMX–45*"" Biosci. Biotech. Biochem,58(10):1789–1793, 1994.

Bugaenko, I.F., "Sweetening substances on the basis of sucrose," *Chemical Abstracts*, 1993–1994.

Ioroi, R., et al;, "Oligosaccharide Production by Dextransucrase of *Streptococcus bovis* No. 148 Isolated from Bovine Rumen, " *Nippon Shokuhin Kogyo Gakkaishi*, vol. 37, 5:355–362 (1990).

Itoh, Y., et al., "Synthesis of Leucrose by Dextransucrase and Some Conditions for the Reaction, " *Nippon Shokuhin Kogyo Gakkaishi*, vol. 37,3:171–177(1990).

Iizuka, M., et al., "Susceptibility of leucrose to carbohydrates," *Biological Abstracts*, Jun., 1991.

Crabb, W. D., et al., "Tools and Strategies for Cloning Studies," in Streips and Yasbin *Modern Microbial Genetics*, pp.365–388, 1991.

Brock, T.D., et al., "Kinds of Plasmids and Their Biological Significance," *Biology of Micro–Organisms*, Prentice–Hall, Inc., Chapter 8, Section 7.6–7.9, pp. 278–314, 1988.

Cheetam, P.S.J. (1984) "The extraction and mechanism of a novel isomaltulose–synthesizing enzyme from *Erwini rhapontici*," *Biochem. J.* 220:213–220.

Bockmann, J., et al., "Characterization of a chomosomaly encoded, non–PTS metabolic pathway for sucrose utilization in *Escherichia coli* EC3132," Mol Gen Genet, 235:22–32 (1992).

Joklik, W., et al., "Enterobacteriaceae: General Characteristics," *Zinsser Microbiology*, 18th Ed., pp. 595–601 (1968).

Hartmeier, W., et al., "Immobolized Biocatalysts: An Introduction," *Springer–Verlag*, pp. 139–144 (1986).

Jahreis, K. and Lengeler, J., "Molecular analysis of two ScrR repressors and of a ScrR–FruR hybrid repressor for sucrose and D–frutose specific regulons from enteric bacteria," *Molecular Microbiology*, 9(1):195–209 (1993).

Sprenger, G., and Lengeler, J., "Analysis of Sucrose Catabolism in *Klebsiella pneumoniae* and in Scr+ Derivatives of *Escherichia coli* K 12, "J. Gen. Micorbiology, 134:1635–1644(1998).

Ernst–L. Winnacker, "From Genes to Clones: Introduction to Gene Technology," Weinheim (Federal Republic of Germany): VCH Vertagsgesellschaft (1987) pp. 383–395.

*Primary Examiner*—Kawai Lau
*Attorney, Agent, or Firm*—Finnegan, Henderson, Farabow, Garrett & Dunner, L.L.P.

[57] ABSTRACT

The invention relates to sucrose isomerases, to DNA sequences coding therefor, and to novel processes for the production of non-cariogenic sugars.

5 Claims, No Drawings

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 1890 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ATGCCCCGTC AAGGATTGAA AACTGCACTA GCGATTTTTC TAACCACATC ATTATGCATC      6060

TCATGCCAGC AAGCCTTCGG TACGCAACAA CCCTTGCTTA ACGAAAAGAG TATCGAACAG     12120

TCGAAAACCA TACCTAAATG GTGGAAGGAG GCTGTTTTTT ATCAGGTGTA TCCGCGCTCC     18180

TTTAAAGACA CCAACGGAGA TGGCATCGGG GATATTAACG GCATCATAGA AAAATTAGAC     24240

TATCTAAAAG CCTTGGGGAT TGATGCCATT TGGATCAACC CACATTATGA TTCTCCGAAC     30300

ACGGATAATG GTTACGATAT ACGTGATTAT CGAAAAATCA TGAAAGAATA TGGCACGATG     36360

GAGGATTTTG ACCGCCTGAT TTCTGAAATG AAAAAACGGA ATATGCGGTT GATGATTGAT     42420

GTGGTCATCA ACCACACCAG CGATCAAAAC GAATGGTTTG TTAAAAGTAA AGCAGTAAG      48480

GATAATCCTT ATCGCGGCTA TTATTTCTGG AAAGATGCTA AGAAGGGCA GGCGCCTAAT      54540

AATTACCCTT CATTCTTTGG TGGCTCGGCG TGGCAAAAAG ATGAAAAGAC CAATCAATAC     60600
```

```
TACCTGCACT ATTTTGCTAA CAACAGCCT GACCTAAACT GGGATAATCC CAAAGTCCGT    66660

CAAGATCTTT ATGCAATGTT ACGTTTCTGG TTAGATAAAG GCGTGTCTGG TTTACGTTTT    72720

GATACGGTAG CGACCTACTC AAAAATTCCG GATTTCCCAA ATCTCACCCA ACAACAGCTG    78780

AAGAATTTTG CAGCGGAGTA TACCAAGGGC CCTAATATTC ATCGTTACGT CAATGAAATG    84840

AATAAAGAGG TCTTGTCTCA TTACGACATT GCGACTGCCG GTGAAATCTT TGGCGTACCC    90900

TTGGATCAAT CGATAAAGTT CTTCGATCGC CGCCGTGATG AGCTGAACAT TGCATTTACC    96960

TTTGACTTAA TCAGACTCGA TCGAGACTCT GATCAAAGAT GGCGTCGAAA AGATTGGAAA   101020

TTGTCGCAAT TCCGGCAGAT CATCGATAAC GTTGACCGTA CTGCAGGAGA ATATGGTTGG   101080

AATGCCTTCT TCTTGGATAA CCACGACAAT CCGCGCGCTG TCTCGCACTT TGGCGATGAT   111140

GATCGCCCAC AATGGCGTGA GCCATCGGCT AAAGCGCTTG CAACCTTGAC GCTGACTCAA   121200

CGAGCAACAC CTTTTATTTA TCAAGGTTCA GAATTGGGCA TGACCAATTA CCCGTTTAAA   121260

GCTATTGATG AATTCGATGA TATTGAGGTG AAAGGTTTTT GGCATGACTA CGTTGAGACA   131320

GGAAAGGTCA AAGCCGACGA GTTCTTGCAA AATGTACGCC TGACGAGCAG GGATAACAGC   131380

CGGACGCCGT TCCAATGGGA TGGGAGCAAA AATGCAGGAT TCACGAGCGG AAAACCTTGG   141440

TTCAAGGTCA ACCCAAACTA CCAGGAAATC AATGCAGTAA GTCAAGTCAC ACAACCCGAC   151500

TCAGTATTTA ACTATTATCG TCAGTTGATC AAGATAAGGC ATGACATCCC GGCACTGACC   151560

TATGGTACAT ACACCGATTT GGATCCTGCA AATGATTCGG TCTACGCCTA TACACGCAGC   161620

CTTGGGGCGG AAAAATATCT TGTTGTTGTT AACTTCAAGG AGCAAATGAT GAGATATAAA   161680

TTACCGGATA ATTTATCCAT TGAGAAAGTG ATTATAGACA GCAACAGCAA AAACGTGGTG   171740

AAAAGAATG ATTCATTACT CGAGCTAAAA CCATGGCAGT CAGGGGTTTA TAAAACTAAA   181800

TCAATAAATC TCATAGTCAC GCCAAATAAT GTAAATATAT TGAAACTATT AAAACCGGCA   181860

TTTTATGCCG GTTTTTTTAG CGCAAAATAG                                   181890

(2) INFORMATION FOR SEQ ID NO:2:

(i) SEQUENCE CHARACTERISTICS:
         (A) LENGTH: 1305 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_RNA
         (B) LOCATION: 28
         (D) OTHER INFORMATION: /note= "N = Unknown"

(ix) FEATURE:
         (A) NAME/KEY: misc_RNA
         (B) LOCATION: 85..87
         (D) OTHER INFORMATION: /note= "N = Unknown"

(xi) SEQUENCE DESCRIPTION: SEQ ID NO:2:

ATGTCCTCTC AAGGATTGAA AACGGCTNTC GCTATTTTTC TTGCAACCAC TTTTTCTGCC        60

ACATCCTATC AGGCCTGCAG TGCCNNNCCA GATACCGCCC CCTCACTCAC CGTTCAGCAA       120

TCAAATGCCC TGCCCACATG GTGGAAGCAG GCTGTTTTTT ATCAGGTATA TCCACGCTCA       180

TTTAAAGATA CGAATGGGGA TGGCATTGGG GATTTAAACG GTATTATTGA GAATTTAGAC       240

TATCTGAAGA AACTGGGTAT TGATGCGATT TGGATCAATC CACATTACGA TTCGCCGAAT       300

ACGGATAATG GTTATGACAT CCGGGATTAC CGTAAGATAA TGAAAGAATA CGGTACGATG       360
```

```
GAAGACTTTG ACCGTCTTAT TTCAGAAATG AAGAAACGCA ATATGCGTTT GATGATTGAT      420

ATTGTTATCA ACCACACCAG CGATCAGCAT GCCTGGTTTG TTCAGAGCAA ATCGGGTAAG      480

AACAACCCCT ACAGGGACTA TTACTTCTGG CGTGACGGTA AGGATGGCCA TGCCCCCAAT      540

AACTATCCCT CCTTCTTCGG TGGCTCAGCC TGGGAAAAAG ACGATAAATC AGGCCAGTAT      600

TACCTCCATT ACTTTGCCAA ACAGCAACCC GACCTCAACT GGGACAATCC CAAAGTCCGT      660

CAAGACCTGT ATGACATGCT CCGCTTCTGG TTAGATAAAG GCGTTTCTGG TTTACGCTTT      720

GATACCGTTG CCACCTACTC GAAAATCCCG AACTTCCCTG ACCTTAGCCA ACAGCAGTTA      780

AAAAATTTCG CCGAGGAATA TACTAAAGGT CCTAAAATTC ACGACTACGT GAATGAAATG      840

AACAGAGAAG TATTATCCCA CTATGATATC GCCACTGCGG GGGAAATATT TGGGGTTCCT      900

CTGGATAAAT CGATTAAGTT TTTCGATCGC CGTAGAAATG AATTAAATAT AGCGTTTACG      960

TTTGATCTGA TCAGGCTCGA TCGTGATGCT GATGAAAGAT GGCGGCGAAA AGACTGGACC     1020

CTTTCGCAGT TCCGAAAAAT TGTCGATAAG GTTGACCAAA CGGCAGGAGA GTATGGGTGG     1080

AATGCCTTTT TCTTAGACAA TCACGACAAT CCCCGCGCGG TTTCTCACTT TGGTGATGAT     1140

CGACCACAAT GGCGCGAGCA TGCGGCGAAA GCACTGGCAA CATTGACGCT GACCCAGCGT     1200

GCAACGCCGT TTATCTATCA GGGTTCAGAA CTCGGTATGA CCAATTATCC CTTTAAAAAA     1260

ATCGATGATT TCGATGATGT AGAGGTGAAA GGTTTTTGGC AAGAC                    1305

(2) INFORMATION FOR SEQ ID NO:3:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GTTTTTTATC AGATCTATCC TCGCTCATTT AAAGACACCA ATGATGATGG CATTGGCGAT       60

ATTCGCGGTA TTATTGAAAA GCTGGACTAT CTGAAATCGC TCGGTATTGA CGCTATCTGG      120

ATCAATCCCC ATTACGACTC TCCGAACACC GATAACGGCT ATGACATCAG TAATTATCGT      180

CAGATAATGA AAGAGTATGG CACAATGGAG GATTTTGATA GCCTTGTTGC CGAAATGAAA      240

AAACGAAATA TGCGCTTAAT GATCGACGTG GTCATTAACC ATACCAGTGA TCAACACCCG      300

TGGTTTATTC AGAGTAAAAG CGATAAAAAC AACCCTTATC GTGACTATTA TTTCTGGCGT      360

GACGGAAAAG ATAATCAGCC ACCTAATAAT TACCCCTCAT TTTTCGGCGG CTCGGCATGG      420

CAAAAAGATG CAAAGTCAGG ACAGTACTAT TTACACTATT TTGCCAGACA G               471

(2) INFORMATION FOR SEQ ID NO:4:

(i) SEQUENCE CHARACTERISTICS:
        (A) LENGTH: 629 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Met Pro Arg Gln Gly Leu Lys Thr Ala Leu Ala Ile Phe Leu Thr Thr
1               5                  10                  15

Ser Leu Cys Ile Ser Cys Gln Gln Ala Phe Gly Thr Gln Gln Pro Leu
            20                  25                  30
```

-continued

```
Leu Asn Glu Lys Ser Ile Glu Gln Ser Lys Thr Ile Pro Lys Trp Trp
         35                  40                  45
Lys Glu Ala Val Phe Tyr Gln Val Tyr Pro Arg Ser Phe Lys Asp Thr
 50                  55                  60
Asn Gly Asp Gly Ile Gly Asp Ile Asn Gly Ile Ile Glu Lys Leu Asp
 65                  70                  75                  80
Tyr Leu Lys Ala Leu Gly Ile Asp Ala Ile Trp Ile Asn Pro His Tyr
                     85                  90                  95
Asp Ser Pro Asn Thr Asp Asn Gly Tyr Asp Ile Arg Asp Tyr Arg Lys
                    100                 105                 110
Ile Met Lys Glu Tyr Gly Thr Met Glu Asp Phe Asp Arg Leu Ile Ser
                115                 120                 125
Glu Met Lys Lys Arg Asn Met Arg Leu Met Ile Asp Val Val Ile Asn
130                 135                 140
His Thr Ser Asp Gln Asn Glu Trp Phe Val Lys Ser Lys Ser Ser Lys
145                 150                 155                 160
Asp Asn Pro Tyr Arg Gly Tyr Tyr Phe Trp Lys Asp Ala Lys Glu Gly
                165                 170                 175
Gln Ala Pro Asn Asn Tyr Pro Ser Phe Gly Gly Ser Ala Trp Gln
                180                 185                 190
Lys Asp Glu Lys Thr Asn Gln Tyr Tyr Leu His Tyr Phe Ala Lys Gln
                195                 200                 205
Gln Pro Asp Leu Asn Trp Asp Asn Pro Lys Val Arg Gln Asp Leu Tyr
210                 215                 220
Ala Met Leu Arg Phe Trp Leu Asp Lys Gly Val Ser Gly Leu Arg Phe
225                 230                 235                 240
Asp Thr Val Ala Thr Tyr Ser Lys Ile Pro Asp Phe Pro Asn Leu Thr
                245                 250                 255
Gln Gln Gln Leu Lys Asn Phe Ala Ala Glu Tyr Thr Lys Gly Pro Asn
                260                 265                 270
Ile His Arg Tyr Val Asn Glu Met Asn Lys Glu Val Leu Ser His Tyr
            275                 280                 285
Asp Ile Ala Thr Ala Gly Glu Ile Phe Gly Val Pro Leu Asp Gln Ser
        290                 295                 300
Ile Lys Phe Phe Asp Arg Arg Asp Glu Leu Asn Ile Ala Phe Thr
305                 310                 315                 320
Phe Asp Leu Ile Arg Leu Asp Arg Asp Ser Asp Gln Arg Trp Arg Arg
                325                 330                 335
Lys Asp Trp Lys Leu Ser Gln Phe Arg Gln Ile Ile Asp Asn Val Asp
                340                 345                 350
Arg Thr Ala Gly Glu Tyr Gly Trp Asn Ala Phe Phe Leu Asp Asn His
            355                 360                 365
Asp Asn Pro Arg Ala Val Ser His Phe Gly Asp Asp Arg Pro Gln
        370                 375                 380
Trp Arg Glu Pro Ser Ala Lys Ala Leu Ala Thr Leu Thr Leu Thr Gln
385                 390                 395                 400
Arg Ala Thr Pro Phe Ile Tyr Gln Gly Ser Glu Leu Gly Met Thr Asn
                    405                 410                 415
Tyr Pro Phe Lys Ala Ile Asp Glu Phe Asp Asp Ile Glu Val Lys Gly
                420                 425                 430
Phe Trp His Asp Tyr Val Glu Thr Gly Lys Val Lys Ala Asp Glu Phe
            435                 440                 445
Leu Gln Asn Val Arg Leu Thr Ser Arg Asp Asn Ser Arg Thr Pro Phe
        450                 455                 460
```

```
Gln Trp Asp Gly Ser Lys Asn Ala Gly Phe Thr Ser Gly Lys Pro Trp
465                 470                 475                 480

Phe Lys Val Asn Pro Asn Tyr Gln Glu Ile Asn Ala Val Ser Gln Val
                485                 490                 495

Thr Gln Pro Asp Ser Val Phe Asn Tyr Tyr Arg Gln Leu Ile Lys Ile
            500                 505                 510

Arg His Asp Ile Pro Ala Leu Thr Tyr Gly Thr Tyr Thr Asp Leu Asp
        515                 520                 525

Pro Ala Asn Asp Ser Val Tyr Ala Tyr Thr Arg Ser Leu Gly Ala Glu
    530                 535                 540

Lys Tyr Leu Val Val Asn Phe Lys Glu Gln Met Met Arg Tyr Lys
545                 550                 555                 560

Leu Pro Asp Asn Leu Ser Ile Glu Lys Val Ile Ile Asp Ser Asn Ser
                565                 570                 575

Lys Asn Val Val Lys Asn Asp Ser Leu Leu Glu Leu Lys Pro Trp
                580                 585                 590

Gln Ser Gly Val Tyr Lys Thr Lys Ser Ile Asn Leu Ile Val Thr Pro
            595                 600                 605

Asn Asn Val Asn Ile Leu Lys Leu Leu Lys Pro Ala Phe Tyr Ala Gly
    610                 615                 620

Phe Phe Ser Ala Lys
625

(2) INFORMATION FOR SEQ ID NO:5:

(i) SEQUENCE CHARACTERISTICS:
        (A) LENGTH: 435 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 10
        (D) OTHER INFORMATION: /note= "X = Unknown"

(ix) FEATURE:
        (A) NAME/KEY: Peptide
        (B) LOCATION: 29
        (D) OTHER INFORMATION: /note= "X = Unknown"

(xi) SEQUENCE DESCRIPTION: SEQ ID NO:5:

Met Ser Ser Gln Gly Leu Lys Thr Ala Xaa Ala Ile Phe Leu Ala Thr
1               5                   10                  15

Thr Phe Ser Ala Thr Ser Tyr Gln Ala Cys Ser Ala Xaa Pro Asp Thr
                20                  25                  30

Ala Pro Ser Leu Thr Val Gln Gln Ser Asn Ala Leu Pro Thr Trp Trp
            35                  40                  45

Lys Gln Ala Val Phe Tyr Gln Val Tyr Pro Arg Ser Phe Lys Asp Thr
    50                  55                  60

Asn Gly Asp Gly Ile Gly Asp Leu Asn Gly Ile Ile Glu Asn Leu Asp
65                  70                  75                  80

Tyr Leu Lys Lys Leu Gly Ile Asp Ala Ile Trp Ile Asn Pro His Tyr
                85                  90                  95

Asp Ser Pro Asn Thr Asp Asn Gly Tyr Asp Ile Arg Asp Tyr Arg Lys
            100                 105                 110

Ile Met Lys Glu Tyr Gly Thr Met Glu Asp Phe Asp Arg Leu Ile Ser
    115                 120                 125
```

```
Glu Met Lys Lys Arg Asn Met Arg Leu Met Ile Asp Ile Val Ile Asn
            130                 135                 140

His Thr Ser Asp Gln His Ala Trp Phe Val Gln Ser Lys Ser Gly Lys
145                 150                 155                 160

Asn Asn Pro Tyr Arg Asp Tyr Tyr Phe Trp Arg Asp Gly Lys Asp Gly
                165                 170                 175

His Ala Pro Asn Asn Tyr Pro Ser Phe Phe Gly Gly Ser Ala Trp Glu
                180                 185                 190

Lys Asp Asp Lys Ser Gly Gln Tyr Tyr Leu His Tyr Phe Ala Lys Gln
                195                 200                 205

Gln Pro Asp Leu Asn Trp Asp Asn Pro Lys Val Arg Gln Asp Leu Tyr
    210                 215                 220

Asp Met Leu Arg Phe Trp Leu Asp Lys Gly Val Ser Gly Leu Arg Phe
225                 230                 235                 240

Asp Thr Val Ala Thr Tyr Ser Lys Ile Pro Asn Phe Pro Asp Leu Ser
                245                 250                 255

Gln Gln Gln Leu Lys Asn Phe Ala Glu Glu Tyr Thr Lys Gly Pro Lys
                260                 265                 270

Ile His Asp Tyr Val Asn Glu Met Asn Arg Glu Val Leu Ser His Tyr
        275                 280                 285

Asp Ile Ala Thr Ala Gly Glu Ile Phe Gly Val Pro Leu Asp Lys Ser
        290                 295                 300

Ile Lys Phe Phe Asp Arg Arg Arg Asn Glu Leu Asn Ile Ala Phe Thr
305                 310                 315                 320

Phe Asp Leu Ile Arg Leu Asp Arg Asp Ala Asp Glu Arg Trp Arg Arg
                325                 330                 335

Lys Asp Trp Thr Leu Ser Gln Phe Arg Lys Ile Val Asp Lys Val Asp
                340                 345                 350

Gln Thr Ala Gly Glu Tyr Gly Trp Asn Ala Phe Phe Leu Asp Asn His
            355                 360                 365

Asp Asn Pro Arg Ala Val Ser His Phe Gly Asp Asp Arg Pro Gln Trp
    370                 375                 380

Arg Glu His Ala Ala Lys Ala Leu Ala Thr Leu Thr Leu Thr Gln Arg
385                 390                 395                 400

Ala Thr Pro Phe Ile Tyr Gln Gly Ser Glu Leu Gly Met Thr Asn Tyr
                405                 410                 415

Pro Phe Lys Lys Ile Asp Asp Phe Asp Asp Val Glu Val Lys Gly Phe
            420                 425                 430

Trp Gln Asp
        435
```

(2) INFORMATION FOR SEQ ID NO:6:

(i) SEQUENCE CHARACTERISTICS:
        (A) LENGTH: 157 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Val Phe Tyr Gln Ile Tyr Pro Arg Ser Phe Lys Asp Thr Asn Asp Asp
1               5                   10                  15

Gly Ile Gly Asp Ile Arg Gly Ile Ile Glu Lys Leu Asp Tyr Leu Lys
            20                  25                  30
```

```
Ser Leu Gly Ile Asp Ala Ile Trp Ile Asn Pro His Tyr Asp Ser Pro
         35                  40                  45

Asn Thr Asp Asn Gly Tyr Asp Ile Ser Asn Tyr Arg Gln Ile Met Lys
 50                  55                  60

Glu Tyr Gly Thr Met Glu Asp Phe Asp Ser Leu Val Ala Glu Met Lys
 65                  70                  75                  80

Lys Arg Asn Met Arg Leu Met Ile Asp Val Val Ile Asn His Thr Ser
             85                  90                  95

Asp Gln His Pro Trp Phe Ile Gln Ser Lys Ser Asp Lys Asn Asn Pro
                100                 105                 110

Tyr Arg Asp Tyr Tyr Phe Trp Arg Asp Gly Lys Asp Asn Gln Pro Pro
            115                 120                 125

Asn Asn Tyr Pro Ser Phe Phe Gly Gly Ser Ala Trp Gln Lys Asp Ala
        130                 135                 140

Lys Ser Gly Gln Tyr Tyr Leu His Tyr Phe Ala Arg Gln
145                 150                 155
```

(2) INFORMATION FOR SEQ ID NO:7:

(i) SEQUENCE CHARACTERISTICS:
        (A) LENGTH: 1362 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
ATGGCTACAA AAATCGTTTT AGTGGGCGCA GGCAGCGCGC AATTCGGCTA CGGCACCCTG     60
GGCGATATCT TCCAGAGCAA GACGCTGTAC GGCAGTGAAA TTGTGCTGCA TGACATCAAC    120
CCAACCTCGC TGGCCGTGAC CGAGAAAACC GCCCGTGACT TCCTGGCTGC GGAAGATCTG    180
CCGTTTATCG TCAGCGCCAC CACCGATCGC AAAACCGCGC TGAGCGGAGC GGAGTTCGTG    240
ATTATCTCCA TTGAAGTGGG CGACCGCTTT GCCCTGTGGG ATCTCGACTG GCAGATCCCG    300
CAACAGTATG GCATTCAGCA GGTGTATGGT GAAAACGGTG GCCCTGGCGG GCTGTTCCAC    360
TCGCTGCGCA TCATTCCACC GATCCTCGAC ATCTGCGCCG ACGTGGCGGA CATTTGCCCG    420
AACGCCTGGG TATTCAACTA CTCGAACCCG ATGAGCCGCA TTTGCACCAC CGTGCATCGC    480
CGTTTCCCGC AGCTCAACTT TGTCGGCATG TGCCATGAAA TCGCCTCACT TGAGCGTTAT    540
CTGCCAGAAA TGCTCGGCAC CTCCTTCGAC AATCTCACTC TGCGCGCTGC CGGGCTGAAC    600
CACTTCAGCG TGTTGCTGGA GGCCAGCTAT AAAGACAGCG GAAAAGACGC TTACGCCGAC    660
GTACGCGCCA AGGCACCGGA CTATTTCTCC CGTCTGCCGG CGTACAGCGA TATTCTGGCT    720
TACACCCGCA ATCACGGCAA ATTGGTGGAG ACAGAAGGCA GCACCGAACG CGATGCGCTG    780
GGCGGCAAAG ACAGCGCCTA TCCGTGGGCG GACCGCACGC TGTTCAAAGA GATCCTGGAG    840
AAGTTTCACC ATTTGCCGAT CACCGGCGAC AGCCACTTTG GCGAGTACAT CCGTTGGGCC    900
AGCGAAGTCA GCGATCACCG CGGTATCCTC GATTTCTACA CCTTCTACCG CAACTATCTG    960
GGGCATGTGC AGCCAAAAAT CGAACTGAAG CTGAAAGAAC GCGTGGTGCC GATCATGGAA   1020
GGGATCCTCA CCGATTCCGG TTATGAAGAG TCTGCGGTCA ACATTCCGAA CCAGGGATTT   1080
ATCAAGCAAC TGCCGGCGTT TATTGCCGTC GAAGTCCCGG CGATTATCGA CCGCAAGGGC   1140
GTGCACGGCA TCAAGGTCGA TATGCCTGCG GGCATCGGTG GCCTGTTGAG CAACCAGATT   1200
GCGATTCACG ATCTGACCGC CGACGCAGTG ATTGAAGGCT CGCGCGACCT GGTTATCCAG   1260
GCGCTGCTGG TGGACTCGGT CAACGATAAA TGCCGCGCGA TACCGGAACT GGTGGACGTG   1320
```

ATGATCTCAC GCCAGGGGCC GTGGCTCGAT TACCTGAAAT AA                1362

(2) INFORMATION FOR SEQ ID NO:8:

(i) SEQUENCE CHARACTERISTICS:
        (A) LENGTH: 453 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met Ala Thr Lys Ile Val Leu Val Gly Ala Gly Ser Ala Gln Phe Gly
1               5                   10                  15

Tyr Gly Thr Leu Gly Asp Ile Phe Gln Ser Lys Thr Leu Tyr Gly Ser
            20                  25                  30

Glu Ile Val Leu His Asp Ile Asn Pro Thr Ser Leu Ala Val Thr Glu
        35                  40                  45

Lys Thr Ala Arg Asp Phe Leu Ala Ala Glu Asp Leu Pro Phe Ile Val
50                  55                  60

Ser Ala Thr Thr Asp Arg Lys Thr Ala Leu Ser Gly Ala Glu Phe Val
65                  70                  75                  80

Ile Ile Ser Ile Glu Val Gly Asp Arg Phe Ala Leu Trp Asp Leu Asp
                85                  90                  95

Trp Gln Ile Pro Gln Gln Tyr Gly Ile Gln Gln Val Tyr Gly Glu Asn
            100                 105                 110

Gly Gly Pro Gly Gly Leu Phe His Ser Leu Arg Ile Ile Pro Pro Ile
        115                 120                 125

Leu Asp Ile Cys Ala Asp Val Ala Asp Ile Cys Pro Asn Ala Trp Val
130                 135                 140

Phe Asn Tyr Ser Asn Pro Met Ser Arg Ile Cys Thr Thr Val His Arg
145                 150                 155                 160

Arg Phe Pro Gln Leu Asn Phe Val Gly Met Cys His Glu Ile Ala Ser
                165                 170                 175

Leu Glu Arg Tyr Leu Pro Glu Met Leu Gly Thr Ser Phe Asp Asn Leu
            180                 185                 190

Thr Leu Arg Ala Ala Gly Leu Asn His Phe Ser Val Leu Leu Glu Ala
        195                 200                 205

Ser Tyr Lys Asp Ser Gly Lys Asp Ala Tyr Ala Asp Val Arg Ala Lys
210                 215                 220

Ala Pro Asp Tyr Phe Ser Arg Leu Pro Gly Tyr Ser Asp Ile Leu Ala
225                 230                 235                 240

Tyr Thr Arg Asn His Gly Lys Leu Val Glu Thr Glu Gly Ser Thr Glu
                245                 250                 255

Arg Asp Ala Leu Gly Gly Lys Asp Ser Ala Tyr Pro Trp Ala Asp Arg
            260                 265                 270

Thr Leu Phe Lys Glu Ile Leu Glu Lys Phe His His Leu Pro Ile Thr
        275                 280                 285

Gly Asp Ser His Phe Gly Glu Tyr Ile Arg Trp Ala Ser Glu Val Ser
290                 295                 300

Asp His Arg Gly Ile Leu Asp Phe Tyr Thr Phe Tyr Arg Asn Tyr Leu
305                 310                 315                 320

Gly His Val Gln Pro Lys Ile Gly Leu Lys Leu Lys Glu Arg Val Val
                325                 330                 335

Pro Ile Met Glu Gly Ile Leu Thr Asp Ser Gly Tyr Glu Glu Ser Ala
```

```
                340                 345                 350
Val Asn Ile Pro Asn Gln Gly Phe Ile Lys Gln Leu Pro Ala Phe Ile
        355                 360                 365
Ala Val Glu Val Pro Ala Ile Ile Asp Arg Lys Gly Val His Gly Ile
        370                 375                 380
Lys Val Asp Met Pro Ala Gly Ile Gly Gly Leu Leu Ser Asn Gln Ile
385                 390                 395                 400
Ala Ile His Asp Leu Thr Ala Asp Ala Val Ile Glu Gly Ser Arg Asp
                405                 410                 415
Leu Val Ile Gln Ala Leu Leu Val Asp Ser Val Asn Asp Lys Cys Arg
                420                 425                 430
Ala Ile Pro Glu Leu Val Asp Val Met Ile Ser Arg Gln Gly Pro Trp
                435                 440                 445
Leu Asp Tyr Leu Lys
    450
```

(2) INFORMATION FOR SEQ ID NO:9:

(i) SEQUENCE CHARACTERISTICS:
        (A) LENGTH: 1803 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
ATGCCCCGTC AAGGATTGAA AACTGCACTA GCGATTTTTC TAACCACATC ATTATGCATC    60

TCATGCCAGC AAGCCTTCGG TACGCAACAA CCCTTGCTTA ACGAAAAGAG TATCGAACAG   120

TCGAAAACCA TACCTAAATG GTGGAAGGAG GCTGTTTTTT ATCAGGTGTA CCGCGCTCC    180

TTTAAAGACA CCAACGGAGA TGGCATCGGG GATATTAACG GCATCATAGA AAAATTAGAC   240

TATCTAAAAG CCTTGGGGAT TGATGCCATT TGGATCAACC CACATTATGA TTCTCCGAAC   300

ACGGATAATG GTTACGATAT ACGTGATTAT CGAAAAATCA TGAAAGAATA TGGCACGATG   360

GAGGATTTTG ACCGCCTGAT TTCTGAAATG AAAAAACGGA ATATGCGGTT GATGATTGAT   420

GTGGTCATCA ACCACACCAG CGATCAAAAC GAATGGTTTG TTAAAAGTAA AAGCAGTAAG   480

GATAATCCTT ATCGCGGCTA TTATTTCTGG AAAGATGCTA AGAAGGGCA GGCGCCTAAT   540

AATTACCCTT CATTCTTTGG TGGCTCGGCG TGGCAAAAAG ATGAAAAGAC CAATCAATAC   600

TACCTGCACT ATTTTGCTAA CAACAGCCT GACCTAAACT GGGATAATCC CAAAGTCCGT   660

CAAGATCTTT ATGCAATGTT ACGTTTCTGG TTAGATAAAG GCGTGTCTGG TTTACGTTTT   720

GATACGGTAG CGACCTACTC AAAAATTCCG GATTTCCCAA ATCTCACCCA ACAACAGCTG   780

AAGAATTTTG CAGCGGAGTA TACCAAGGGC CCTAATATTC ATCGTTACGT CAATGAAATG   840

AATAAAGAGG TCTTGTCTCA TTACGACATT GCGACTGCCG GTGAAATCTT TGGCGTACCC   900

TTGGATCAAT CGATAAAGTT CTTCGATCGC CGCCGTGATG AGCTGAACAT TGCATTTACC   960

TTTGACTTAA TCAGACTCGA TCGAGACTCT GATCAAAGAT GGCGTCGAAA AGATTGGAAA  1020

TTGTCGCAAT TCCGGCAGAT CATCGATAAC GTTGACCGTA CTGCAGGAGA ATATGGTTGG  1080

AATGCCTTCT TCTTGGATAA CCACGACAAT CCGCGCGCTG TCTCGCACTT TGGCGATGAT  1140

CGCCCACAAT GGCGTGAGCC ATCGGCTAAA GCGCTTGCAA CCTTGACGCT GACTCAACGA  1200

GCAACACCTT TTATTTATCA AGGTTCAGAA TTGGGCATGA CCAATTACCC GTTTAAAGCT  1260

ATTGATGAAT CGATGATAT TGAGGTGAAA GGTTTTTGGC ATGACTACGT TGAGACAGGA  1320
```

```
AAGGTCAAAG CCGACGAGTT CTTGCAAAAT GTACGCCTGA CGAGCAGGGA TAACAGCCGG    1380

ACGCCGTTCC AATGGGATGG GAGCAAAAAT GCAGGATTCA CGAGCGGAAA ACCTTGGTTC    1440

AAGGTCAACC CAAACTACCA GGAAATCAAT GCAGTAAGTC AAGTCACACA ACCCGACTCA    1500

GTATTTAACT ATTATCGTCA GTTGATCAAG ATAAGGCATG ACATCCCGGC ACTGACCTAT    1560

GGTACATACA CCGATTTGGA TCCTGCAAAT GATTCGGTCT ACGCCTATAC ACGCAGCCTT    1620

GGGGCGGAAA AATATCTTGT TGTTGTTAAC TTCAAGGAGC AAATGATGAG ATATAAATTA    1680

CCGGATAATT TATCCATTGA GAAAGTGATT ATAGACAGCA ACAGCAAAAA CGTGGTGAAA    1740

AAGAATGATT CATTACTCGA GCTAAAACCA TGGCAGTCAG GGGTTTATAA ACTAAATCAA    1800

TAA                                                                 1803
```

(2) INFORMATION FOR SEQ ID NO:10:

(i) SEQUENCE CHARACTERISTICS:
        (A) LENGTH: 600 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Met Pro Arg Gln Gly Leu Lys Thr Ala Leu Ala Ile Phe Leu Thr Thr
1               5                   10                  15

Ser Leu Cys Ile Ser Cys Gln Gln Ala Phe Gly Thr Gln Gln Pro Leu
            20                  25                  30

Leu Asn Glu Lys Ser Ile Glu Gln Ser Lys Thr Ile Pro Lys Trp Trp
        35                  40                  45

Lys Glu Ala Val Phe Tyr Gln Val Tyr Pro Arg Ser Phe Lys Asp Thr
50                  55                  60

Asn Gly Asp Gly Ile Gly Asp Ile Asn Gly Ile Ile Glu Lys Leu Asp
65                  70                  75                  80

Tyr Leu Lys Ala Leu Gly Ile Asp Ala Ile Trp Ile Asn Pro His Tyr
                85                  90                  95

Asp Ser Pro Asn Thr Asp Asn Gly Tyr Asp Ile Arg Asp Tyr Arg Lys
            100                 105                 110

Ile Met Lys Glu Tyr Gly Thr Met Glu Asp Phe Asp Arg Leu Ile Ser
        115                 120                 125

Glu Met Lys Lys Arg Asn Met Arg Leu Met Ile Asp Val Val Ile Asn
    130                 135                 140

His Thr Ser Asp Gln Asn Glu Trp Phe Val Lys Ser Lys Ser Ser Lys
145                 150                 155                 160

Asp Asn Pro Tyr Arg Gly Tyr Tyr Phe Trp Lys Asp Ala Lys Glu Gly
                165                 170                 175

Gln Ala Pro Asn Asn Tyr Pro Ser Phe Phe Gly Ser Ala Trp Gln
            180                 185                 190

Lys Asp Glu Lys Thr Asn Gln Tyr Tyr Leu His Tyr Phe Ala Lys Gln
        195                 200                 205

Gln Pro Asp Leu Asn Trp Asp Asn Pro Lys Val Arg Gln Asp Leu Tyr
    210                 215                 220

Ala Met Leu Arg Phe Trp Leu Asp Lys Gly Val Ser Gly Leu Arg Phe
225                 230                 235                 240

Asp Thr Val Ala Thr Tyr Ser Lys Ser Ile Pro Asp Phe Pro Asn Leu Thr
                245                 250                 255

Gln Gln Gln Leu Lys Asn Phe Ala Ala Glu Tyr Thr Lys Gly Pro Asn
```

```
               260                 265                 270
Ile His Arg Tyr Val Asn Glu Met Asn Lys Glu Val Leu Ser His Tyr
            275                 280                 285
Asp Ile Ala Thr Ala Gly Glu Ile Phe Gly Val Pro Leu Asp Gln Ser
        290                 295                 300
Ile Lys Phe Phe Asp Arg Arg Arg Asp Glu Leu Asn Ile Ala Phe Thr
305                 310                 315                 320
Phe Asp Leu Ile Arg Leu Asp Arg Asp Ser Asp Gln Arg Trp Arg Arg
                325                 330                 335
Lys Asp Trp Lys Leu Ser Gln Phe Arg Gln Ile Ile Asp Asn Val Asp
                340                 345                 350
Arg Thr Ala Gly Glu Tyr Gly Trp Asn Ala Phe Phe Leu Asp Asn His
                355                 360                 365
Asp Asn Pro Arg Ala Val Ser His Phe Gly Asp Asp Arg Pro Gln Trp
        370                 375                 380
Arg Glu Pro Ser Ala Lys Ala Leu Ala Thr Leu Thr Leu Thr Gln Arg
385                 390                 395                 400
Ala Thr Pro Phe Ile Tyr Gln Gly Ser Glu Leu Gly Met Thr Asn Tyr
                405                 410                 415
Pro Phe Lys Ala Ile Asp Glu Phe Asp Asp Ile Glu Val Lys Gly Phe
                420                 425                 430
Trp His Asp Tyr Val Glu Thr Gly Lys Val Lys Ala Asp Glu Phe Leu
                435                 440                 445
Gln Asn Val Arg Leu Thr Ser Arg Asp Asn Ser Arg Thr Pro Phe Gln
            450                 455                 460
Trp Asp Gly Ser Lys Asn Ala Gly Phe Thr Ser Gly Lys Pro Trp Phe
465                 470                 475                 480
Lys Val Asn Pro Asn Tyr Gln Glu Ile Asn Ala Val Ser Gln Val Thr
                485                 490                 495
Gln Pro Asp Ser Val Phe Asn Tyr Tyr Arg Gln Leu Ile Lys Ile Arg
            500                 505                 510
His Asp Ile Pro Ala Leu Thr Tyr Gly Thr Tyr Thr Asp Leu Asp Pro
        515                 520                 525
Ala Asn Asp Ser Val Tyr Ala Tyr Thr Arg Ser Leu Gly Ala Glu Lys
        530                 535                 540
Tyr Leu Val Val Val Asn Phe Lys Glu Gln Met Met Arg Tyr Lys Leu
545                 550                 555                 560
Pro Asp Asn Leu Ser Ile Glu Lys Val Ile Ile Asp Ser Asn Ser Lys
                565                 570                 575
Asn Val Leu Lys Lys Asn Asp Ser Leu Leu Glu Leu Lys Pro Trp Gln
            580                 585                 590
Ser Gly Val Tyr Lys Leu Asn Gln
        595                 600

(2) INFORMATION FOR SEQ ID NO:11:

(i) SEQUENCE CHARACTERISTICS:
        (A) LENGTH: 1794 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 810
        (D) OTHER INFORMATION: /note= "D = Unknown"
```

(ix) FEATURE:
    (A) NAME/KEY: misc_RNA
    (B) LOCATION: 1471
    (D) OTHER INFORMATION: /note= "S = Unknown"

(xi) SEQUENCE DESCRIPTION: SEQ ID NO:11:

| | | | | | |
|---|---|---|---|---|---|
| ATGTCTTTTG | TTACGCTACG | TACCGGGGTG | GCTGTCGCGC | TGTCATCTTT | GATAATAAGT | 60 |
| CTGGCCTGCC | CGGCTGTCAG | TGCTGCACCA | TCCTTGAATC | AGGATATTCA | CGTTCAAAAG | 120 |
| GAAAGTGAAT | ATCCTGCATG | GTGGAAAGAA | GCTGTTTTTT | ATCAGATCTA | TCCTCGCTCA | 180 |
| TTTAAAGACA | CCAATGATGA | TGGCATTGGC | GATATTCGCG | GTATTATTGA | AAAGCTGGAC | 240 |
| TATCTGAAAT | CGCTCGGTAT | TGACGCTATC | TGGATCAATC | CCCATTACGA | CTCTCCGAAC | 300 |
| ACCGATAACG | GCTATGACAT | CAGTAATTAT | CGTCAGATAA | TGAAAGAGTA | TGGCACAATG | 360 |
| GAGGATTTTG | ATAGCCTTGT | TGCCGAAATG | AAAAAACGAA | ATATGCGCTT | AATGATCGAC | 420 |
| GTGGTCATTA | ACCATACCAG | TGATCAACAC | CCGTGGTTTA | TTCAGAGTAA | AAGCGATAAA | 480 |
| AACAACCCTT | ATCGTGACTA | TTATTTCTGG | CGTGACGGAA | AAGATAATCA | GCCACCTAAT | 540 |
| AATTACCCCT | CATTTTTCGG | CGGCTCGGCA | TGGCAAAAAG | ATGCAAAGTC | AGGACAGTAC | 600 |
| TATTTACACT | ATTTTGCCAG | ACAGCAACCT | GATCTCAACT | GGGATAACCC | GAAAGTACGT | 660 |
| GAGGATCTTT | ACGCAATGCT | CCGCTTCTGG | CTGGATAAAG | GCGTTTCAGG | CATGCGATTT | 720 |
| GATACGGTGG | CAACTTATTC | CAAAATCCCG | GGATTTCCCA | ATCTGACACC | TGAACAACAG | 780 |
| AAAAATTTTG | CTGAACAATA | CACCATGGGD | CCTAATATTC | ATCGATACAT | TCAGGAAATG | 840 |
| AACCGGAAAG | TTCTGTCCCG | GTATGATGTG | GCCACCGCGG | GTGAAATTTT | TGGCGTCCCG | 900 |
| CTGGATCGTT | CGTCGCAGTT | TTTTGATCGC | CGCCGACATG | AGCTGAATAT | GGCGTTTATG | 960 |
| TTTGACCTCA | TTCGTCTCGA | TCGCGACAGC | AATGAACGCT | GGCGTCACAA | GTCGTGGTCG | 1020 |
| CTCTCTCAGT | TCCGCCAGAT | CATCAGCAAA | ATGGATGTCA | CGGTCGGAAA | GTATGGCTGG | 1080 |
| AACACGTTCT | TCTTAGACAA | CCATGACAAC | CCCCGTGCGG | TATCTCACTT | CGGGGATGAC | 1140 |
| AGGCCGCAAT | GGCGGGAGGC | GTCGGCTAAG | GCACTGGCGA | CGATTACCCT | CACTCAGCGG | 1200 |
| GCGACGCCGT | TTATTTATCA | GGGTTCAGAG | CTGGGAATGA | CTAATTATCC | CTTCAGGCAA | 1260 |
| CTCAACGAAT | TTGACGACAT | CGAGGTCAAA | GGTTTCTGGC | AGGATTATGT | CCAGAGTGGA | 1320 |
| AAAGTCACGG | CCACAGAGTT | TCTCGATAAT | GTGCGCCTGA | CGAGCCGCGA | TAACAGCAGA | 1380 |
| ACACCTTTCC | AGTGGAATGA | CACCCTGAAT | GCTGGTTTTA | CTCGCGGAAA | GCCGTGGTTT | 1440 |
| CACATCAACC | CAAACTATGT | GGAGATCAAC | SCCGAACGCG | AAGAAACCCG | CGAAGATTCA | 1500 |
| GTGCTGAATT | ACTATAAAAA | AATGATTCAG | CTACGCCACC | ATATCCCTGC | TCTGGTATAT | 1560 |
| GGCGCCTATC | AGGATCTTAA | TCCACAGGAC | AATACCGTTT | ATGCCTATAC | CCGAACGCTG | 1620 |
| GGTAACGAGC | GTTATCTGGT | CGTGGTGAAC | TTTAAGGAGT | ACCCGGTCCG | CTATACTCTC | 1680 |
| CCGGCTAATG | ATGCCATCGA | GGAAGTGGTC | ATTGATACTC | AGCAGCAAGG | TGCGCCGCAC | 1740 |
| AGCACATCCC | TGTCATTGAG | CCCCTGGCAG | GCAGGTGCGT | ATAAGCTGCG | GTAA | 1794 |

(2) INFORMATION FOR SEQ ID NO:12:

(i) SEQUENCE CHARACTERISTICS:
       (A) LENGTH: 597 amino acids
       (B) TYPE: amino acid
       (C) STRANDEDNESS: single
       (D) TOPOLOGY: linear (ii) MOLECULE TYPE: peptide (ix) FEATURE:

(A) NAME/KEY: Peptide
                (B) LOCATION: 270
                (D) OTHER INFORMATION: /note= "X = Unknown"

(ix) FEATURE:
                (A) NAME/KEY: Peptide
                (B) LOCATION: 491
                (D) OTHER INFORMATION: /note= "X = Unknown"

(xi) SEQUENCE DESCRIPTION: SEQ ID NO:12:

| | | | | | | | | | | | | | | | |
|---|---|---|---|---|---|---|---|---|---|---|---|---|---|---|---|
| Met | Ser | Phe | Val | Thr | Leu | Arg | Thr | Gly | Val | Ala | Val | Ala | Leu | Ser | Ser |
| 1 | | | | 5 | | | | | 10 | | | | | 15 | |
| Leu | Ile | Ile | Ser | Leu | Ala | Cys | Pro | Ala | Val | Ser | Ala | Ala | Pro | Ser | Leu |
| | | | 20 | | | | | 25 | | | | | 30 | | |
| Asn | Gln | Asp | Ile | His | Val | Gln | Lys | Glu | Ser | Glu | Tyr | Pro | Ala | Trp | Trp |
| | | | 35 | | | | | 40 | | | | | 45 | | |
| Lys | Glu | Ala | Val | Phe | Tyr | Gln | Ile | Tyr | Pro | Arg | Ser | Phe | Lys | Asp | Thr |
| 50 | | | | | 55 | | | | | 60 | | | | | |
| Asn | Asp | Asp | Gly | Ile | Gly | Asp | Ile | Arg | Gly | Ile | Ile | Glu | Lys | Leu | Asp |
| 65 | | | | | 70 | | | | | 75 | | | | | 80 |
| Tyr | Leu | Lys | Ser | Leu | Gly | Ile | Asp | Ala | Ile | Trp | Ile | Asn | Pro | His | Tyr |
| | | | | 85 | | | | | 90 | | | | | 95 | |
| Asp | Ser | Pro | Asn | Thr | Asp | Asn | Gly | Tyr | Asp | Ile | Ser | Asn | Tyr | Arg | Gln |
| | | | | 100 | | | | | 105 | | | | | 110 | |
| Ile | Met | Lys | Glu | Tyr | Gly | Thr | Met | Glu | Asp | Phe | Asp | Ser | Leu | Val | Ala |
| | | | 115 | | | | | 120 | | | | | 125 | | |
| Glu | Met | Lys | Lys | Arg | Asn | Met | Arg | Leu | Met | Ile | Asp | Val | Val | Ile | Asn |
| | | 130 | | | | | 135 | | | | | 140 | | | |
| His | Thr | Ser | Asp | Gln | His | Pro | Trp | Phe | Ile | Gln | Ser | Lys | Ser | Asp | Lys |
| 145 | | | | | 150 | | | | | 155 | | | | | 160 |
| Asn | Asn | Pro | Tyr | Arg | Asp | Tyr | Tyr | Phe | Trp | Arg | Asp | Gly | Lys | Asp | Asn |
| | | | | 165 | | | | | 170 | | | | | 175 | |
| Gln | Pro | Pro | Asn | Asn | Tyr | Pro | Ser | Phe | Phe | Gly | Gly | Ser | Ala | Trp | Gln |
| | | | | 180 | | | | | 185 | | | | | 190 | |
| Lys | Asp | Ala | Lys | Ser | Gly | Gln | Tyr | Tyr | Leu | His | Tyr | Phe | Ala | Arg | Gln |
| | | | 195 | | | | | 200 | | | | | 205 | | |
| Gln | Pro | Asp | Leu | Asn | Trp | Asp | Asn | Pro | Lys | Val | Arg | Glu | Asp | Leu | Tyr |
| | | 210 | | | | | 215 | | | | | 220 | | | |
| Ala | Met | Leu | Arg | Phe | Trp | Leu | Asp | Lys | Gly | Val | Ser | Gly | Met | Arg | Phe |
| 225 | | | | | 230 | | | | | 235 | | | | | 240 |
| Asp | Thr | Val | Ala | Thr | Tyr | Ser | Lys | Ile | Pro | Gly | Phe | Pro | Asn | Leu | Thr |
| | | | | 245 | | | | | 250 | | | | | 255 | |
| Pro | Glu | Gln | Gln | Lys | Asn | Phe | Ala | Glu | Gln | Tyr | Thr | Met | Xaa | Pro | Asn |
| | | | | 260 | | | | | 265 | | | | | 270 | |
| Ile | His | Arg | Tyr | Ile | Gln | Glu | Met | Asn | Arg | Lys | Val | Leu | Ser | Arg | Tyr |
| | | | | 275 | | | | | 280 | | | | | 285 | |
| Asp | Val | Ala | Thr | Ala | Gly | Glu | Ile | Phe | Gly | Val | Pro | Leu | Asp | Arg | Ser |
| | | | 290 | | | | | 295 | | | | | 300 | | |
| Ser | Gln | Phe | Phe | Asp | Arg | Arg | His | Glu | Leu | Asn | Met | Ala | Phe | Met |
| 305 | | | | | 310 | | | | | 315 | | | | | 320 |
| Phe | Asp | Leu | Ile | Arg | Leu | Asp | Arg | Asp | Ser | Asn | Glu | Arg | Trp | Arg | His |
| | | | | 325 | | | | | 330 | | | | | 335 | |
| Lys | Ser | Trp | Ser | Leu | Ser | Gln | Phe | Arg | Gln | Ile | Ile | Ser | Lys | Met | Asp |
| | | | 340 | | | | | 345 | | | | | 350 | | |
| Val | Thr | Val | Gly | Lys | Tyr | Gly | Trp | Asn | Thr | Phe | Phe | Leu | Asp | Asn | His |
| | | | 355 | | | | | 360 | | | | | 365 | | |

```
Asp Asn Pro Arg Ala Val Ser His Phe Gly Asp Asp Arg Pro Gln Trp
370                 375                 380

Arg Glu Ala Ser Ala Lys Ala Leu Ala Thr Ile Thr Leu Thr Gln Arg
385                 390                 395                 400

Ala Thr Pro Phe Ile Tyr Gln Gly Ser Glu Leu Gly Met Thr Asn Tyr
                405                 410                 415

Pro Phe Arg Gln Leu Asn Glu Phe Asp Asp Ile Glu Val Lys Gly Phe
            420                 425                 430

Trp Gln Asp Tyr Val Gln Ser Gly Lys Val Thr Ala Thr Glu Phe Leu
        435                 440                 445

Asp Asn Val Arg Leu Thr Ser Arg Asp Asn Ser Arg Thr Pro Phe Gln
450                 455                 460

Trp Asn Asp Thr Leu Asn Ala Gly Phe Thr Arg Gly Lys Pro Trp Phe
465                 470                 475                 480

His Ile Asn Pro Asn Tyr Val Glu Ile Asn Xaa Glu Arg Glu Glu Thr
                485                 490                 495

Arg Glu Asp Ser Val Leu Asn Tyr Tyr Lys Lys Met Ile Gln Leu Arg
                500                 505                 510

His His Ile Pro Ala Leu Val Tyr Gly Ala Tyr Gln Asp Leu Asn Pro
            515                 520                 525

Gln Asp Asn Thr Val Tyr Ala Tyr Thr Arg Thr Leu Gly Asn Glu Arg
530                 535                 540

Tyr Leu Val Val Val Asn Phe Lys Glu Tyr Pro Val Arg Tyr Thr Leu
545                 550                 555                 560

Pro Ala Asn Asp Ala Ile Glu Glu Val Val Ile Asp Thr Gln Gln Gln
                565                 570                 575

Gly Ala Pro His Ser Thr Ser Leu Ser Leu Ser Pro Trp Gln Ala Gly
            580                 585                 590

Ala Tyr Lys Leu Arg
        595
```

(2) INFORMATION FOR SEQ ID NO:13:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 1237..1331
        (D) OTHER INFORMATION: /note= "N = Unknown"

(xi) SEQUENCE DESCRIPTION: SEQ ID NO:13:

```
ATGCTTATGA AGAGATTATT CGCCGCGTCT CTGATGCTTG CTTTTTTCAAG CGTCTCCTCT      60

GTGAGGGCTG AGGAGGCCGT AAAGCCGGGC GCGCCATGGT GGAAAAGTGC TGTCTTCTAT     120

CAGGTCTATC CGCGCTCGTT CAAGGATACC AACGGTGATG GGATCGGCGA TTTCAAAGGA     180

CTGACGGAGA AGCTCGACTA TCTCAAGGGG CTCGGCATAG ACGCCATCTG GATCAATCCA     240

CATTACGCGT CTCCCAACAC CGATAATGGC TACGATATCA GCGACTATCG AGAGGTCATG     300

AAGGAATATG GGACGATGGA GGACTTCGAT CGTCTGATGG CTGAGTTGAA GAAGCGCGGC     360

ATGCGGCTCA TGGTTGATGT CGTGATCAAC CATTCGAGTG ACCAACACGA ATGGTTCAAG     420

AGCAGCCGGG CCTCCAAAGA CAATCCCTAC CGTGACTATT ATTTCTGGCG TGACGGCAAA     480

GACGGTCACG AGCCAAACAA TTACCCTTCC TTCTTCGGCG GTTCGGCATG GGAGAAGGAC     540
```

```
CCCGTAACCG GGCAATATTA CCTGCATTAT TTCGGTCGTC AGCAGCCAGA TCTGAACTGG    600

GACACGCCGA AGCTTCGCGA GGAACTCTAT GCGATGCTGC GGTTCTGGCT CGACAAGGGC    660

GTATCAGGCA TGCGGTTCGA TACGGTGGCT ACCTACTCGA AGACACCGGG TTTCCCGGAT    720

CTGACACCGG AGCAGATGAA GAACTTCGCG GAGGCCTATA CCCAGGGGCC GAACCTTCAT    780

CGTTACCTGC AGGAAATGCA CGAGAAGGTC TTCGATCATT ATGACGCGGT CACGGCCGGC    840

GAAATCTTCG GCGCTCCGCT CAATCAAGTG CCGCTGTTCA TCGACAGCCG GAGGAAAGAG    900

CTGGATATGG CTTTCACCTT CGATCTGATC CGTTATGATC GCGCACTGGA TCGTTGGCAT    960

ACCATTCCGC GTACCTTAGC GGACTTCCGT CAAACGATCG ATAAGGTCGA CGCCATCGCG   1020

GGCGAATATG GCTGGAACAC GTTCTTCCTC GGCAATCACG ACAATCCCCG TGCGGTATCG   1080

CATTTTGGTG ACGATCGGCC GCAATGGCGC GAAGCCTCGG CCAAGGCTCT GGCCACCGTC   1140

ACCTTGACCC AGCGAGGAAC GCCGTTCATC TTCCAAGGAG ATGAACTCGG AATGACCAAC   1200

TACCCCTTCA AGACGCTGCA GGACTTTGAT GATATCNNNN NNNNNNNNNN NNNNNNNNNN   1260

NNNNNNNNNN NNNNNNNNNN NNNNNNNNNN NNNNNNNNNN NNNNNNNNNN NNNNNNNNNN   1320

NNNNNNNNNN NTGTGGCGTT GACTAGCCGA GCAAACGCCC GCACGCCCTT TCAATGGGAT   1380

GACAGTGCTA ATGCGGGATT CACAACTGGC AAGCCTTGGC TAAAGGTCAA TCCAAACTAC   1440

ACTGAGATCA ACGCCGCGCG GGAAATTGGC GATCCTAAAT CGGTCTACAG CTTTTACCGC   1500

AACCTGATCT CAATCCGGCA TGAAACTCCC GCTCTTTCGA CCGGGAGCTA TCGCGACATC   1560

GATCCGAGTA ATGCCGATGT CTATGCCTAT ACGCGCAGCC AGGATGGCGA GACCTATCTG   1620

GTCGTAGTCA ACTTCAAGGC AGAGCCAAGG AGTTTCACGC TTCCGGACGG CATGCATATT   1680

GCCGAAACCC TGATTGAGAG CAGTTCGCCA GCAGCTCCGG CGGCGGGGGC TGCAAGCCTT   1740

GAGCTGCAGC CTTGGCAGTC CGGCATCTAC AAGGTGAAGT AA                      1782

(2) INFORMATION FOR SEQ ID NO:14:

(i) SEQUENCE CHARACTERISTICS:
        (A) LENGTH: 593 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 413..444
        (D) OTHER INFORMATION: /note= "Xaa = Unknown"

(xi) SEQUENCE DESCRIPTION: SEQ ID NO:14:

Met Leu Met Lys Arg Leu Phe Ala Ala Ser Leu Met Leu Ala Phe Ser
1               5                   10                  15

Ser Val Ser Ser Val Arg Ala Glu Glu Ala Val Lys Pro Gly Ala Pro
                20                  25                  30

Trp Trp Lys Ser Ala Val Phe Tyr Gln Val Tyr Pro Arg Ser Phe Lys
            35                  40                  45

Asp Thr Asn Gly Asp Gly Ile Gly Asp Phe Lys Gly Leu Thr Glu Lys
        50                  55                  60

Leu Asp Tyr Leu Lys Gly Leu Gly Ile Asp Ala Ile Trp Ile Asn Pro
65                  70                  75                  80

His Tyr Ala Ser Pro Asn Thr Asp Asn Gly Tyr Asp Ile Ser Asp Tyr
                85                  90                  95

Arg Glu Val Met Lys Glu Tyr Gly Thr Met Glu Asp Phe Asp Arg Leu
```

```
                   100                 105                 110
Met Ala Glu Leu Lys Lys Arg Gly Met Arg Leu Met Val Asp Val Val
            115                 120                 125

Ile Asn His Ser Ser Asp Gln His Glu Trp Phe Lys Ser Ser Arg Ala
130                 135                 140

Ser Lys Asp Asn Pro Tyr Arg Asp Tyr Tyr Phe Trp Arg Asp Gly Lys
145                 150                 155                 160

Asp Gly His Glu Pro Asn Asn Tyr Pro Ser Phe Phe Gly Gly Ser Ala
                165                 170                 175

Trp Glu Lys Asp Pro Val Thr Gly Gln Tyr Tyr Leu His Tyr Phe Gly
            180                 185                 190

Arg Gln Gln Pro Asp Leu Asn Trp Asp Thr Pro Lys Leu Arg Glu Glu
            195                 200                 205

Leu Tyr Ala Met Leu Arg Phe Trp Leu Asp Lys Gly Val Ser Gly Met
210                 215                 220

Arg Phe Asp Thr Val Ala Thr Tyr Ser Lys Thr Pro Gly Phe Pro Asp
225                 230                 235                 240

Leu Thr Pro Glu Gln Met Leu Asn Phe Ala Glu Ala Tyr Thr Gln Gly
                245                 250                 255

Pro Asn Leu His Arg Tyr Leu Gln Glu Met His Glu Lys Val Phe Asp
            260                 265                 270

His Tyr Asp Ala Val Thr Ala Gly Glu Ile Phe Gly Ala Pro Leu Asn
            275                 280                 285

Gln Val Pro Leu Phe Ile Asp Ser Arg Arg Lys Glu Leu Asp Met Ala
            290                 295                 300

Phe Thr Phe Asp Leu Ile Arg Tyr Asp Arg Ala Leu Asp Arg Trp His
305                 310                 315                 320

Thr Ile Pro Arg Thr Leu Ala Asp Phe Arg Gln Thr Ile Asp Lys Val
                325                 330                 335

Asp Ala Ile Ala Gly Glu Tyr Gly Trp Asn Thr Phe Phe Leu Gly Asn
            340                 345                 350

His Asp Asn Pro Arg Ala Val Ser His Phe Gly Asp Asp Arg Pro Gln
            355                 360                 365

Trp Arg Glu Ala Ser Ala Lys Ala Leu Ala Thr Val Thr Leu Thr Gln
370                 375                 380

Arg Gly Thr Pro Phe Ile Phe Gln Gly Asp Glu Leu Gly Met Thr Asn
385                 390                 395                 400

Tyr Pro Phe Lys Thr Leu Gln Asp Phe Asp Ile Xaa Xaa Xaa Xaa
                405                 410                 415

Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Val Ala Leu Thr
            435                 440                 445

Ser Arg Ala Asn Ala Arg Thr Pro Phe Gln Trp Asp Asp Ser Ala Asn
450                 455                 460

Ala Gly Phe Thr Thr Gly Lys Pro Trp Leu Lys Val Asn Pro Asn Tyr
465                 470                 475                 480

Thr Glu Ile Asn Ala Ala Arg Glu Ile Gly Asp Pro Lys Ser Val Tyr
                485                 490                 495

Ser Phe Tyr Arg Asn Leu Ile Ser Ile Arg His Glu Thr Pro Ala Leu
            500                 505                 510

Ser Thr Gly Ser Tyr Arg Asp Ile Asp Pro Ser Asn Ala Asp Val Tyr
            515                 520                 525
```

```
Ala Tyr Thr Arg Ser Gln Asp Gly Glu Thr Tyr Leu Val Val Val Asn
    530                 535                 540

Phe Lys Ala Glu Pro Arg Ser Phe Thr Leu Pro Asp Gly Met His Ile
545                 550                 555                 560

Ala Glu Thr Leu Ile Glu Ser Ser Ser Pro Ala Pro Ala Ala Gly
                565                 570                 575

Ala Ala Ser Leu Glu Leu Gln Pro Trp Gln Ser Gly Ile Tyr Lys Val
            580                 585                 590

Lys
```

(2) INFORMATION FOR SEQ ID NO:15:

(i) SEQUENCE CHARACTERISTICS:
        (A) LENGTH: 1704 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
ATGACTGAAA AGTTATCCTT CGAGTCGACA ACAATCTCGC GTCGCTGGTG GAAAGAGGCT    60

GTTGTCTATC AGGTGTATCC CCGCTCGTTC CAGGATTCGA ACGGGACGG CATCGGCGAC    120

CTTCCGGGCA TAACTGCGAG GCTAGATTAC ATCCTCGGTC TAGGCGTTAG TGTCATCTGG   180

CTCAGCCCCC ATTTCGACTC TCCGAATGCT GACAACGGCT ACGATATCCG TGACTATCGC   240

AAGGTGATGC GCGAATTCGG CACCATGGCG GATTTCGATC ACCTGCTGGC CGAGACGAAA   300

AAGCGCGGCA TGCGGCTGAT CATCGATCTC GTCGTCAACC ATACCAGCGA CGAGCATGTC   360

TGGTTTGCCG AAAGCCGGGC CTCGAAAAAC AGCCCGTACC GTGATTACTA CATCTGGCAT   420

CCCGGCCGGG ACGGCGCCGA GCCGAACGAC TGGCGCTCAT TTTTCTCGGG CTCGGCATGG   480

ACTTTCGACC AGCCAACCGG CGAATACTAC ATGCATCTTT CGCCGATAA ACAGCCGGAT    540

ATCAACTGGG ACAATCCGGC TGTGCGCGCC GATGTCTATG ACATCATGCG CTTTTGGCTG   600

GACAAGGGCG TCGACGGATT CCGCATGGAT GTCATCCCCT TCATCTCCAA GCAAGACGGC   660

CTGCCCGACT ATCCTGACCA TCATCGCGGC GCGCCGCAGT TTTTCCACGG TTCGGGTCCC   720

CGCTTGCACG ACTATCTTCA GGAAATGAAC CGCGAGGTAT TGTCGCATTA CGATGTGATG   780

ACGGTTGGCG AGGCCTTCGG TGTGACGGCG GATGCGACGC CGCTTCTGGT CGACGAACGG   840

CGCCGCGAAC TGAACATGAT CTTCAATTTC GACGCCGTGC GCATCGGCCG TGGCGAGACC   900

TGGCACACTA AGCCTTGGGC CCTGCCGGAA CTTAAGGCGA TCTATGCCCG TCTGGACGCT   960

GCGACCGACC AGCACTGCTG GGGTACGGTC TTTCTCTCCA ACCACGACAA TCCTCGTCTC  1020

GTCTCCCGGT TCGGTGATGA TCATCCTGAC TGGCGGGTGG CGTCGGCCAA GGTTCTTGCC  1080

ACACTTCTCC TAACGCTGAA GGGCACGCCT TTCATCTACC AAGGCGATGA ATTGGGCATG  1140

ACCAACTATC CTCGGCTCGG TCGAGGAGAC GACGATATCG AGGTGCGCAA CGCCTGGCAG  1200

GCTGAGGTCA TGACCGGTAA GGCGGATGCA GCCGAATTTC TCGGGGAGAT GCTGAAGATT  1260

TCCCGCGATC ATTCCCGCAC ACCGATGCAA TGGGACGCCA GTCTCGACGG TGGTTTCACT  1320

CGGGGTGAAA AGCCCTGGCT ATCGGTCAAT CCGAACTATC GGGCGATCAA TGCGGATGCG  1380

GCACTCGCCG ATCCCGATTC GATCTACCAT TATTACGCCG CACTCATCCG TTTCCGGCGC  1440

GAGACACCGG CGCTCATCTA CGGCGATTAT GACGACTTGG CGCCGGATCA TCCGCACCTC  1500

TTCGTCTATA CAAGAACATT GGGGTCCGAG CGCTATCTGG TCGCGCTTAA CTTCTCCGGC  1560

GATGCGCAGG CACTTGTTCT CCCGACAGAC CTGAGCGCCG CGTCACCTGT TATCGGGCGC  1620
```

```
GCCCCGCAAG TGGACCGCAT GCAGCATGAT GCTGCACGGA TCGAGCTGAT GGGTTGGGAA      1680

GCGCGGGTCT ACCACTGCGC ATGA                                             1704
```

(2) INFORMATION FOR SEQ ID NO:16:

(i) SEQUENCE CHARACTERISTICS:
        (A) LENGTH: 567 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Met Thr Glu Lys Leu Ser Phe Glu Ser Thr Thr Ile Ser Arg Arg Trp
 1               5                  10                  15

Trp Lys Glu Ala Val Val Tyr Gln Val Tyr Pro Arg Ser Phe Gln Asp
                20                  25                  30

Ser Asn Gly Asp Gly Ile Gly Asp Leu Pro Gly Ile Thr Ala Arg Leu
            35                  40                  45

Asp Tyr Ile Leu Gly Leu Gly Val Ser Val Ile Trp Leu Ser Pro His
50                  55                  60

Phe Asp Ser Pro Asn Ala Asp Asn Gly Tyr Asp Ile Arg Asp Tyr Arg
65                  70                  75                  80

Lys Val Met Arg Glu Phe Gly Thr Met Ala Asp Phe Asp His Leu Leu
                85                  90                  95

Ala Glu Thr Lys Lys Arg Gly Met Arg Leu Ile Ile Asp Leu Val Val
                100                 105                 110

Asn His Thr Ser Asp Glu His Val Trp Phe Ala Glu Ser Arg Ala Ser
            115                 120                 125

Lys Asn Ser Pro Tyr Arg Asp Tyr Tyr Ile Trp His Pro Gly Arg Asp
130                 135                 140

Gly Ala Glu Pro Asn Asp Trp Arg Ser Phe Phe Ser Gly Ser Ala Trp
145                 150                 155                 160

Thr Phe Asp Gln Pro Thr Gly Glu Tyr Tyr Met His Leu Phe Ala Asp
                165                 170                 175

Lys Gln Pro Asp Ile Asn Trp Asp Asn Pro Ala Val Arg Ala Asp Val
                180                 185                 190

Tyr Asp Ile Met Arg Phe Trp Leu Asp Lys Gly Val Asp Gly Phe Arg
            195                 200                 205

Met Asp Val Ile Pro Phe Ile Ser Lys Gln Asp Gly Leu Pro Asp Tyr
210                 215                 220

Pro Asp His His Arg Gly Ala Pro Gln Phe Phe His Gly Ser Gly Pro
225                 230                 235                 240

Arg Leu His Asp Tyr Leu Gln Glu Met Asn Arg Glu Val Leu Ser His
                245                 250                 255

Tyr Asp Val Met Thr Val Gly Glu Ala Phe Gly Val Thr Ala Asp Ala
                260                 265                 270

Thr Pro Leu Leu Val Asp Glu Arg Arg Glu Leu Asn Met Ile Phe
            275                 280                 285

Asn Phe Asp Ala Val Arg Ile Gly Arg Gly Glu Thr Trp His Thr Lys
290                 295                 300

Pro Trp Ala Leu Pro Glu Leu Lys Ala Ile Tyr Ala Arg Leu Asp Ala
305                 310                 315                 320

Ala Thr Asp Gln His Cys Trp Gly Thr Val Phe Leu Ser Asn His Asp
                325                 330                 335
```

```
Asn Pro Arg Leu Val Ser Arg Phe Gly Asp Asp His Pro Asp Trp Arg
            340                 345                 350

Val Ala Ser Ala Lys Val Leu Ala Thr Leu Leu Leu Thr Leu Lys Gly
            355                 360                 365

Thr Pro Phe Ile Tyr Gln Gly Asp Glu Leu Gly Met Thr Asn Tyr Pro
        370                 375                 380

Arg Leu Gly Arg Gly Asp Asp Ile Glu Val Arg Asn Ala Trp Gln
385                 390                 395                 400

Ala Glu Val Met Thr Gly Lys Ala Asp Ala Glu Phe Lys Gly Glu
                405                 410                 415

Met Leu Lys Ile Ser Arg Asp His Ser Arg Thr Pro Met Gln Trp Asp
            420                 425                 430

Ala Ser Leu Asp Gly Gly Phe Thr Arg Gly Glu Lys Pro Trp Leu Ser
            435                 440                 445

Val Asn Pro Asn Tyr Arg Ala Ile Asn Ala Asp Ala Ala Leu Ala Asp
            450                 455                 460

Pro Asp Ser Ile Tyr His Tyr Tyr Ala Ala Leu Ile Arg Phe Arg Arg
465                 470                 475                 480

Glu Thr Pro Ala Leu Ile Tyr Gly Asp Tyr Asp Asp Leu Ala Pro Asp
                485                 490                 495

His Pro His Leu Phe Val Tyr Thr Arg Thr Leu Gly Ser Glu Arg Tyr
            500                 505                 510

Leu Val Ala Leu Asn Phe Ser Gly Asp Ala Gln Ala Leu Val Leu Pro
            515                 520                 525

Thr Asp Leu Ser Ala Ala Ser Pro Val Ile Gly Arg Ala Pro Gln Val
            530                 535                 540

Asp Arg Met Gln His Asp Ala Ala Arg Ile Glu Leu Met Gly Trp Glu
545                 550                 555                 560

Ala Arg Val Tyr His Cys Ala
                565

(2)   INFORMATION FOR SEQ ID NO:17:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (geonomic)

(xi) SEQUENCE DESCRIPTION: SEQ ID NO:17:

TGGTGGAARG ARGCTGT                                                    17

(2)   INFORMATION FOR SEQ ID NO:18:

(i) SEQUENCE CHARACTERISTICS
          (A) LENGTH: 20 base pairs
          (B) TYPE: nucleic acid
          (C) STRANDEDNESS: single
          (D) TOPOLOGY: linear (ii) MOLECULE TYPE: DNA (geonomic)

(xi) SEQUENCE DESCRIPTION: SEQ ID NO:18:

TCCCAGTTCA GRTCCGGCTG                                                 20

(2)   INFORMATION FOR SEQ ID NO:19:
```

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (geonomic)

(xi) SEQUENCE DESCRIPTION: SEQ ID NO:19:

AAAGATGGCG KCGAAAAGA                                            19

(2) INFORMATION FOR SEQ ID NO:20:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (geonomic)

(xi) SEQUENCE DESCRIPTION: SEQ ID NO:20:

TGGAATGCCT TYTTCTT                                              17

(2) INFORMATION FOR SEQ ID NO:21:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (geonomic)

(xi) SEQUENCE DESCRIPTION: SEQ ID NO:21:

ATCCCGAAGT GGTGGAAGGA GGC                                       23

(2) INFORMATION FOR SEQ ID NO:22:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (geonomic)

(ix) SEQUENCE DESCRIPTION: SEQ ID NO:22:

CGGAATTCTT ATGCCCCGTC AAGGA                                     25

(2) INFORMATION FOR SEQ ID NO:23:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (geonomic)

(ix) SEQUENCE DESCRIPTION: SEQ ID NO:23:

TGGTGGAAAG AAGCTGT                                              17

(2) INFORMATION FOR SEQ ID NO:24:

(i) SEQUENCE CHARACTERISTICS:
      (A) LENGTH: 20 base pairs
      (B) TYPE: nucleic acid
      (C) STRANDEDNESS: single
      (D) TOPOLOGY: linear -continued (ii) MOLECULE TYPE: DNA (geonomic)

(ix) SEQUENCE DESCRIPTION: SEQ ID NO:24:

TCCCAGTTCA GGTCCGGCTG                                            20

(2)  INFORMATION FOR SEQ ID NO:25:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO:25:

CARTTYGGYT AYGG                                                  14

(2)  INFORMATION FOR SEQ ID NO:26:

(i) SEQUENCE CHARACTERISTICS
        (A) LENGTH: 17 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO:26:

GTTTTCCCAG TCACGAC                                               17

PREPARATION OF ACARIOGENIC SUGAR SUBSTITUTES

This application is a division of application Ser. No. 08/374,155, filed Jan. 18, 1995 pending.

DESCRIPTION

The present invention relates to an improved process for the preparation of non-cariogenic sugars, in particular trehalulose and/or palatinose, using recombinant DNA technology.

The acariogenic sugar substitutes palatinose (isomaltulose) and trehalulose are produced on a large scale from sucrose by an enzymatic rearrangement using immobilized bacterial cells (for example of the species *Protaminobacter rubrum, Erwinia rhapontici, Serratia plymuthica*). This entails the α1→β2 glycosidic linkage existing between the two monosaccharide units of the disaccharide sucrose being isomerized to an α1→6 linkage in palatinose and to an α1→α1 linkage in trehalulose. This rearrangement of sucrose to give the two acariogenic disaccharides takes place with catalysis by the bacterial enzyme sucrose isomerase, also called sucrose mutase. Depending on the organism used, this reaction results in a product mixture which, besides the desired acariogenic disaccharides palatinose and trehalulose, also contains certain proportions of unwanted monosaccharides (glucose and/or fructose). These monosaccharide contents are a considerable industrial problem because elaborate purification procedures (usually fractional crystallizations) are necessary to remove them.

One object on which the present invention is based was thus to suppress as far as possible the formation of monosaccharides in the isomerization of sucrose to trehalulose and/or palatinose. Another object on which the present invention is based was to provide organisms which produce palatinose and/or trehalulose in a higher yield than do known organisms.

To achieve these objects, recombinant DNA molecules, organisms transformed with recombinant DNA molecules, recombinant proteins and an improved process for the preparation of non-cariogenic sugars, in particular of palatinose and/or trehalulose, are provided.

The invention relates to a DNA sequence which codes for a protein with a sucrose isomerase activity and comprises (a) one of the nucleotide sequences shown in SEQ ID NO:1, SEQ ID NO:2, SEQ ID NO:3, SEQ ID NO:9, SEQ ID NO:11 or SEQ ID NO:13, where appropriate without the signal peptide-coding region, (b) a nucleotide sequence corresponding to the sequences from (a) within the scope of the degeneracy of the genetic code, or (c) a nucleotide sequence which hybridizes with the sequences from (a) and/or (b).

In the context of the present invention, the term "protein with a sucrose isomerase activity" is intended to embrace those proteins which are able to isomerize sucrose to other disaccharides with conversion of the α1→β2 glycosidic linkage between glucose and fructose in sucrose into another glycosidic linkage between two monosaccharide units, in particular into an α1→6 linkage and/or an α1→α1 linkage. The term "protein with a sucrose isomerase activity" therefore particularly preferably relates to a protein which is able to isomerize sucrose to palatinose and/or trehalulose. Moreover, the proportion of palatinose and trehalulose in the total disaccharides formed by isomerization of sucrose is preferably ≧2%, particularly preferably ≧20% and most preferably ≧50%.

The nucleotide sequence shown in SEQ ID NO:1 codes for the complete sucrose isomerase from the microorganism *Protaminobacter rubrum* (CBS 547,77) including the signal peptide region. The nucleotide sequence shown in SEQ ID NO:3 codes for the N-terminal section of the sucrose isomerase from the microorganism *Erwinia rhapontici* (NCPPB 1578) including the signal peptide region. The nucleotide sequence shown in SEQ ID NO:3 codes for a section of the sucrose isomerase from the microorganism SZ 62 (Enterobacter spec.).

The region which codes for the signal peptide in SEQ ID NO:1 extends from nucleotide 1–99. The region coding for the signal peptide in SEQ ID NO:2 extends from nucleotide 1–108. The DNA sequence according to the present invention also embraces the nucleotide sequences shown in SEQ ID NO:1 and SEQ ID NO:2 without the region coding for the signal peptide because the signal peptide is, as a rule, necessary only for correct localization of the mature protein in a particular cell compartment (for example in the periplasmic space between the outer and inner membrane, in the outer membrane or in the inner membrane) or for extracellular export, but not for the enzymatic activity as such. The present invention thus furthermore embraces sequences which also code for the mature protein (without signal peptide) and are operatively linked to heterologous signal sequences, in particular to prokaryotic signal sequences as described, for example, in E. L. Winnacker, Gene und Klone, Eine Einführung in die Gentechnologie, VCH-Verlagsgesellschaft Weinheim, Germany (1985), p. 256.

Nucleotide sequence SEQ ID NO:9 codes for a variant of the isomerase from *Protaminobacter rubrum*. Nucleotide sequence SEQ ID NO:11 codes for the complete isomerase from the isolate SZ 62. Nucleotide sequence SEQ ID NO:13 codes for most of the isomerase from the microorganism MX-45 (FERM 11808 or FERM BP 3619).

Besides the nucleotide sequences shown in SEQ ID NO:1, SEQ ID NO:2, SEQ ID NO:3, SEQ ID NO:9, SEQ ID NO:11 or SEQ ID NO:13, and nucleotide sequences corresponding to one of these sequences within the scope of the degeneracy of the genetic code, the present invention also embraces a DNA sequence which hybridizes with one of these sequences, provided that it codes for a protein which is able to isomerize sucrose. The term "hybridization" according to the present invention is used as in Sambrook et al. (Molecular Cloning. A Laboratory Manual, Cold Spring Harbor Laboratory Press (1989), 1.101–1.104). According to the present invention, hybridization is the word used when a positive hybridization signal is still observed after washing for 1 hour with 1×SSC and 0.1% SDS at 55° C., preferably at 62° C. and particularly preferably at 68° C., in particular for 1 hour in 0.2×SSC and 0.1% SDS at 55° C., preferably at 62° C. and particularly preferably at 68° C. A nucleotide sequence which hybridizes under such washing conditions with one of the nucleotide sequences shown in SEQ ID NO:1 or SEQ ID NO:2, or with a nucleotide sequence which corresponds thereto within the scope of the degeneracy of the genetic code, is a nucleotide sequence according to the invention.

The DNA sequence according to the invention preferably has (a) one of the nucleotide sequences shown in SEQ ID NO:1, SEQ ID NO:2, SEQ ID NO:3, SEQ ID NO:9, SEQ ID NO:11 or SEQ ID NO:13, where appropriate without the signal peptide-coding region, or (b) a nucleotide sequence which is at least 70% homologous with the sequences from (a).

The DNA sequence according to the invention preferably also has an at least 80% homologous nucleotide sequence to the conserved part-regions of the nucleotide sequences shown in SEQ ID NO:1, SEQ ID NO:2, SEQ ID NO:3, SEQ ID NO:9, SEQ ID NO:11 or SEQ ID NO:13. These conserved part-regions are, in particular, from nucleotide 139–186, nucleotide 256–312, nucleotide 328–360, nucleotide 379–420 and/or nucleotide 424–444 in the nucleotide sequence shown in SEQ ID NO:1.

In a particularly preferred embodiment, the DNA sequence according to the invention has an at least 80% homologous, in particular an at least 90% homologous, nucleotide sequence to the part-regions (a) nucleotide 139–155 and/or (b) nucleotide 625–644 of the nucleotide sequence shown in SEQ ID NO:1.

Oligonucleotides derived from the above sequence regions have proved suitable as primers for PCR amplification of isomerase fragments from the genomic DNA of a large number of tested microorganisms, for example *Protaminobacter rubrum* (CBS 547, 77), *Erwinia rhapontici* (NCPPB 1578), isolate SZ 62 and *Pseudomonas mesoacidophila MX*-45 (FERM 11808).

Particularly preferably used for this purpose are the following oligonucleotides, where appropriate in the form of mixtures, where the bases in parentheses can be present as alternatives:

Oligonucleotide I (17 nt): 5'-TGGTGGAA(A,G)GA(G,A)GCTGT-3' (SEQ ID NO:17)

Oligonucleotide II (20 nt): 5'-TCCCAGTTCAG(G,A)TCCGGCTG-3' (SEQ ID NO:18)

Oligonucleotide I is derived from nucleotides 139–155 of SEQ ID NO:1, and oligonucleotide II is derived from the sequence, complementary to nucleotides 625–644, of SEQ ID NO:1. The differences between the homologous part-regions of the DNA sequences according to the invention and the sequences called oligonucleotide I and oligonucleotide II are preferably in each case not more than 2 nucleotides and particularly preferably in each case not more than 1 nucleotide.

In another particularly preferred embodiment of the present invention, the DNA sequence has an at least 80% homologous, in particular an at least 90% homologous, nucleotide sequence to the part-regions of (c) nucleotide 995–1013 and/or (d) nucleotide 1078–1094 of the nucleotide sequence shown in SEQ ID NO:1.

Oligonucleotides derived from the above sequence regions hybridize with sucrose isomerase genes from the organisms *Protaminobacter rubrum* and *Erwinia rhapontici*. The following oligonucleotides, where appropriate in the form of mixtures, are particularly preferably used, where the bases indicated in parentheses may be present as alternatives:

Oligonucleotide III (19 nt): AAAGATGGCG(G,T)CGAAAAGA (SEQ ID NO:19)

oligonucleotide IV (17 nt): 5'-TGGAATGCCTT(T,C)TTCTT-3' (SEQ ID NO:20)

Oligonucleotide III is derived from nucleotides 995–1013 of SEQ ID NO:1, and oligonucleotide IV is derived from nucleotides 1078–1094 of SEQ ID NO:1. The differences between the homologous part-regions of the DNA sequences according to the invention and the sequences called oligonucleotide III and IV are preferably in each case not more than 2 nucleotides and particularly preferably in each case not more than 1 nucleotide.

Nucleotide sequences according to the invention can be obtained in particular from microorganisms of the genera Protaminobacter, Erwinia, Serratia, Leuconostoc, Pseudomonas, Agrobacterium and Klebsiella. Specific examples of such microorganisms are *Protoaminobacter rubrum* (CBS 547,77), *Erwinia rhapontici* (NCPPB 1578), *Serratia plymuthica* (ATCC 15928), *Serratia marcescens* (NCIB 8285), *Leuconostoc mesenteroides* NRRL B-521f (ATCC 10830a), *Pseudomonas mesoacidophila MX*-45 (FERM 11808 or FERM BP 3619), *Agrobacterium radiobacter MX*-232 (FERM 12397 or FERM BP 3620), Klebsiella subspecies and Enterobacter species. The nucleotide sequences according to the invention can be isolated in a simple manner from the genome of the relevant microorganisms, for example using oligonucleotides from one or more of the conserved regions of SEQ ID NO:1, SEQ ID NO:2, SEQ ID NO:3, SEQ ID NO:9, SEQ ID NO:11 and SEQ ID NO:13, by standard techniques of amplification and/or hybridization, and be characterized. The nucleotide sequences according to the invention are preferably obtained by PCR amplification of the genomic DNA of the relevant organism using oligonucleotides I and II. A part-fragment of the relevant sucrose isomerase gene is obtained in this way and can subsequently be used as hybridization probe for isolating the complete gene from a gene bank of the relevant microorganism. Alternatively, the nucleotide sequences can be obtained by producing a gene bank from the particular organism and direct screening of this gene bank with oligonucleotides I, II, III and/or IV.

The present invention further relates to a vector which contains at least one copy of a DNA sequence according to the invention. This vector can be any prokaryotic or eukaryotic vector on which the DNA sequence according to the invention is preferably under the control of an expression signal (promoter, operator, enhancer, etc.). Examples of prokaryotic vectors are chromosomal vectors such as, for example, bacteriophages (for example bacteriophage λ) and extrachromosomal vectors such as, for example, plasmids, with circular plasmid vectors being particularly preferred. Suitable prokaryotic vectors are described, for example, in Sambrook et al., supra, Chapters 1–4.

A particularly preferred example of a vector according to the invention is the plasmid pHWS 88 which harbors a sucrose isomerase gene from *Protaminobacter rubrum* (with the sequence shown in SEQ ID NO:1) under the control of the regulatable tac promoter. The plasmid pHWS 88 was deposited on Dec. 16, 1993, at the Deutsche Sammlung von Mikroorganismen und Zellkulturen (DSM), Mascheroder Weg 1b, 38124 Braunschweig, Germany, under the deposit number DSM 8824 in accordance with the provisions of the Budapest Treaty.

In another preferred embodiment of the present invention, the vector according to the invention is a plasmid which is present in the host cell with a copy number of less than 10, particularly preferably with a copy number of 1 to 2 copies per host cell. Examples of vectors of this type are, on the one hand, chromosomal vectors such as, for example, bacteriophage λ or F plasmids. F plasmids which contain the sucrose isomerase gene can be prepared, for example, by transformation of an *E. coli* strain which contains an F plasmid with a transposon containing the sucrose isomerase gene, and subsequent selection for recombinant cells in which the transposon has integrated into the F plasmid. One example of a recombinant transposon of this type is the plasmid pHWS 118 which contains the transposon Tn 1721 Tet and was prepared by cloning a DNA fragment containing the sucrose isomerase gene from the above-described plasmid pHWS 88 into the transposon pJOE 105 (DSM 8825).

On the other hand, the vector according to the invention can also be a eukaryotic vector, for example a yeast vector (for example YIp, YEp, etc.) or a vector suitable for higher cells (for example a plasmid vector, viral vector, plant vector). Vectors of these types are familiar to the person skilled in the area of molecular biology so that details thereof need not be given here. Reference is made in this connection in particular to Sambrook et al., supra, Chapter 16.

The present invention further relates to a cell which is transformed with a DNA sequence according to the invention or a vector according to the invention. In one embodiment, this cell is a prokaryotic cell, preferably a Gram-negative prokaryotic cell, particularly preferably an enterobacterial cell. It is moreover possible on the one hand to use a cell which contains no sucrose isomerase gene of its own, such as, for example, *E. coli,* but it is also possible, on the other hand, to use cells which already contain such a gene on their chromosome, for example the microorganisms mentioned above as source of sucrose isomerase genes. Preferred examples of suitable prokaryotic cells are *E. coli, Protaminobacter rubrum* or *Erwinia rhapontici* cells. The transformation of prokaryotic cells with exogenous nucleic acid sequences is familiar to a person skilled in the area of molecular biology (see, for example, Sambrook et al., supra, Chapter 1–4).

In another embodiment of the present invention, the cell according to the invention may, however, also be a eukaryotic cell such as, for example, a fungal cell (for example yeast), an animal or a plant cell. Methods for the transformation or transfection of eukaryotic cells with exogenous nucleic acid sequences are likewise familiar to the person skilled in the area of molecular biology and need not be explained here in detail (see, for example, Sambrook et al., Chapter 16).

The invention also relates to a protein with a sucrose isomerase activity as defined above, which is encoded by a DNA sequence according to the invention. This protein preferably comprises (a) one of the amino-acid sequences shown in SEQ ID NO:4, SEQ ID NO:5, SEQ ID NO:6, SEQ ID NO:10, SEQ ID NO:12 or SEQ ID NO:14, where appropriate without the signal peptide region or (b) an amino-acid sequence which is at least 80% homologous with the sequences from (a).

The amino-acid sequence shown in SEQ ID NO:4 comprises the complete sucrose isomerase from *Protaminobacter rubrum.* The signal peptide extends from amino acid 1–33. The mature protein starts at amino acid 34. The amino-acid sequence shown in SEQ ID NO:5 comprises the N-terminal section of the sucrose isomerase from *Erwinia rhapontici.* The signal peptide extends from amino acid 1–36. The mature protein starts at amino acid 37. The amino-acid sequence shown in SEQ ID NO:6 comprises a section of the sucrose isomerase from the microorganism SZ 62. FIG. 1 compares the amino-acid sequences of the isomerases from *P. rubrum, E. rhapontici* and SZ 62.

Amino-acid sequence SEQ ID NO:10 comprises a variant of the isomerase from *P. rubrum.* Amino-acid sequence SEQ ID NO:12 comprises the complete isomerase from SZ 62. This enzyme has a high activity at 37° C. and produces only a very small proportion of monosaccharides. Amino-acid sequence SEQ ID NO:14 comprises a large part of the isomerase from MX-45. This enzyme produces about 85% trehalulose and 13% palatinose.

The protein according to the invention particularly preferably has an at least 90% homologous amino-acid sequence to conserved part-regions from the amino-acid sequences shown in SEQ ID NO:4, SEQ ID NO:5, SEQ ID NO:6, SEQ ID NO:13, SEQ ID NO:12 or SEQ ID NO:14, especially in part-regions from (a) amino acid 51–149, (b) amino acid 168–181, (c) amino acid 199–250, (d) amino acid 351–387 and/or (e) amino acid 390–420 of the amino-acid sequence shown in SEQ ID NO:4.

It is possible by means of the abovementioned DNA sequences, vectors, transformed cells and proteins to provide a sucrose isomerase activity in a simple manner without interfering additional enzymatic activities.

It is possible for this purpose on the one hand to obtain the sucrose isomerase by recombinant DNA technology as constituent of an extract from the host organism or in isolated and purified form (for example by expression in *E. coli*). This preferably purified and isolated sucrose isomerase enzyme can be used, for example, in immobilized form, for the industrial production of acariogenic sugars such as, for example, trehalulose and/or palatinose by reaction of sucrose in an enzyme reactor. The immobilization of enzymes is familiar to a skilled person and need not be described in detail here.

On the other hand, the production of acariogenic sugars from sucrose can also take place in a complete microorganism, preferably in immobilized form. Cloning of the abovementioned sucrose isomerase gene into an organism without or with reduced palatinose and/or trehalulose metabolism (that is to say in an organism which is unable significantly to degrade the abovementioned sugars) allows generation of a novel organism which, owing to the introduction of exogenous DNA, is able to produce acariogenic disaccharides with negligible formation of monosaccharides. Thus, suitable for introducing the sucrose isomerase gene is, on the one hand, an organism which is unable to utilize palatinose and/or trehalulose (for example *E. coli,* bacillus, yeast) and, on the other hand, an organism which would in principle be able to utilize palatinose and/or trehalulose but has reduced palatinose and/or trehalulose metabolism owing to undirected or directed mutation.

The term "reduced palatinose and/or trehalulose metabolism" means for the purpose of the present invention that a whole cell of the relevant organism produces, on utilization of sucrose as C source, acariogenic disaccharides but is able to utilize the latter to only a small extent in metabolism, for example by degrading them to monosaccharides. The organism preferably produces less than 2.5%, particularly preferably less than 2%, most preferably less than 1%, of glucose plus fructose based on the total of acariogenic disaccharides and monosaccharide degradation products at a temperature of 15–65° C., in particular of 25–55° C.

The present invention thus further relates to a cell which contains at least one DNA sequence coding for a protein with a sucrose isomerase activity, and has a reduced palatinose and/or trehalulose metabolism as defined above. A cell of this type produces larger proportions of the non-cariogenic disaccharides trehalulose and/or palatinose and reduced amounts of the interfering byproducts glucose and fructose.

It is possible in one embodiment of the present invention to reduce the palatinose and/or trehalulose metabolism by partial or complete inhibition of the expression of invertase and/or palatinase genes which are responsible for the intracellular degradation of palatinose and/or trehalulose. This inhibition of gene expression can take place, for example, by site-directed mutagenesis and/or deletion of the relevant genes. A site-directed mutation of the palatinase gene shown in SEQ ID NO:7 or of the palatinose hydrolase gene shown in SEQ ID NO:15 can take place, for example, by introduction of a vector which is suitable for homologous chromosomal recombination and which harbors a mutated palatinase gene, and selection for organisms in which such a recombination has taken place. The principle of selection by genetic recombination is explained in E. L. Winnacker, Gene und Klone, Eine Einführung in die Gentechnologie (1985), VCH-Verlagsgesellschaft Weinheim, Germany, pp. 320 et seq.

It is furthermore possible to obtain organisms according to the invention with reduced palatinose and/or trehalulose metabolism by non-specific mutagenesis from suitable starting organisms and selection for palatinase-deficient mutants. One example of a palatinase-deficient mutant of this type is the *Protaminobacter rubrum* strain SZZ 13 which was deposited on Mar. 29, 1994, at the Deutsche Sammlung von Mikroorganismen und Zellkulturen (DSM), Mascheroder Weg 1b, 38124 Braunschweig, Germany, under deposit number DSM 9121 in accordance with the provisions of the Budapest Treaty. This microorganism was prepared by non-specific mutagenesis of *P. rubrum* wild-type cells with N-methyl-N'-nitro-N-nitrosoguanidine and is distinguished in that it is no longer able to cleave the non-cariogenic sugars trehalulose and palatinose to glucose and fructose. Selection for such mutants can take place, for example, by using MacConkey palatinose media or minimal salt media with palatinose or glucose as sole C source. The mutants which are white on MacConkey palatinose medium (MacConkey Agar Base from Difco Laboratories, Detroit, Mich., USA (40 g/l) and 20 g/l palatinose) or which grow on minimal salt media with glucose as sole C source but not on corresponding media with palatinose as sole C source are identified as palatinase-deficient mutants.

The present invention furthermore relates to a method for isolating nucleic acid sequences which code for a protein with a sucrose isomerase activity, wherein a gene bank from a donor organism which contains a DNA sequence coding for a protein with a sucrose isomerase activity is set up in a suitable host organism, the clones of the gene bank are examined, and the clones which contain a nucleic acid coding for a protein with sucrose isomerase activity are isolated. The nucleic acids which are isolated in this way and code for sucrose isomerase can in turn be used for introduction into cells as described above in order to provide novel producer organisms of acariogenic sugars.

In this method, the chosen host organism is preferably an organism which has no functional genes of its own for palatinose metabolism, in particular no functional palatinase and/or invertase genes. A preferred host organism is *E. coli*. To facilitate characterization of palatinose-producing clones it is possible on examination of the clones in the gene bank for sucrose-cleaving clones and the DNA sequences which are contained therein and originate from the donor organism to be isolated and transformed in an *E. coli* strain which does not utilize galactose and which is used as screening strain for the clones in the gene bank.

On the other hand, the examination of the clones in the gene bank for DNA sequences which code for a protein with a sucrose isomerase activity can also take place using nucleic acid probes derived from the sequences SEQ ID NO:1, SEQ ID NO:2, SEQ ID NO:3, SEQ ID NO:9, SEQ ID NO:11 and SEQ ID NO:13 which code for the sucrose isomerase genes from *Protaminobacter rubrum, Erwinia rhapontici* and the isolate SZ 62. A DNA fragment obtained by PCR reaction with oligonucleotides I and II as primers, or the oligonucleotides III and/or IV, are particularly preferably used as probes.

The present invention further relates to a process for the production of non-cariogenic sugars, in particular trehalulose and/or palatinose, which comprises using for the production of the sugars (a) a protein with sucrose isomerase activity in isolated form, (b) an organism which is transformed with a DNA sequence which codes for protein with sucrose isomerase activity, or with a vector which contains at least one copy of this DNA sequence, (c) an organism which contains at least one DNA sequence coding for a protein with a sucrose isomerase activity, and has a reduced palatinose and/or trehalulose metabolism, and/or (d) an extract from such a cell or from such an organism.

The process is generally carried out by contacting the protein, the organism or the extract in a suitable medium with sucrose under conditions such that the sucrose is at least partly converted by the sucrose isomerase into acariogenic disaccharides. Subsequently, the acariogenic disaccharides are obtained from the medium or the organism and purified in a known manner.

In a preferred embodiment of this process, the organism, the protein or the extract is used in immobilized form. Proteins (in pure form or in extracts) are preferably immobilized by coupling of reactive side groups (for example $NH_2$ groups) to a suitable carrier. Immobilization of cells takes place, for example, in a sodium alginate/calcium chloride solution. A review of suitable methods for immobilizing cells and proteins is given, for example, in I. Chibata (Immobilized Enzymes, John Wiley and Sons, New York, London, 1978).

It is possible on use of a cell transformed with the sucrose isomerase gene to increase the rate of production of acariogenic sugars by comparison with known organisms by increasing the number of gene copies in the cell and/or by increasing the expression rate in a combination with strong promoters. It is furthermore possible by transformation of a cell which is unable or able to only a limited extent to utilize acariogenic sugars with the sucrose isomerase gene to produce a transformed cell with whose aid it is possible to obtain acariogenic sugars, in particular palatinose and/or trehalulose, without or with fewer byproducts.

On use of a microorganism with reduced palatinose and/or trehalulose metabolism, which already contains a functional sucrose isomerase gene, transformation with an exogenous sucrose isomerase gene is not essential but may be carried out to improve the yields.

Finally, the present invention also relates to a DNA sequence which codes for a protein with palatinase or palatinose hydrolase activity and comprises (a) one of the nucleotide sequences shown in SEQ ID NO:7 or SEQ ID NO:15, (b) a nucleotide sequence which corresponds to the sequence from (a) within the scope of the degeneracy of the genetic code or (c) a nucleotide sequence which hybridizes with the sequences from (a) and/or (b).

The invention further relates to a vector which contains at least one copy of the abovementioned DNA sequence and to a cell which is transformed with a DNA sequence or a vector as mentioned above. The invention likewise embraces a protein with palatinase activity which is encoded by a DNA sequence as indicated above and which preferably has one of the amino-acid sequences shown in SEQ ID NO:8 or SEQ ID NO:16.

The palatinase from *P. rubrum* shown in SEQ ID NO:8 differs from known sucrose-cleaving enzymes in that it cleaves the sucrose isomers which are not cleaved by known enzymes, in particular palatinose.

The amino [acid] sequence shown in SEQ ID NO:16 comprises a palatinose hydrolase from MX-45, which cleaves palatinose to form fructose and glucose. The gene coding for this enzyme is shown in SEQ ID NO:15 and is located in the genome of MX-45 on the 5' side of the isomerase gene shown in SEQ ID NO:13.

The invention is further described by the following sequence listings and figures:

SEQ ID NO:1 shows the nucleotide sequence of the gene coding for the sucrose isomerase from *Protaminobacter rubrum*. The sequence coding for the signal peptide terminates at nucleotide No. 99.

SEQ ID NO:2 shows the N-terminal section of the nucleotide sequence of the gene coding for the sucrose isomerase of *Erwinia rhapontici*. The sequence coding for the signal peptide terminates at the nucleotide with No. 108.

SEQ ID NO:3 shows a section of the nucleotide sequence of the gene coding for the sucrose isomerase from the isolate SZ 62.

SEQ ID NO:4 shows the amino-acid sequence of the sucrose isomerase from *Protaminobacter rubrum*.

SEQ ID NO:5 shows the N-terminal section of the amino-acid sequence of the sucrose isomerase from *Erwinia rhapontici*.

SEQ ID NO:6 shows a section of the amino-acid sequence of the sucrose isomerase from the isolate SZ 62.

SEQ ID NO:7 shows the nucleotide sequence for the palatinase gene from *Protaminobacter rubrum*.

SEQ ID NO:8 shows the amino-acid sequence of the palatinase from *Protaminobacter rubrum*.

SEQ ID NO:9 shows the nucleotide sequence of a variant of the sucrose isomerase gene from *P. rubrum*.

SEQ ID NO:10 shows the corresponding amino-acid sequence.

SEQ ID NO:11 shows the complete nucleotide sequence of the sucrose isomerase gene from SZ 62.

SEQ ID NO:12 shows the corresponding amino-acid sequence.

SEQ ID NO:13 shows most of the sucrose isomerase gene from *Pseudomonas mesoacidophila* (*MX*-45).

SEQ ID NO:14 shows the corresponding amino acid sequence.

SEQ ID NO:15 shows the palatinose hydrolase gene from *Pseudomonas mesoacidophila* (*MX*-45).

SEQ ID NO:16 shows the corresponding amino-acid sequence.

FIG. 1 shows a comparison of the amino-acid sequences of the sucrose isomerases from *Protaminobacter rubrum*, *Erwinia rhapontici* and the isolate ZS 62, FIG. 2 shows the cloning diagram for the preparation of the recombinant plasmid pHWS 118 which contains the sucrose isomerase gene on the transposon Tn 1721, FIG. 3 shows the diagram for the preparation of *E. coli* transconjugants which contain the sucrose isomerase gene of a F plasmid and FIG. 4 shows a comparison between the saccharides produced by *P. rubrum* wild-type cells and cells of the *P. rubrum* mutant SZZ 13.

The following examples serve to illustrate the present invention.

EXAMPLE 1

Isolation of the Sucrose Isomerase Gene from *Protaminobacter rubrum*

Complete DNA from the organism *Protaminobacter rubrum* (CBS 574, 77) was partially digested with Sau3A I. Collections of fragments with a size of about 10 kBp were obtained from the resulting fragment mixture by elution after fractionation by gel electrophoresis and were ligated into a derivative, which had been opened with BamHI, of the lambda EMBL4 vector derivative λ RESII (J. Altenbuchner, Gene 123 (1993), 63–68). A gene bank was produced by transfection of *E. coli* and transformation of the phages into plasmids according to the above reference. Screening of the kanamycin-resistant colonies in this gene bank was carried out with the radiolabeled oligonucleotide S214 which was derived from the sequence of the N terminus of the mature isomerase by hybridization:

```
S214:  5'-ATCCCGAAGTGGTGGAAGGAGGC-3'  (SEQ ID NO:21)
          T  A  A       A  A
```

Subsequently, the plasmid DNA was isolated from the colonies with a positive reaction after appropriate cultivation. After a restriction map had been drawn up, suitable subfragments were sequenced from a plasmid pKAT 01 obtained in this way, and thus the complete nucleotide sequence, which is shown in SEQ ID NO:1, of the DNA coding for isomerase was obtained. The amino-acid sequence derived therefrom corresponds completely to the peptide sequence of the mature isomerase obtained by sequencing (Edmann degradation). A cleavage site for SacI is located in the non-coding 3' region of this isomerase gene, and a cleavage site for HindIII is located in the non-coding 5' region. This makes it possible to subclone the intact isomerase gene into the vector pUCBM 21 (derivative of the vector pUC 12, Boehringer Mannheim GmbH, Mannheim, Germany) which had previously been cleaved with the said enzymes. The resulting plasmid was called pHWS 34.2 and confers on the *E. coli* cells harboring it the ability to synthesize sucrose isomerase.

A variant of the sucrose isomerase gene from *P. rubrum* has the nucleotide sequence shown in SEQ ID NO:9.

EXAMPLE 2

Cloning and Expression of the Sucrose Isomerase from *P. rubrum* in *E. coli*

1. Preparation of the Plasmid pHWS88

The non-coding 5' region of the sucrose isomerase gene was deleted from the plasmid pHWS 34.2, using an oligonucleotide S434 with the sequence 5'-CGGAATTCTTATGCCCCGTCAAGGA-3' (SEQ ID NO:22), with simultaneous introduction of an EcoRI cleavage site (GAATTC). The isomerase gene derivative obtained in this way was treated with BstE II, the protruding BstE II end was digested off with S1 nuclease and subsequently digestion with EcoRI was carried out. The isomerase gene treated in this way was cloned into the vector pBTacI (Boehringer Mannheim GmbH, Mannheim, Germany) which had been pretreated with EcoRI and SmaI. The resulting vector pHWS 88 (DSM 8824) contains the modified isomerase gene with a preceding EcoRI restriction site in front of the ATG start codon, and the 3' region of the isomerase gene up to the S1-truncated BstE II cleavage site.

On induction with IPTG, this vector confers on the cells harboring this plasmid the ability to produce isomerase and resistance to ampicillin (50 to 100 μg/ml). Preferably used for producing isomerase are E. coli host cells which overproduce the lac repressor.

2. Preparation of the Plasmid pHWS118::Tn1721Tet

The gene cassette for the sucrose mutase was incorporated into a transposon.

This took place by cloning an SphI/HindIII DNA fragment from the plasmid pHWS88, which harbors the sucrose mutase gene under the control of the tac promoter, into the plasmid pJOE105 on which the transposon Tn 1721 is located. The plasmid pJOE105 was deposited on Dec. 16, 1993, at the DSM under the deposit number DSM 8825 in accordance with the provisions of the Budapest Treaty. The resulting plasmid pHWS118, on which the sucrose mutase gene is under the control of the regulatable tac promoter, was used to transform a E. coli strain containing an F' plasmid. FIG. 2 shows the cloning diagram for the preparation of pHWS 118 from pHWS88 and pJOE 105.

E. coli transconjugants containing the sucrose mutase gene were prepared as described in the diagram in FIG. 3. For this purpose, firstly the F'-harboring E. coli strain CSH36 (J. H. Miller, Experiments in Molecular Genetics, Cold Spring Harbor Laboratory (1972), p. 18), which carries the Lac+ phenotype mediated by the F' plasmid, was crossed with the E. coli strain JM108 which is resistant to nalidixic acid (Sambrook et al., supra, p. A9–A13). Selection on minimal medium to which lactose, proline and nalidixic acid were added resulted in an F'-Lac-harboring transconjugant. This was additionally transformed with the Iq plasmid FDX500 (Brinkmann et al., Gene 85 (1989), 109–114) in order to permit control of the sucrose mutase gene by the tac promoter.

The transconjugant prepared in this way was transformed with the transposon plasmid pHWS118 harboring the sucrose mutase gene. For selection of transconjugants, crossing into the streptomycin-resistant E. coli strain HB101 (Boyer and Roulland-Dussoix, J. Mol. Biol 41 (1969), 459–472) was carried out. Transfer of the tetracycline resistance mediated by the transposon was possible only after transposition of the modified Tn1721Tet from the plasmid pHWS118, which is not capable of conjugation or mobilization, to the F' plasmid which is capable of conjugation. Transmission of the F' plasmid with the modified transposon in HB101 was selected on LB plates containing streptomycin and tetracycline, and retested on ampicillin and nalidixic acid plates.

3. Expression of the Sucrose Isomerase in E. coli

Examination of the enzyme production by such F' plasmid-harboring E. coli cells showed that it was possible to produce sucrose mutase protein. F' plasmid-containing HB101 cells which harbored no additional Lac repressor plasmid (for example K1/1 or K1/10) produced sucrose mutase protein in identical amounts with and without the inducer isopropyl β-D-thiogalactoside (IPTG). The productivities of three transconjugants K1/1, K1/10 and K1/4 are shown in following Table 1.

TABLE 1

Surose mutase activity in E. coli HB101 (F'::Tn1721 [Mutase])

| Strain | U/mg mutase after 4 hours without induction | U/mg mutase after 4 hours induction with 50 μM IPTG |
|---|---|---|
| K1/1 | 1.0 | 1.2 |
| K1/10 | 0.9 | 1.1 |
| K1/4 | 0 | 1.6 |

It was possible to observe normal growth of the E. coli cells during production of sucrose mutase protein.

Introduction of the sucrose mutase gene into the F' plasmid in the presence of the repressor-encoded plasmid pFDX500 (see transconjugants K1/4) made it possible to control enzyme production with the inducer IPTG. Whereas no enzymatic activity was measured without IPTG, production of about 1.6 U/mg sucrose mutase protein was obtainable after induction for 4 hours.

No adverse effect on cell growth was observable. The plasmid-harboring E. coli cells reached a density of about 3 $OD_{600}$ after induction for 4 hours.

Up to 1.6 U/mg sucrose mutase activity were measured in transformed E. coli. The synthetic performance is comparable to that of P. rubrum. Analysis of the produced enzyme by SDS gel electrophoresis provides no evidence of inactive protein aggregates. The band of the sucrose mutase protein was only weakly visible with Coomassie staining and was detectable clearly only in a Western blot. It was possible to correlate the strength of the protein band and the measured enzymatic activity in the production of sucrose mutase in E. coli.

EXAMPLE 3

Isolation of the Sucrose Isomerase Gene from Erwinia rhapontici

A gene bank was produced by restriction cleavage of the complete DNA from Erwinia rhapontici (NCPPB 1578) in the same way as described in Example 1.

Using the primer mixtures

```
5'-TGGTGGAAAGAAGCTGT-3'  (SEQ ID NO:23)
         G  G
and
5'-TCCCAGTTCAGGTCCGGCTG-3'  (SEQ ID NO:24)
         A
```

PCR amplification resulted in A a DNA fragment with whose aid it is possible to identify colonies containing the mutase gene by hybridization.

In this way, a positive clone pSST2023 which contains a fragment, 1305 nucleotides long, of the Erwinia isomerase gene was found. The nucleotide sequence of this fragment is depicted in SEQ ID NO:2.

Sequence comparison with the Protaminobacter gene reveals an identity of 77.7% and a similarity of 78% for the complete gene section including the signal peptide region, and an identity of 83.4% and a similarity of 90.3% at the amino-acid level.

The sequence differences are mainly concentrated in the signal peptide region. For this reason, only the enzyme-encoding region responsible for the actual mutase activity, without the signal peptide, should be considered for comparison. From these viewpoints, the identity or similarity at the nucleotide level emerges as 79%. Comparison of the amino-acid sequences (FIG. 1) in this section shows 87.9% identical amino acids. Of 398 amino acids (this corresponds to 71% of the complete enzyme) in the Erwinia mutase, 349 are the same as in Protaminobacter. 25 of 48 exchanged amino acids show strong similarity so that the overall similarity at the AA level emerges as 94%. The AA exchanges are mainly concentrated in the region between amino acid 141 and 198. In front of this region there is a sequence of 56 conserved amino acids. Other sections also exhibit particularly high conservation (see FIG. 1).

These data show that, for the section cloned and sequenced to date, overall there is very extensive conservation of the two mutases from Erwinia and Protaminobacter.

Identity of the Cloned Mutase Gene from Erwinia

The probe chosen for a rehybridization experiment with genomic Erwinia DNA was the SspI/EcoRI fragment, which is about 500 bp in size, from pSST2023. This fragment was used, after digoxigenin labeling, for hybridization with Erwinia DNA with high stringency (68° C.). Complete Erwinia DNA cut with SspI/EcoRI showed a clear hybridization signal with the expected size of about 500 bp. Erwinia DNA cut only with SspI showed a hybridization signal of about 2 kb.

It was possible to verify by the successful rehybridization of pSST2023 with genomic Erwinia DNA that the mutase region cloned into pSST2023 originates from *Erwinia rhapontici*.

Cloning of the C-Terminal Part-Fragment of the Erwinia Mutase

The N-terminal part-fragment of the Erwinia mutase gene which has been cloned to date has a size of 1.3 kb and has the nucleotide sequence shown in SEQ ID NO:2. Since it can be assumed that the complete Erwinia gene is virtually identical in size to the known Protaminobacter gene (1.8 kb), a section of about 500 bp is missing from the C-terminal region of the Erwinia gene.

The SspI fragment which is about 2 kb in size from the complete Erwinia DNA was selected for cloning of the Erwinia C-terminus. In a Southern blot, this fragment provides a clear signal with a digoxigenin-labeled DNA probe from pSST2023. This 2 kb SspI fragment overlaps by about 500 bp at the 3' end with the region already cloned in pSST2023. Its size ought to be sufficient for complete cloning of the missing gene section of about 500 bp. The digoxigenin-labeled fragment probe SspI/EcoRI from pSST2023 is suitable for identifying clones which are sought.

EXAMPLE 4

Preparation of a Protaminobacter Palatinase-Deficient Mutant

Cells of *Protoaminobacter rubrum* (CBS 547, 77) were mutagenized with N-methyl-N'-nitro-N-nitroso-guanidine by the method of Adelberg et al. (Biochem. Biophys. Research Commun. 18 (1965), 788) as modified by Miller, J., (Experiments in Molecular Genetics, Cold Spring Harbor Laboratory, 125–179 (1972)). Palatinase-deficient mutants were selected using MacConkey palatinose medium (MacConkey Agar Base (Difco Laboratories, Detroit, Mich., USA), 40 g/l with the addition of 20 g/l palatinose, sterilized by filtration, 25 mg/l kanamycin) and minimal salt media (10.5 g of $K_2HPO_4$, 4.5 g of $KH_2PO_4$, 1 g of $(NH_4)_2SO_4$, 0.5 g of sodium citrate. 2 $H_2O$, 0.1 g of $MgSO_4.7H_2O$), 1 mg of thiamine, 2 g of palatinose or glucose, 25 mg of kanamycin and 15 g of agar per liter, pH 7.2). Mutants of *P. rubrum* which are white on MacConkey palatinose medium or grow on minimal salt medium with glucose in contrast to the same medium with palatinose are identified as palatinase-deficient mutants. The enzyme activity of cleaving palatinose to glucose and fructose (palatinase activity) cannot, in contrast to the wild-type, be detected in cell extracts from these mutants. On cultivation of these cells in minimal salt medium with 0.2% sucrose as sole C source there is, in contrast to the wild-type cells in which palatinose can be detected only transiently in the time from 4 to 11 hours after starting the culture, a detectable continuous accumulation of palatinose (isomaltulose). Overnight cultures in the same medium contain no palatinose in the case of the wild-type cells but contain >0.08% palatinose in the case of the mutant SZZ 13 (DSM 9121) prepared in this way (see FIG. 4).

EXAMPLE 5

Immobilization of Microorganism Cells

Cells are rinsed off a subculture of the appropriate strain using 10 ml of a sterile nutrient substrate composed of 8 kg of concentrated juice from a sugar factory (dry matter content=65%), 2 kg of corn steep liquor, 0.1 kg of $(NH_4)_2HPO_4$ and 89.9 kg of distilled water, pH 7.2. This suspension is used as inoculum for preculture in 1 l flasks containing 200 ml of nutrient solution of the above composition in shaking machines. After an incubation time of 30 hours at 29° C., 10 flasks (total contents 2 l) are used to inoculate 18 l of nutrient solution of the above composition in a 30 l small fermenter, and fermentation is carried out at 29° C. and a stirring speed of 350 rpm introducing 20 l of air per minute.

After organism counts above $5 \times 10^9$ organisms per ml are reached, the fermentation is stopped and the cells are harvested from the fermenter solution by centrifugation. The cells are then suspended in a 2% strength sodium alginate solution and immobilized by dropwise addition of the suspension to a 2% strength calcium chloride solution. The resulting immobilizate beads are washed with water and can be stored at +4° C. for several weeks.

Cells of the palatinase-deficient mutant SZZ 13 (DSM 9121) show better catalytic properties in respect of their product composition than do comparable cells from the known microorganisms *Protaminobacter rubrum* (CBS 547, 77) and *Erwinia rhapontici* (NCPPB 1578).

Whole cells and crude extracts of SZZ 13, and an immobilizate of SZZ 13 in calcium alginate prepared as above, were evaluated in respect of product composition in an activity assay. Before the actual activity assay, the immobilizate was swollen in 0.1 mol/l potassium phosphate buffer, pH 6.5.

The activity measurements at 25° C. revealed that no fructose and glucose were found with the mutant SZZ 13, while with *P. rubrum* wild-type cells 2.6% fructose and glucose (based on the total of mono- and disaccharides) were found in whole cells and 12.0% were found in the crude extract. In the case of *E. rhapontici*, 4% glucose and fructose were found in whole cells, and 41% in the crude extract.

EXAMPLE 6

Isolation of the Sucrose Isomerase Gene from Other Microorganisms

Partial digestion of genomic DNA from the isolate SZ62 (Enterobacter spec.), the organism *Pseudomonas mesoaci-*

*dophila* (*MX*-45) or from another microorganism and insertion of the resulting fragments into suitable *E. coli* vectors and transformation result in a gene bank whose clones contain genomic sections between 2 and 15 kb of the donor organism.

Those *E. coli* cells which harbor these plasmids and which display a red coloration of the colony are selected by plating on McConkey palatinose medium. The plasmid DNA contained in these cells is transferred into an *E. coli* mutant which is unable to grow on galactose as sole C source (for example ED 8654, Sambrook et al., supra, pages A9–A13).

This transformed cell line is able to identify palatinose producers in the gene bank which has been prepared as described above from DNA of the donor organism.

To identify the palatinose-producing clones which are sought, the cells of the gene bank are isolated and cultured on minimal salt media containing galactose and sucrose. After replica plating of the colonies on plates containing the same medium, the cells are killed by exposure to toluene vapor. Subsequently, cells of the screening strain are spread as lawn in minimal salt soft agar without added C source over the colonies of the gene bank and incubated. Significant growth of the cells of the screening strain appears only at the location of cells in the gene bank which have produced palatinose. The isomerase content emerges on testing the cells of the replica control.

These *E. coli* clones identified in this way are unable to grow on palatinose as sole C source in the medium, show no ability to cleave sucrose in a test on whole cells or on cell extracts, but on cultivation under these conditions and without addition of sucrose to the medium produce palatinose.

Alternatively, isomerase clones can also be identified using a PCR fragment prepared by the procedure of Example 3.

Use of plasmid DNA from the *E. coli* clones identified in this way as probes for hybridization on filters with immobilized DNA from the donor organism allows the gene regions which harbor isomerase genes to be detected and specifically made available.

A clone which contains the nucleotide sequence shown in SEQ ID NO:3, with the amino-acid sequence which is derived therefrom and shown in SEQ ID NO:6, was identified in this way. In the same way an isomerase clone from DNA of the bacterial strain *Pseudomonas mesoacidophila* MX-45 (FERM 11808) was found.

The complete nucleotide sequence and amino-acid sequence of the sucrose isomerase from SZ 62 are depicted in SEQ ID NO:11 and 12. A large part of the nucleotide sequence and amino-acid sequence of the sucrose isomerase from MX-45 are depicted in SEQ ID NO:13 and 14.

EXAMPLE 7

Cloning of a Palatinase Gene

The *Protaminobacter rubrum* gene bank prepared in Example 1 was screened with the radiolabeled oligonucleotide mixture S433 which was derived from the sequence of the N-terminus of the isolated palatinase and had the sequence CA(G,A)TT(C,T)GG(T,C)TA(C,T)GG-3' (SEQ ID NO:25).

A positive clone was found, and a plasmid named pKAT 203 was isolated therefrom.

*E. coli* cells which harbor the plasmid PKAT 203 are able to metabolize palatinose. The cleavage of palatinose to glucose and fructose which is detectable in the activity assay suggests that there is a "palatinase".

It is possible by sequencing pKAT203 DNA with the oligonucleotide S433 as primer to obtain a DNA sequence from which it was possible to read off, after translation into amino-acid sequence data, the N-terminal amino acids known to us. An open reading frame was obtained by a subsequent sequencing step.

Determination of the Sequence of the "Palatinase" Gene

For further sequencing of the "palatinase" gene, part-fragments from the plasmid PKAT 203 were selected on the basis of the restriction map and subcloned in the M13 phage system, and a sequencing of the single-stranded phage DNA was carried out with the universal primer 5'-GTTTTCCCAGTCACGAC-3' (SEQ ID NO:26).

Combination of the resulting DNA sequence data for the individual fragments taking account of overlapping regions allows a continuous reading frame of 1360 base pairs to be determined for the "palatinase" (SEQ ID NO:7).

Translation of this DNA sequence into amino-acid data reveals a protein with 453 amino acids (SEQ ID NO:8) and a molecular weight, which can be deduced therefrom, of about 50,000 Da. This is consistent with the finding that a protein fraction which had a band at about 48,000 Da in the SDS gel was obtainable by concentration of the "palatinase" activity. In the native gel, the palatinose-cleaving activity was attributable to a band with a size of about 150,000 Da.

Comparisons of Homology with Other Known Proteins

Comparison of the amino-acid sequence derivable from the DNA sequence with data stored in a gene bank (SwissProt) revealed a homology with melibiase from *E. coli* (MelA) (in two parts: identity 32%).

EXAMPLE 8

Cloning of a Palatinose Hydrolase Gene from *P. mesoacidophila* MX-45

A gene with the nucleotide sequence shown in SEQ ID NO:15 was isolated from the gene bank prepared from the microorganism *P. mesoacidophila* MX-45 in Example 6. This gene codes for a protein with the amino-acid sequence shown in SEQ ID NO:16. The protein is a palatinose hydrolase which catalyzes the cleavage of palatinose to form fructose and glucose.

SEQ ID NO. 1

NAME: Pr Isomerase    LENGTH: 1890 bases

DESCRIPTION: Protaminobacter rubrum: Isomerase

* S E Q U E N C E *

```
1    ATGCCCCGTC AAGGATTGAA AACTGCACTA GCGATTTTTC TAACCACATC ATTATGCATC
61   TCATGCCAGC AAGCCTTCGG TACGCAACAA CCCTTGCTTA ACGAAAAGAG TATCGAACAG
121  TCGAAAACCA TACCTAAATG GTGGAAGAAG GCTGTTTTTT ATCAGGTGTA TCCGCGCTCC
181  TTTAAAGACA CCAACGGAGA TGGCATCGGG GATATTAACG GCATCATAGA AAAATTAGAC
241  TATCTAAAAG CCTTGGGGAT TGATGCCATT TGGATCAACC CACATTATGA TTCTCCGAAC
301  ACGGATAATG GTTACGATAT ACGTGATTAT CGAAAAATCA TGAAAGAATA TGGCACGATG
361  GAGGATTTTG ACCGCCTGAT TTCTGAAATG AAAAAACGGA ATATGCGGTT GATGATTGAT
421  GTGGTCATCA ACCACACCAG CGATCAAAAC GAATGGTTTG TTAAAAGTAA AAGCAGTAAG
481  GATAATCCTT ATCGCGGCTA TTATTTCTGG AAAGATGCTA AGAAGGGCA GGCGCCTAAT
541  AATTACCCTT CATTCTTTGG TGGCTCGGCG TGGCAAAAAG ATGAAAAGAC CAATCAATAC
601  TACCTGCACT ATTTTGCTAA ACAACAGCCT GACCTAAACT GGGATAATCC CAAAGTCCGT
661  CAAGATCTTT ATGCAATGTT ACGTTTCTGG TTAGATAAAG GCGTGTCTGG TTTACGTTTT
721  GATACGGTAG CGACCTACTC AAAAATTCCG GATTTCCCAA ATCTCACCCA ACAACAGCTG
781  AAGAATTTTG CAGCGGAGTA TACCAAGGGC CTAATATTC ATCGTTACGT CAATGAAATG
841  AATAAAGAGG TCTTGTCTCA TTACGACATT GCGACTGCCG GTGAAATCTT TGGCGTACCC
901  TTGGATCAAT CGATAAAGTT CTTCGATCGC CGCCGTGATG AGCTGAACAT TGCATTTACC
961  TTTGACTTAA TCAGACTCGA TCGAGACTCT GATCAAAGAT GGCGTCGAAA AGATTGGAAA
1021 TTGTCGCAAT TCCGGCAGAT CATCGATAAC GTTGACCGTA CTGCAGGAGA ATATGGTTGG
1081 AATGCCTTCT TCTTGGATAA CCACGACAAT CCGCGCGCTG TCTCGCACTT TGGCGATGAT
1141 GATCGCCCAC AATGGCGTGA GCCATCGGCT AAAGCGCTTG CAACCTTGAC GCTGACTCAA
1201 CGAGCAACAC CTTTTATTTA TCAAGGTTCA GAATTGGGCA TGACCAATTA CCCGTTTAAA
1261 GCTATTGATG AATTCGATGA TATTGAGGTG AAAGGTTTTT GGCATGACTA CGTTGAGACA
1321 GGAAAGGTCA AGCCGACGA GTTCTTGCAA AATGTACGCC TGACGAGCAG GGATAACAGC
1381 CGGACGCCGT TCCAATGGGA TGGGAGCAAA AATGCAGGAT TCACGAGCGG AAAACCTTGG
1441 TTCAAGGTCA ACCCAAACTA CCAGGAAATC AATGCAGTAA GTCAAGTCAC ACAACCCGAC
1501 TCAGTATTTA ACTATTATCG TCAGTTGATC AAGATAAGGC ATGACATCCC GGCACTGACC
1561 TATGGTACAT ACACCGATTT GGATCCTGCA AATGATTCGG TCTACGCCTA TACACGCAGC
1621 CTTGGGGCGG AAAAATATCT TGTTGTTGTT AACTTCAAGG AGCAAATGAT GAGATATAAA
1681 TTACCGGATA ATTTATCCAT TGAGAAAGTG ATTATAGACA GCAACAGCAA AAACGTGGTG
1741 AAAAAGAATG ATTCATTACT CGAGCTAAAA CCATGGCAGT CAGGGGTTTA TAAAACTAAA
1801 TCAATAAATC TCATAGTCAC GCCAAATAAT GTAAATATAT TGAAACTATT AAAACCGGCA
1861 TTTTATGCCG GTTTTTTTAG CGCAAAATAG
```

SEQ ID NO. 2

DESCRIPTION: E. rhapontici isomerase

LENGTH: 1305 bases

* S E Q U E N C E *

```
   1 ATGTCCTCTC AAGGATTGAA AACGGCTNTC GCTATTTTTC TTGCAACCAC TTTTTCTGCC
  61 ACATCCTATC AGGCCTGCAG TGCCNNNCCA GATACCGCCC CCTCACTCAC CGTTCAGCAA
 121 TCAAATGCCC TGCCCACATG GTGGAAGCAG GCTGTTTTTT ATCAGGTATA TCCACGCTCA
 181 TTTAAAGATA CGAATGGGGA TGGCATTGGG GATTTAAACG GTATTATTGA GAATTTAGAC
 241 TATCTGAAGA AACTGGGTAT TGATGCGATT TGGATCAATC CACATTACGA TTCGCCGAAT
 301 ACGGATAATG GTTATGACAT CCGGGATTAC CGTAAGATAA TGAAAGAATA CGGTACGATG
 361 GAAGACTTTG ACCGTCTTAT TTCAGAAATG AAGAAACGCA ATATGCGTTT GATGATTGAT
 421 ATTGTTATCA ACCACACCAG CGATCAGCAT GCCTGGTTTG TTCAGAGCAA ATCGGGTAAG
 481 AACAACCCCT ACAGGGACTA TTACTTCTGG CGTGACGGTA AGGATGGCCA TGCCCCCAAT
 541 AACTATCCCT CCTTCTTCGG TGGCTCAGCC TGGGAAAAAG ACGATAAATC AGGCCAGTAT
 601 TACCTCCATT ACTTTGCCAA ACAGCAACCC GACCTCAACT GGGACAATCC CAAAGTCCGT
 661 CAAGACCTGT ATGACATGCT CCGCTTCTGG TTAGATAAAG GCGTTTCTGG TTTACGCTTT
 721 GATACCGTTG CCACCTACTC GAAAATCCCG AACTTCCCTG ACCTTAGCCA ACAGCAGTTA
 781 AAAAATTTCG CCGAGGAATA TACTAAAGGT CCTAAAATTC ACGACTACGT GAATGAAATG
 841 AACAGAGAAG TATTATCCCA CTATGATATC GCCACTGCGG GGGAAATATT TGGGGTTCCT
 901 CTGGATAAAT CGATTAAGTT TTTCGATCGC CGTAGAAATG AATTAAATAT AGCGTTTACG
 961 TTTGATCTGA TCAGGCTCGA TCGTGATGCT GATGAAAGAT GGCGGCGAAA AGACTGGACC
1021 CTTTCGCAGT TCCGAAAAAT TGTCGATAAG GTTGACCAAA CGGCAGGAGA GTATGGGTGG
1081 AATGCCTTTT TCTTAGACAA TCACGACAAT CCCCGCGCGG TTTCTCACTT TGGTGATGAT
1141 CGACCACAAT GGCGCGAGCA TGCGGCGAAA GCACTGGCAA CATTGACGCT GACCCAGCGT
1201 GCAACGCCGT TTATCTATCA GGGTTCAGAA CTCGGTATGA CCAATTATCC CTTTAAAAAA
1261 ATCGATGATT TCGATGATGT AGAGGTGAAA GGTTTTTGGC AAGAC
```

SEQ ID NO. 3

NAME:     SZISO1.DNA     LENGTH:   471 bases

DESCRIPTION:  SZ62 isomerase

* S E Q U E N C E *

```
   1 GTTTTTTATC AGATCTATCC TCGCTCATTT AAAGACACCA ATGATGATGG CATTGGCGAT
  61 ATTCGCGGTA TTATTGAAAA GCTGGACTAT CTGAAATCGC TCGGTATTGA CGCTATCTGG
 121 ATCAATCCCC ATTACGACTC TCCGAACACC GATAACGGCT ATGACATCAG TAATTATCGT
 181 CAGATAATGA AAGAGTATGG CACAATGGAG GATTTTGATA GCCTTGTTGC CGAAATGAAA
 241 AAACGAAATA TGCGCTTAAT GATCGACGTG GTCATTAACC ATACCAGTGA TCAACACCCG
 301 TGGTTTATTC AGAGTAAAAG CGATAAAAAC AACCCTTATC GTGACTATTA TTTCTGGCGT
 361 GACGGAAAAG ATAATCAGCC ACCTAATAAT TACCCCTCAT TTTTCGGCGG CTCGGCATGG
 421 CAAAAAGATG CAAAGTCAGG ACAGTACTAT TTACACTATT TTGCCAGACA G
```

SEQ ID NO. 4

NAME:     Pr Isomerase     LENGTH:  1890 bases or 629
                                    amino acids DESCRIPTION:  Protaminobacter rubrum: Isomerase -continued

\*\*\* S E Q U E N C E \*\*\*

```
   1 ATG CCC CGT CAA GGA TTG AAA ACT GCA CTA GCG ATT TTT CTA ACC ACA
     Met Pro Arg Gln Gly Leu Lys Thr Ala Leu Ala Ile Phe Leu Thr Thr

49 TCA TTA TGC ATC TCA TGC CAG CAA GCC TTC GGT ACG CAA CAA CCC TTG
     Ser Leu Cys Ile Ser Cys Gln Gln Ala Phe Gly Thr Gln Gln Pro Leu

97 CTT AAC GAA AAG AGT ATC GAA CAG TCG AAA ACC ATA CCT AAA TGG TGG
     Leu Asn Glu Lys Ser Ile Glu Gln Ser Lys Thr Ile Pro Lys Trp Trp

145 AAG GAG GCT GTT TTT TAT CAG GTG TAT CCG CGC TCC TTT AAA GAC ACC
     Lys Glu Ala Val Phe Tyr Gln Val Tyr Pro Arg Ser Phe Lys Asp Thr

193 AAC GGA GAT GGC ATC GGG GAT ATT AAC GGC ATC ATA GAA AAA TTA GAC
     Asn Gly Asp Gly Ile Gly Asp Ile Asn Gly Ile Ile Glu Lys Leu Asp

241 TAT CTA AAA GCC TTG GGG ATT GAT GCC ATT TGG ATC AAC CCA CAT TAT
     Tyr Leu Lys Ala Leu Gly Ile Asp Ala Ile Trp Ile Asn Pro His Tyr

289 GAT TCT CCG AAC ACG GAT AAT GGT TAC GAT ATA CTG GAT TAT CGA AAA
     Asp Ser Pro Asn Thr Asp Asn Gly Tyr Asp Ile Arg Asp Tyr Arg Lys

337 ATC ATG AAA GAA TAT GGC ACG ATG GAG GAT TTT GAC CGC CTG ATT TCT
     Ile Met Lys Glu Tyr Gly Thr Met Glu Asp Phe Asp Arg Leu Ile Ser

385 GAA ATG AAA AAA CGG AAT ATG CGG TTG ATG ATT GAT GTG GTC ATC AAC
     Glu Met Lys Lys Arg Asn Met Arg Leu Met Ile Asp Val Val Ile Asn

433 CAC ACC AGC GAT CAA AAC GAA TGG TTT GTT AAA AGT AAA AGC AGT AAG
     His Thr Ser Asp Gln Asn Glu Trp Phe Val Lys Ser Lys Ser Ser Lys

481 GAT AAT CCT TAT CGC GGC TAT TAT TTC TGG AAA GAT GCT AAA GAA GGG
     Asp Asn Pro Tyr Arg Gly Tyr Tyr Phe Trp Lys Asp Ala Lys Glu Gly

529 CAG GCG CCT AAT AAT TAC CCT TCA TTC TTT GGT GGC TCG GCG TGG CAA
     Gln Ala Pro Asn Asn Tyr Pro Ser Phe Phe Gly Gly Ser Ala Trp Gln

577 AAA GAT GAA AAG ACC AAT CAA TAC TAC CTG CAC TAT TTT GCT AAA CAA
     Lys Asp Glu Lys Thr Asn Gln Tyr Tyr Leu His Tyr Phe Ala Lys Gln

625 CAG CCT GAC CTA AAC TGG GAT AAT CCC AAA GTC CGT CAA GAT CTT TAT
     Gln Pro Asp Leu Asn Trp Asp Asn Pro Lys Val Arg Gln Asp Leu Tyr

673 GCA ATG TTA CGT TTC TGG TTA GAT AAA GGC GTG TCT GGT TTA CGT TTT
     Ala Met Leu Arg Phe Trp Leu Asp Lys Gly Val Ser Gly Leu Arg Phe

721 GAT ACG GTA GCG ACC TAC TCA AAA ATT CCG GAT TTC CCA AAT CTC ACC
     Asp Thr Val Ala Thr Tyr Ser Lys Ile Pro Asp Phe Pro Asn Leu Thr

769 CAA CAA CAG CTG AAG AAT TTT GCA GCG GAG TAT ACC AAG GGC CCT AAT
     Gln Gln Gln Leu Lys Asn Phe Ala Ala Glu Tyr Thr Lys Gly Pro Asn

817 ATT CAT CGT TAC GTC AAT GAA ATG AAT AAA GAG GTC TTG TCT CAT TAC
     Ile His Arg Tyr Val Asn Glu Met Asn Lys Glu Val Leu Ser His Tyr

865 GAC ATT GCG ACT GCC GGT GAA ATC TTT GCC GTA CCC TTG GAT CAA TCG
     Asp Ile Ala Thr Ala Gly Glu Ile Phe Ala Val Pro Leu Asp Gln Ser

913 ATA AAG TTC TTC GAT CGC CGC CGT GAT GAG CTG AAC ATT GCA TTT ACC
     Ile Lys Phe Phe Asp Arg Arg Arg Asp Glu Leu Asn Ile Ala Phe Thr

961 TTT GAC TTA ATC AGA CTC GAT CGA GAC TCT GAT CAA AGA TGG CGT CGA
     Phe Asp Leu Ile Arg Leu Asp Arg Asp Ser Asp Gln Arg Trp Arg Arg

1009 AAA GAT TGG AAA TTG TCG CAA TTC CGG CAG ATC ATC GAT AAC GTT GAC
     Lys Asp Trp Lys Leu Ser Gln Phe Arg Gln Ile Ile Asp Asn Val Asp

1057 CGT ACT GCA GGA GAA TAT GGT TGG AAT GCC TTC TTC TTG GAT AAC CAC
     Arg Thr Ala Gly Glu Tyr Gly Trp Asn Ala Phe Phe Leu Asp Asn His

1105 GAC AAT CCG CGC GCT GTC TCG CAC TTT GGC GAT GAT GAT CGC CCA CAA
     Asp Asn Pro Arg Ala Val Ser His Phe Gly Asp Asp Asp Arg Pro Gln

1153 TGG CGT GAG CCA TCG GCT AAA GCG CTT GCA ACC TTG ACG CTG ACT CAA
     Trp Arg Glu Pro Ser Ala Lys Ala Leu Ala Thr Leu Thr Leu Thr Gln

1201 CGA GCA ACA CCT TTT ATT TAT CAA GGT TCA GAA TTG GGC ATG ACC AAT
     Arg Ala Thr Pro Phe Ile Tyr Gln Gly Ser Glu Leu Gly Met Thr Asn
```

```
1249 TAC CCG TTT AAA GCT ATT GAT GAA TTC GAT GAT ATT GAG GTG AAA GGT
    Tyr Pro Phe Lys Ala Ile Asp Glu Phe Asp Asp Ile Glu Val Lys Gly

1297 TTT TGG CAT GAC TAC GTT GAG ACA GGA AAG GTC AAA GCC GAC GAG TTC
    Phe Trp His Asp Tyr Val Glu Thr Gly Lys Val Lys Ala Asp Glu Phe

1345 TTG CAA AAT GTA CGC CTG ACG AGC AGG GAT AAC AGC CGG ACG CCG TTC
    Leu Gln Asn Val Arg Leu Thr Ser Arg Asp Asn Ser Arg Thr Pro Phe

1393 CAA TGG GAT GGG AGC AAA AAT GCA GGA TTC ACG AGC GGA AAA CCT TGG
    Gln Trp Asp Gly Ser Lys Asn Ala Gly Phe Thr Ser Gly Lys Pro Trp

1441 TTC AAG GTC AAC CCA AAC TAC CAG GAA ATC AAT GCA GTA AGT CAA GTC
    Phe Lys Val Asn Pro Asn Tyr Gln Glu Ile Asn Ala Val Ser Gln Val

1489 ACA CAA CCC GAC TCA GTA TTT AAC TAT TAT CGT CAG TTG ATC AAG ATA
    Thr Gln Pro Asp Ser Val Phe Asn Tyr Tyr Arg Gln Leu Ile Lys Ile

1537 AGG CAT GAC ATC CCG GCA CTG ACC TAT GGT ACA TAC ACC GAT TTG GAT
    Arg His Asp Ile Pro Ala Leu Thr Tyr Gly Thr Tyr Thr Asp Leu Asp

1585 CCT GCA AAT GAT TCG GTC TAC GCC TAT ACA CGC AGC CTT GGG GCG GAA
    Pro Ala Asn Asp Ser Val Tyr Ala Tyr Thr Arg Ser Leu Gly Ala Glu

1633 AAA TAT CTT GTT GTT GTT AAC TTC AAG GAG CAA ATG ATG AGA TAT AAA
    Lys Tyr Leu Val Val Val Asn Phe Lys Glu Gln Met Met Arg Tyr Lys

1681 TTA CCG GAT AAT TTA TCC ATT GAG AAA GTG ATT ATA GAC AGC AAC AGC
    Leu Pro Asp Asn Leu Ser Ile Glu Lys Val Ile Ile Asp Ser Asn Ser

1729 AAA AAC GTG GTG AAA AAG AAT GAT TCA TTA CTC GAG CTA AAA CCA TGG
    Lys Asn Val Val Lys Lys Asn Asp Ser Leu Leu Glu Leu Lys Pro Trp

1777 CAG TCA GGG GTT TAT AAA ACT AAA TCA ATA AAT CTC ATA GTC ACG CCA
    Gln Ser Gly Val Tyr Lys Thr Lys Ser Ile Asn Leu Ile Val Thr Pro

1825 AAT AAT GTA AAT ATA TTG AAA CTA TTA AAA CCG GCA TTT TAT GCC GGT
    Asn Asn Val Asn Ile Leu Lys Leu Leu Lys Pro Ala Phe Tyr Ala Gly

1873 TTT TTT AGC GCA AAA TAG
    Phe Phe Ser Ala Lye ***

SEQ ID NO. 5

DESCRIPTION:  E. rhapontici isomerase

LENGTH: 1305 bases or 435 amino acids

*** S E Q U E N C E ***

1 ATG TCC TCT CAA GGA TTG AAA ACG GCT NTC GCT ATT TTT CTT GCA ACC
    Met Ser Ser Gln Gly Leu Lys Thr Ala  ?  Ala Ile Phe Leu Ala Thr

49 ACT TTT TCT GCC ACA TCC TAT CAG GCC TGC AGT GCC NNN CCA GAT ACC
    Thr Phe Ser Ala Thr Ser Tyr Gln Ala Cys Ser Ala  ?  Pro Asp Thr

97 GCC CCC TCA CTC ACC GTT CAG CAA TCA AAT GCC CTG CCC ACA TGG TGG
    Ala Pro Ser Leu Thr Val Gln Gln Ser Asn Ala Leu Pro Thr Trp Trp

145 AAG CAG GCT GTT TTT TAT CAG GTA TAT CCA CGC TCA TTT AAA GAT ACG
    Lys Gln Ala Val Phe Tyr Gln Val Tyr Pro Arg Ser Phe Lys Asp Thr

193 AAT GGG GAT GGC ATT GGG GAT TTA AAC GGT ATT ATT GAG AAT TTA GAC
    Asn Gly Asp Gly Ile Gly Asp Leu Asn Gly Ile Ile Glu Asn Leu Asp

241 TAT CTG AAG AAA CTG GGT ATT GAT GCG ATT TGG ATC AAT CCA CAT TAC
    Tyr Leu Lys Lys Leu Gly Ile Asp Ala Ile Trp Ile Asn Pro His Tyr

289 GAT TCG CCG AAT ACG GAT AAT GGT TAT GAC ATC CGG GAT TAC CGT AAG
    Asp Ser Pro Asn Thr Asp Asn Gly Tyr Asp Ile Arg Asp Tyr Arg Lys

337 ATA ATG AAA GAA TAC GGT ACG ATG GAA GAC TTT GAC CGT CTT ATT TCA
    Ile Met Lys Glu Tyr Gly Thr Met Glu Asp Phe Asp Arg Leu Ile Ser

385 GAA ATG AAG AAA CGC AAT ATG CGT TTG ATG ATT GAT ATT GTT ATC AAC
    Glu Met Lys Lys Arg Asn Met Arg Leu Met Ile Asp Ile Val Ile Asn

433 CAC ACC AGC GAT CAG CAT GCC TGG TTT GTT CAG AGC AAA TCG GGT AAG
    His Thr Ser Asp Gln His Ala Trp Phe Val Gln Ser Lys Ser Gly Lys
```

```
 481 AAC AAC CCC TAC AGG GAC TAT TAC TTC TGG CGT GAC GGT AAG GAT GGC
     Asn Asn Pro Tyr Arg Asp Tyr Tyr Phe Trp Arg Asp Gly Lys Asp Gly

529 CAT GCC CCC AAT AAC TAT CCC TCC TTC TTC GGT GGC TCA GCC TGG GAA
     His Ala Pro Asn Asn Tyr Pro Ser Phe Phe Gly Gly Ser Ala Trp Glu

577 AAA GAC GAT AAA TCA GGC CAG TAT TAC CTC CAT TAC TTT GCC AAA CAG
     Lys Asp Asp Lys Ser Gly Gln Tyr Tyr Leu His Tyr Phe Ala Lys Gln

625 CAA CCC GAC CTC AAC TGG GAC AAT CCC AAA GTC CGT CAA GAC CTG TAT
     Gln Pro Asp Leu Asn Trp Asp Asn Pro Lys Val Arg Gln Asp Leu Tyr

673 GAC ATG CTC CGC TTC TGG TTA GAT AAA GGC GTT TCT GGT TTA CGC TTT
     Asp Met Leu Arg Phe Trp Leu Asp Lys Gly Val Ser Gly Leu Arg Phe

721 GAT ACC GTT GCC ACC TAC TCG AAA ATC CCG AAC TTC CCT GAC CTT AGC
     Asp Thr Val Ala Thr Tyr Ser Lys Ile Pro Asn Phe Pro Asp Leu Ser

769 CAA CAG CAG TTA AAA AAT TTC GCC GAG GAA TAT ACT AAA GGT CCT AAA
     Gln Gln Gln Leu Lys Asn Phe Ala Glu Glu Tyr Thr Lys Gly Pro Lys

817 ATT CAC GAC TAC GTG AAT GAA ATG AAC AGA GAA GTA TTA TCC CAC TAT
     Ile His Asp Tyr Val Asn Glu Met Asn Arg Glu Val Leu Ser His Tyr

865 GAT ATC GCC ACT GCG GGG GAA ATA TTT GGG GTT CCT CTG GAT AAA TCG
     Asp Ile Ala Thr Ala Gly Glu Ile Phe Gly Val Pro Leu Asp Lys Ser

913 ATT AAG TTT TTC GAT CGC CGT AGA AAT GAA TTA AAT ATA GCG TTT ACG
     Ile Lys Phe Phe Asp Arg Arg Arg Asn Glu Leu Asn Ile Ala Phe Thr

961 TTT GAT CTG ATC AGG CTC GAT CGT GAT GCT GAT GAA AGA TGG CGG CGA
     Phe Asp Leu IXe Arg Leu Asp Arg Asp Ala Asp Glu Arg Trp Arg Arg

1009 AAA GAC TGG ACC CTT TCG CAG TTC CGA AAA ATT GTC GAT AAG GTT GAC
     Lys Asp Trp Thr Leu Ser Gln Phe Arg Lys Ile Val Asp Lys Val Asp

1057 CAA ACG GCA GGA GAG TAT GGG TGG AAT GCC TTT TTC TTA GAC AAT CAC
     Gln Thr Ala Gly Glu Tyr Gly Trp Asn Ala Phe Phe Leu Asp Asn His

1105 GAC AAT CCC CGC GCG GTT TCT CAC TTT GGT GAT GAT CGA CCA CAA TGG
     Asp Asn Pro Arg Ala Val Ser His Phe Gly Asp Asp Arg Pro Gln Trp

1153 CGC GAG CAT GCG GCG AAA GCA CTG GCA ACA TTG ACG CTG ACC CAG CGT
     Arg Glu His Ala Ala Lys Ala Leu Ala Thr Leu Thr Leu Thr Gln Arg

1201 GCA ACG CCG TTT ATC TAT CAG GGT TCA GAA CTC GGT ATG ACC AAT TAT
     Ala Thr Pro Phe Ile Tyr Gln Gly Ser Glu Leu Gly Met Thr Asn Tyr

1249 CCC TTT AAA AAA ATC GAT GAT TTC GAT GAT GTA GAG GTG AAA GGT TTT
     Pro Phe Lys Lys Ile Asp Asp Phe Asp Asp Val Glu Val Lys Gly Phe

1297 TGG CAA GAC
     Trp Gln Asp

SEQ ID NO. 6

NAME:     SZISO1.DNA      LENGTH:    471 bases or 157
                                          amino acids DESCRIPTION:   SZ62 isomerase

*  S E Q U E N C E  *

1 GTT TTT TAT CAG ATC TAT CCT CGC TCA TTT AAA GAC ACC AAT GAT GAT
     Val Phe Tyr Gln Ile Tyr Pro Arg Ser Phe Lys Asp Thr Asn Asp Asp

49 GGC ATT GGC GAT ATT CGC GGT ATT ATT GAA AAG CTG GAC TAT CTG AAA
     Gly Ile Gly Asp Ile Arg Gly Ile Ile Glu Lys Leu Asp Tyr Leu Lys

97 TCG CTC GGT ATT GAC GCT ATC TGG ATC AAT CCC CAT TAC GAC TCT CCG
     Ser Leu Gly Ile Asp Ala Ile Trp Ile Asn Pro His Tyr Asp Ser Pro

145 AAC ACC GAT AAC GGC TAT GAC ATC AGT AAT TAT CGT CAG ATA ATG AAA
     Asn Thr Asp Asn Gly Tyr Asp Ile Ser Asn Tyr Arg Gln Ile Met Lys

193 GAG TAT GGC ACA ATG GAG GAT TTT GAT AGC CTT GTT GCC GAA ATG AAA
     Glu Tyr Gly Thr Met Glu Asp Phe Asp Ser Leu Val Ala Glu Met Lys

241 AAA CGA AAT ATG CGC TTA ATG ATC GAC GTG GTC ATT AAC CAT ACC AGT
```

```
         Lys Arg Asn Met Arg Leu Met Ile Asp Val Val Ile Asn His Thr Ser

289  GAT CAA CAC CCG TGG TTT ATT CAG AGT AAA AGC GAT AAA AAC AAC CCT
     Asp Gln His Pro Trp Phe Ile Gln Ser Lys Ser Asp Lys Asn Asn Pro

337  TAT CGT GAC TAT TAT TTC TGG CGT GAC GGA AAA GAT AAT CAG CCA CCT
     Tyr Arg Asp Tyr Tyr Phe Trp Arg Asp Gly Lys Asp Asn Gln Pro Pro

385  AAT AAT TAC CCC TCA TTT TTC GGC GGC TCG GCA TGG CAA AAA GAT GCA
     Asn Asn Tyr Pro Ser Phe Phe Gly Gly Ser Ala Trp Gln Lys Asp Ala

433  AAG TCA GGA CAG TAC TAT TTA CAC TAT TTT GCC AGA CAG
     Lys Ser Gly Gln Tyr Tyr Leu His Tyr Phe Ala Arg Gln
```

SEQ ID NO. 7

NAME: PALA.SEQ          LENGTH:   1362 bases

DESCRIPTION: Palatinase

* S E Q U E N C E *

```
1     ATGGCTACAA AAATCGTTTT AGTGGGCGCA GGCAGCGCGC AATTCGGCTA CGGCACCCTG
61    GGCGATATCT TCCAGAGCAA GACGCTGTAC GGCAGTGAAA TTGTGCTGCA TGACATCAAC
121   CCAACCTCGC TGGCCGTGAC CGAGAAAACC GCCCGTGACT TCCTGGCTGC GGAAGATCTG
181   CCGTTTATCG TCAGCGCCAC CACCGATCGC AAAACCGCGC TGAGCGGAGC GGAGTTCGTG
241   ATTATCTCCA TTGAAGTGGG CGACCGCTTT GCCCTGTGGG ATCTCGACTG GCAGATCCCG
301   CAACAGTATG GCATTCAGCA GGTGTATGGT GAAAACGGTG CCCTGGCGG GCTGTTCCAC
361   TCGCTGCGCA TCATTCCACC GATCCTCGAC ATCTGCGCCG ACGTGGCGGA CATTTGCCCG
421   AACGCCTGGG TATTCAACTA CTCGAACCCG ATGAGCCGCA TTTGCACCAC CGTGCATCGC
481   CGTTTCCCGC AGCTCAACTT TGTCGGCATG TGCCATGAAA TCGCCTCACT TGAGCGTTAT
541   CTGCCAGAAA TGCTCGGCAC CTCCTTCGAC AATCTCACTC TGCGCGCTGC CGGGCTGAAC
601   CACTTCAGCG TGTTGCTGGA GGCCAGCTAT AAAGACAGCG AAAAGACGC TTACGCCGAC
661   GTACGCGCCA AGGCACCGGA CTATTTCTCC CGTCTGCCGG GCTACAGCGA TATTCTGGCT
721   TACACCCGCA TCACGGCAA ATTGGTGGAG ACAGAAGGCA GCACCGAACG CGATGCGCTG
781   GGCGGCAAAG ACAGCGCCTA TCCGTGGGCG GACCGCACGC TGTTCAAAGA GATCCTGGAG
841   AAGTTTCACC ATTTGCCGAT CACCGGCGAC AGCCACTTTG GCGAGTACAT CCGTTGGGCC
901   AGCGAAGTCA GCGATCACCG CGGTATCCTC GATTTCTACA CCTTCTACCG CAACTATCTG
961   GGGCATGTGC AGCCAAAAAT CGAACTGAAG CTGAAAGAAC GCGTGGTGCC GATCATGGAA
1021  GGGATCCTCA CCGATTCCGG TTATGAAGAG TCTGCGGTCA ACATTCCGAA CCAGGGATTT
1081  ATCAAGCAAC TGCCGGCGTT TATTGCCGTC GAAGTCCCGG CGATTATCGA CCGCAAGGGC
1141  GTGCACGGCA TCAAGGTCGA TATGCCTGCG GGCATCGGTG GCCTGTTGAG CAACCAGATT
1201  GCGATTCACG ATCTGACCGC CGACGCAGTG ATTGAAGGCT CGCGCGACCT GGTTATCCAG
1261  GCGCTGCTGG TGGACTCGGT CAACGATAAA TGCCGCGCGA TACCGGAACT GGTGGACGTG
1321  ATGATCTCAC GCCAGGGGCC GTGGCTCGAT TACCTGAAAT AA
```

SEQ ID NO. 8

NAME: PALA.SEQ          LENGTH:   1362 bases or 453
                                  amino acids DESCRIPTION: Palatinase

* S E Q U E N C E *

```
1     ATG GCT ACA AAA ATC GTT TTA GTG GGC GCA GGC AGC GCG CAA TTC GGC
      Met Ala Thr Lys Ile Val Leu Val Gly Ala Gly Ser Ala Gln Phe Gly
```

```
 49 TAC GGC ACC CTG GGC GAT ATC TTC CAG AGC AAG ACG CTG TAC GGC AGT
    Tyr Gly Thr Leu Gly Asp Ile Phe Gln Ser Lys Thr Leu Tyr Gly Ser

97 GAA ATT GTG CTG CAT GAC ATC AAC CCA ACC TCG CTG GCC GTG ACC GAG
    Glu Ile Val Leu His Asp Ile Asn Pro Thr Ser Leu Ala Val Thr Glu

145 AAA ACC GCC CGT GAC TTC CTG GCT GCG GAA GAT CTG CCG TTT ATC GTC
    Lys Thr Ala Arg Asp Phe Leu Ala Ala Glu Asp Leu Pro Phe Ile Val

193 AGC GCC ACC ACC GAT CGC AAA ACC GCG CTG AGC GGA GCG GAG TTC GTG
    Ser Ala Thr Thr Asp Arg Lys Thr Ala Leu Ser Gly Ala Glu Phe Val

241 ATT ATC TCC ATT GAA GTG GGC GAC CGC TTT GCC CTG TGG GAT CTC GAC
    Ile Ile Ser Ile Glu Val Gly Asp Arg Phe Ala Leu Trp Asp Leu Asp

289 TGG CAG ATC CCG CAA CAG TAT GGC ATT CAG CAG GTG TAT GGT GAA AAC
    Trp Gln Ile Pro Gln Gln Tyr Gly Ile Gln Gln Val Tyr Gly Glu Asn

337 GGT GGC CCT GGC GGG CTG TTC CAC TCG CTG CGC ATC ATT CCA CCG ATC
    Gly Gly Pro Gly Gly Leu Phe His Ser Leu Arg Ile Ile Pro Pro Ile

385 CTC GAC ATC TGC GCC GAC GTG GCG GAC ATT TGC CCG AAC GCC TGG GTA
    Leu Asp Ile Cys Ala Asp Val Ala Asp Ile Cys Pro Asn Ala Trp Val

433 TTC AAC TAC TCG AAC CCG ATG AGC CGC ATT TGC ACC ACC GTG CAT CGC
    Phe Asn Tyr Ser Asn Pro Met Ser Arg Ile Cys Thr Thr Val His Arg

481 CGT TTC CCG CAG CTC AAC TTT GTC GGC ATG TGC CAT GAA ATC GCC TCA
    Arg Phe Pro Gln Leu Asn Phe Val Gly Met Cys His Glu Ile Ala Ser

529 CTT GAC CGT TAT CTG CCA GAA ATG CTC GGC ACC TCC TTC GAC AAT CTC
    Leu Asp Arg Tyr Leu Pro Glu Met Leu Gly Thr Ser Phe Asp Asn Leu

577 ACT CTG CGC GCT GCC GGG CTG AAC CAC TTC AGC GTG TTG CTG GAG GCC
    Thr Leu Arg Ala Ala Gly Leu Asn His Phe Ser Val Leu Leu Glu Ala

625 AGC TAT AAA GAC AGC GGA AAA GAC GCT TAC GCC GAC GTA CGC GCC AAG
    Ser Tyr Lys Asp Ser Gly Lys Asp Ala Tyr Ala Asp Val Arg Ala Lys

673 GCA CCG GAC TAT TTC TCC CGT CTG CCG GGC TAC AGC GAT ATT CTG GCT
    Ala Pro Asp Tyr Phe Ser Arg Leu Pro Gly Tyr Ser Asp Ile Leu Ala

721 TAC ACC CGC AAT CAC GGC AAA TTG GTG GAG ACA GAA GGC AGC ACC GAA
    Tyr Thr Arg Asn His Gly Lys Leu Val Glu Thr Glu Gly Ser Thr Glu

769 CGC GAT GCG CTG GGC GGC AAA GAC AGC GCC TAT CCG TGG GCG GAC CGC
    Arg Asp Ala Leu Gly Gly Lys Asp Ser Ala Tyr Pro Trp Ala Asp Arg

817 ACG CTG TTC AAA GAG ATC CTG GAG AAG TTT CAC CAT TTG CCG ATC ACC
    Thr Leu Phe Lys Glu Ile Leu Glu Lys Phe His His Leu Pro Ile Thr

865 GGC GAC AGC CAC TTT GGC GAG TAC ATC CGT TGG GCC AGC GAA GTC AGC
    Gly Asp Ser His Phe Gly Glu Tyr Ile Arg Trp Ala Ser Glu Val Ser

913 GAT CAC CGC GGT ATC CTC GAT TTC TAC ACC TTC TAC CGC AAC TAT CTG
    Asp His Arg Gly Ile Leu Asp Phe Tyr Thr Phe Tyr Arg Asn Tyr Leu

961 GGG CAT GTG CAG CCA AAA ATC GAA CTG AAG CTG AAA GAA CGC GTG GTG
    Gly His Val Gln Pro Lys Ile Glu Leu Lys Leu Lys Glu Arg Val Val

1009 CCG ATC ATG GAA GGG ATC CTC ACC GAT TCC GGT TAT GAA GAG TCT GCG
     Pro Ile Met Glu Gly Ile Leu Thr Asp Ser Gly Tyr Glu Glu Ser Ala

1057 GTC AAC ATT CCG AAC CAG GGA TTT ATC AAG CAA CTG CCG GCG TTT ATT
     Val Asn Ile Pro Asn Gln Gly Phe Ile Lys Gln Leu Pro Ala Phe Ile

1105 GCC GTC GAA GTC CCG GCG ATT ATC GAC CGC AAG GGC GTG CAC GGC ATC
     Ala Val Glu Val Pro Ala Ile Ile Asp Arg Lys Gly Val His Gly Ile

1153 AAG GTC GAT ATG CCT GCG GGC ATC GGT GGC CTG TTG AGC AAC CAG ATT
     Lys Val Asp Met Pro Ala Gly Ile Gly Gly Leu Leu Ser Asn Gln Ile

1201 GCG ATT CAC GAT CTG ACC GCC GAC GCA GTG ATT GAA GGC TCG CGC GAC
     Ala Ile His Asp Leu Thr Ala Asp Ala Val Ile Glu Gly Ser Arg Asp

1249 CTG GTT ATC CAG GCG CTG CTG GTG GAC TCG GTC AAC GAT AAA TGC CGC
     Leu Val Ile Gln Ala Leu Leu Val Asp Ser Val Asn Asp Lys Cys Arg

1297 GCG ATA CCG GAA CTG GTG GAC GTG ATG ATC TCA CGC CAG GGG CCG TGG
```

-continued

```
      Ala Ile Pro Glu Leu Val Asp Val Met Ile Ser Arg Gln Gly Pro Trp
1345 CTC GAT TAC CTG AAA TAA
      Leu Asp Tyr Leu Lys ——
```

SEQ ID NO. 9

DESCRIPTION:   P. rubrum isomerase (variant)

LENGTH: 1803 base pairs

```
             ***  S E Q U E N C E  ***
   1 ATGCCCCGTC AAGGATTGAA AACTGCACTA GCGATTTTTC TAACCACATC ATTATGCATC

61 TCATGCCAGC AAGCCTTCGG TACGCAACAA CCCTTGCTTA ACGAAAAGAG TATCGAACAG

121 TCGAAAACCA TACCTAAATG GTGGAAGGAG GCTGTTTTTT ATCAGGTGTA TCCGCGCTCC

181 TTTAAAGACA CCAACGGAGA TGGCATCGGG GATATTAACG GCATCATAGA AAAATTAGAC

241 TATCTAAAAG CCTTGGGGAT TGATGCCATT TGGATCAACC CACATTATGA TTCTCCGAAC

301 ACGGATAATG GTTACGATAT ACGTGATTAT CGAAAAATCA TGAAAGAATA TGGCACGATG

361 GAGGATTTTG ACCGCCTGAT TTCTGAAATG AAAAAACGGA ATATGCGGTT GATGATTGAT

421 GTGGTCATCA ACCACACCAG CGATCAAAAC GAATGGTTTG TTAAAAGTAA AAGCAGTAAG

481 GATAATCCTT ATCGCGGCTA TTATTTCTGG AAAGATGCTA AGAAGGGCA GGCGCCTAAT

541 AATTACCCTT CATTCTTTGG TGGCTCGGCG TGGCAAAAAG ATGAAAAGAC CAATCAATAC

601 TACCTGCACT ATTTTGCTAA CAACAGCCT GACCTAAACT GGGATAATCC CAAAGTCCGT

661 CAAGATCTTT ATGCAATGTT ACGTTTCTGG TTAGATAAAG GCGTGTCTGG TTTACGTTTT

721 GATACGGTAG CGACCTACTC AAAAATTCCG GATTTCCCAA ATCTCACCCA CAACAGCTG

781 AAGAATTTTG CAGCGGAGTA TACCAAGGGC CCTAATATTC ATCGTTACGT CAATGAAATG

841 AATAAAGAGG TCTTGTCTCA TTACGACATT GCGACTGCCG GTGAAATCTT TGGCGTACCC

901 TTGGATCAAT CGATAAAGTT CTTCGATCGC CGCCGTGATG AGCTGAACAT TGCATTTACC

961 TTTGACTTAA TCAGACTCGA TCGAGACTCT GATCAAAGAT GGCGTCGAAA AGATTGGAAA

1021 TTGTCGCAAT TCCGGCAGAT CATCGATAAC GTTGACCGTA CTGCAGGAGA ATATGGTTGG

1081 AATGCCTTCT TCTTGGATAA CCACGACAAT CCGCGCGCTG TCTCGCACTT TGGCGATGAT

1141 CGCCCACAAT GGCGTGAGCC ATCGGCTAAA GCGCTTGCAA CCTTGACGCT GACTCAACGA

1201 GCAACACCTT TTATTTATCA AGGTTCAGAA TTGGGCATGA CCAATTACCC GTTTAAAGCT

1261 ATTGATGAAT TCGATGATAT TGAGGTGAAA GGTTTTTGGC ATGACTACGT TGAGACAGGA

1321 AAGGTCAAAG CCGACGAGTT CTTGCAAAAT GTACGCCTGA CGAGCAGGGA TAACAGCCGG

1381 ACGCCGTTCC AATGGGATGG GAGCAAAAAT GCAGGATTCA CGAGCGGAAA ACCTTGGTTC

1441 AAGGTCAACC CAAACTACCA GGAAATCAAT GCAGTAAGTC AAGTCACACA ACCCGACTCA

1501 GTATTTAACT ATTATCGTCA GTTGATCAAG ATAAGGCATG ACATCCCGGC ACTGACCTAT

1561 GGTACATACA CCGATTTGGA TCCTGCAAAT GATTCGGTCT ACGCCTATAC ACGCAGCCTT

1621 GGGGCGGAAA AATATCTTGT TGTTGTTAAC TTCAAGGAGC AAATGATGAG ATATAAATTA

1681 CCGGATAATT TATCCATTGA GAAAGTGATT ATAGACAGCA ACAGCAAAAA CGTGGTGAAA

1741 AAGAATGATT CATTACTCGA GCTAAAACCA TGGCAGTCAG GGGTTTATAA ACTAAATCAA

1801 TAA
```

SEQ ID NO. 10

DESCRIPTION: P. rubrum isomerase (variant)

LENGTH: 1803 bases or 600 amino acids

-continued

\*\*\* S E Q U E N C E \*\*\*

```
   1 ATG CCC CGT CAA GGA TTG AAA ACT GCA CTA GCG ATT TTT CTA ACC ACA
     Met Pro Arg Gln Gly Leu Lys Thr Ala Leu Ala Ile Phe Leu Thr Thr

49 TCA TTA TGC ATC TCA TGC CAG CAA GCC TTC GGT ACG CAA CAA CCC TTG
     Ser Leu Cys Ile Ser Cys Gln Gln Ala Phe Gly Thr Gln Gln Pro Leu

97 CTT AAC GAA AAG AGT ATC GAA CAG TCG AAA ACC ATA CCT AAA TGG TGG
     Leu Asn Glu Lys Ser Ile Glu Gln Ser Lys Thr Ile Pro Lys Trp Trp

145 AAG GAG GCT GTT TTT TAT CAG GTG TAT CCG CGC TCC TTT AAA GAC ACC
     Lys Glu Ala Val Phe Tyr Gln Val Tyr Pro Arg Ser Phe Lys Asp Thr

193 AAC GGA GAT GGC ATC GGG GAT ATT AAC GGC ATA ATA GAA AAA TTA GAC
     Asn Gly Asp Gly Ile Gly Asp Ile Asn Gly Ile Ile Glu Lys Leu Asp

241 TAT CTA AAA GCC TTG GGG ATT GAT GCC ATT TGG ATC AAC CCA CAT TAT
     Tyr Leu Lys Ala Leu Gly Ile Asp Ala Ile Trp Ile Asn Pro His Tyr

289 GAT TCT CCG AAC ACG GAT AAT GGT TAC GAT ATA CGT GAT TAT CGA AAA
     Asp Ser Pro Asn Thr Asp Asn Gly Tyr Asp Ile Arg Asp Tyr Arg Lys

337 ATC ATG AAA GAA TAT GGC ACG ATG GAG GAT TTT GAC CGC CTG ATT TCT
     Ile Met Lys Glu Tyr Gly Thr Met Glu Asp Phe Asp Arg Leu Ile Ser

385 GAA ATG AAA AAA CGG AAT ATG CGG TTG ATG ATT GAT GTG GTC ATC AAC
     Glu Met Lys Lys Arg Asn Met Arg Leu Met Ile Asp Val Val Ile Asn

433 CAC ACC AGC GAT CAA AAC GAA TGG TTT GTT AAA AGT AAA AGC AGT AAG
     His Thr Ser Asp Gln Asn Glu Trp Phe Val Lys Ser Lys Ser Ser Lys

481 GAT AAT CCT TAT CGC GGC TAT TAT TTC TGG AAA GAT GCT AAA GAA GGG
     Asp Asn Pro Tyr Arg Gly Tyr Tyr Phe Trp Lys Asp Ala Lys Glu Gly

529 CAG GCG CCT AAT AAT TAC CCT TCA TTC TTT GGT GGC TCG GCG TGG CAA
     Gln Ala Pro Asn Asn Tyr Pro Ser Phe Phe Gly Gly Ser Ala Trp Gln

577 AAA GAT GAA AAG ACC AAT CAA TAC TAC CTG CAC TAT TTT GCT AAA CAA
     Lys Asp Glu Lys Thr Asn Gln Tyr Tyr Leu His Tyr Phe Ala Lys Gln

625 CAG CCT GAC CTA AAC TGG GAT AAT CCC AAA GTC CGT CAA GAT CTT TAT
     Gln Pro Asp Leu Asn Trp Asp Asn Pro Lys Val Arg Gln Asp Leu Tyr

673 GCA ATG TTA CGT TTC TGG TTA GAT AAA GGC GTG TCT GGT TTA CGT TTT
     Ala Met Leu Arg Phe Trp Leu Asp Lys Gly Val Ser Gly Leu Arg Phe

721 GAT ACG GTA GCG ACC TAC TCA AAA ATT CCG GAT TTC CCA AAT CTC ACC
     Asp Thr Val Ala Thr Tyr Ser Lys Ile Pro Asp Phe Pro Asn Leu Thr

769 CAA CAA CAG CTG AAG AAT TTT GCA GCG GAG TAT ACC AAG GGC CCT AAT
     Gln Gln Gln Leu Lys Asn Phe Ala Ala Glu Tyr Thr Lys Gly Pro Asn

817 ATT CAT CGT TAC GTC AAT GAA ATG AAT AAA GAG GTC TTG TCT CAT TAC
     Ile His Arg Tyr Val Asn Glu Met Asn Lys Glu Val Leu Ser His Tyr

865 GAC ATT GCG ACT GCC GGT GAA ATC TTT GGC GTA CCC TTG GAT CAA TCG
     Asp Ile Ala Thr Ala Gly Glu Ile Phe Gly Val Pro Leu Asp Gln Ser

913 ATA AAG TTC TTC GAT CGC CGC CGT GAT GAG CTG AAC ATT GCA TTT ACC
     Ile Lys Phe Phe Asp Arg Arg Arg Asp Glu Leu Asn Ile Ala Phe Thr

961 TTT GAC TTA ATC AGA CTC GAT CGA GAC TCT GAT CAA AGA TGG CGT CGA
     Phe Asp Leu Ile Arg Leu Asp Arg Asp Ser Asp Gln Arg Trp Arg Arg

1009 AAA GAT TGG AAA TTG TCG CAA TTC CGG CAG ATC ATC GAT AAC GTT GAC
     Lys Asp Trp Lys Leu Ser Gln Phe Arg Gln Ile Ile Asp Asn Val Asp

1057 CGT ACT GCA GGA GAA TAT GGT TGG AAT GCC TTC TTC TTG GAT AAC CAC
     Arg Thr Ala Gly Glu Tyr Gly Trp Asn Ala Phe Phe Leu Asp Asn His

1105 GAC AAT CCG CGC GCT GTC TCC CAC TTT GGC GAT GAT CGC CCA CAA TGG
     Asp Asn Pro Arg Ala Val Ser His Phe Gly Asp Asp Arg Pro Gln Trp

1153 CGT GAG CCA TCG GCT AAA GCG CTT GCA ACC TTG ACG CTG ACT CAA CGA
     Arg Glu Pro Ser Ala Lys Ala Leu Ala Thr Leu Thr Leu Thr Gln Arg

1201 GCA ACA CCT TTT ATT TAT CAA GGT TCA GAA TTG GGC ATG ACC AAT TAC
     Ala Thr Pro Phe Ile Tyr Gln Gly Ser Glu Leu Gly Met Thr Asn Tyr
```

```
                                    -continued

1249 CCG TTT AAA GCT ATT GAT GAA TTC GAT GAT ATT GAG GTG AAA GGT TTT
     Pro Phe Lys Ala Ile Asp Glu Phe Asp Asp Ile Glu Val Lys Gly Phe

1297 TGG CAT GAC TAC GTT GAG ACA GGA AAG GTC AAA GCC GAC GAG TTC TTG
     Trp His Asp Tyr Val Glu Thr Gly Lys Val Lys Ala Asp Glu Phe Leu

1345 CAA AAT GTA CGC CTG ACG AGC AGG GAT AAC AGC CGG ACG CCG TTC CAA
     Gln Asn Val Arg Leu Thr Ser Arg Asp Asn Ser Arg Thr Pro Phe Gln

1393 TGG GAT GGG AGC AAA AAT GCA GGA TTC ACG AGC GGA AAA CCT TGG TTC
     Trp Asp Gly Ser Lys Asn Ala Gly Phe Thr Ser Gly Lys Pro Trp Phe

1441 AAG GTC AAC CCA AAC TAC CAG GAA ATC AAT GCA GTA AGT CAA GTC ACA
     Lys Val Asn Pro Asn Tyr Gln Glu Ile Asn Ala Val Ser Gln Val Thr

1489 CAA CCC GAC TCA GTA TTT AAC TAT TAT CGT CAG TTG ATC AAG ATA AGG
     Gln Pro Asp Ser Val Phe Asn Tyr Tyr Arg Gln Leu Ile Lys Ile Arg

1537 CAT GAC ATC CCG GCA CTG ACC TAT GGT ACA TAC ACC GAT TTG GAT CCT
     His Asp Ile Pro Ala Leu Thr Tyr Gly Thr Tyr Thr Asp Leu Asp Pro

1585 GCA AAT GAT TCG GTC TAC GCC TAT ACA CGC AGC CTT GGG GCG GAA AAA
     Ala Asn Asp Ser Val Tyr Ala Tyr Thr Arg Ser Leu Gly Ala Glu Lys

1633 TAT CTT GTT GTT GTT AAC TTC AAG GAG CAA ATG ATG AGA TAT AAA TTA
     Tyr Leu Val Val Val Asn Phe Lys Glu Gln Met Met Arg Tyr Lys Leu

1681 CCG GAT AAT TTA TCC ATT GAG AAA GTG ATT ATA GAC AGC AAC AGC AAA
     Pro Asp Asn Leu Ser Ile Glu Lys Val Ile Ile Asp Ser Asn Ser Lys

1729 AAC GTG GTG AAA AAG AAT GAT TCA TTA CTC GAG CTA AAA CCA TGG CAG
     Asn Val Val Lys Lys Asn Asp Ser Leu Leu Glu Leu Lys Pro Trp Gln

1777 TCA GGG GTT TAT AAA CTA AAT CAA TAA
     Ser Gly Val Tyr Lys Leu Asn Gln ---

SEQ ID NO. 11

DESCRIPTION:  SZ 62 isomerase

LENGTH: 1794 bases

***  S E Q U E N C E  ***

1 ATGTCTTTTG TTACGCTACG TACCGGGGTG GCTGTCGCGC TGTCATCTTT GATAATAAGT

61 CTGGCCTGCC CGGCTGTCAG TGCTGCACCA TCCTTGAATC AGGATATTCA CGTTCAAAAG

121 GAAAGTGAAT ATCCTGCATG GTGGAAAGAA GCTGTTTTTT ATCAGATCTA TCCTCGCTCA

181 TTTAAAGACA CCAATGATGA TGGCATTGGC GATATTCGCG GTATTATTGA AAAGCTGGAC

241 TATCTGAAAT CGCTCGGTAT TGACGCTATC TGGATCAATC CCATTACGA CTCTCCGAAC

301 ACCGATAACG GCTATGACAT CAGTAATTAT CGTCAGATAA TGAAAGAGTA TGGCACAATG

361 GAGGATTTTG ATAGCCTTGT TGCCGAAATG AAAAAACGAA ATATGCGCTT AATGATCGAC

421 GTGGTCATTA ACCATACCAG TGATCAACAC CCGTGGTTTA TTCAGAGTAA AAGCGATAAA

481 AACAACCCTT ATCGTGACTA TTATTTCTGG CGTGACGGAA AAGATAATCA GCCACCTAAT

541 AATTACCCCT CATTTTTCGG CGGCTCGGCA TGGCAAAAAG ATGCAAAGTC AGGACAGTAC

601 TATTTACACT ATTTTGCCAG ACAGCAACCT GATCTCAACT GGGATAACCC GAAAGTACGT

661 GAGGATCTTT ACGCAATGCT CCGCTTCTGG CTGGATAAAG GCGTTTCAGG CATGCGATTT

721 GATACGGTGG CAACTTATTC CAAAATCCCG GGATTTCCCA ATCTGACACC TGAACAACAG

781 AAAAATTTTG CTGAACAATA CACCATGGGD CCTAATATTC ATCGATACAT TCAGGAAATG

841 AACCGGAAAG TTCTGTCCCG GTATGATGTG GCCACCGCGG GTGAAATTTT TGGCGTCCCG

901 CTGGATCGTT CGTCGCAGTT TTTTGATCGC CGCCGACATG AGCTGAATAT GGCGTTTATG

961 TTTGACCTCA TTCGTCTCGA TCGCGACAGC AATGAACGCT GGCGTCACAA GTCGTGGTCG

1021 CTCTCTCAGT TCCGCCAGAT CATCAGCAAA ATGGATGTCA CGGTCGGAAA GTATGGCTGG
```

-continued

```
1081 AACACGTTCT TCTTAGACAA CCATGACAAC CCCCGTGCGG TATCTCACTT CGGGGATGAC

1141 AGGCCGCAAT GGCGGGAGGC GTCGGCTAAG GCACTGGCGA CGATTACCCT CACTCAGCGG

1201 GCGACGCCGT TTATTTATCA GGGTTCAGAG CTGGGAATGA CTAATTATCC CTTCAGGCAA

1261 CTCAACGAAT TTGACGACAT CGAGGTCAAA GGTTTCTGGC AGGATTATGT CCAGAGTGGA

1321 AAAGTCACGG CCACAGAGTT TCTCGATAAT GTGCGCCTGA CGAGCCGCGA TAACAGCAGA

1381 ACACCTTTCC AGTGGAATGA CACCCTGAAT GCTGGTTTTA CTCGCGGAAA GCCGTGGTTT

1441 CACATCAACC CAAACTATGT GGAGATCAAC SCCGAACGCG AAGAAACCCG CGAAGATTCA

1501 GTGCTGAATT ACTATAAAAA AATGATTCAG CTACGCCACC ATATCCCTGC TCTGGTATAT

1561 GGCGCCTATC AGGATCTTAA TCCACAGGAC AATACCGTTT ATGCCTATAC CCGAACGCTG

1621 GGTAACGAGC GTTATCTGGT CGTGGTGAAC TTTAAGGAGT ACCCGGTCCG CTATACTCTC

1681 CCGGCTAATG ATGCCATCGA GGAAGTGGTC ATTGATACTC AGCAGCAAGG TGCGCCGCAC

1741 AGCACATCCC TGTCATTGAG CCCCTGGCAG GCAGGTGCGT ATAAGCTGCG GTAA
```

SEQ ID NO. 12

DESCRIPTION: SZ 62 isomerase

LENGTH: 1794 bases or 597 amino acids.

* S E Q U E N C E *

```
  1 ATG TCT TTT GTT ACG CTA CGT ACC GGG GTG GCT GTC GCG CTG TCA TCT
    Met Ser Phe Val Thr Leu Arg Thr Gly Val Ala Val Ala Leu Ser Ser

49 TTG ATA ATA AGT CTG GCC TGC CCG GCT GTC AGT GCT GCA CCA TCC TTG
    Leu Ile Ile Ser Leu Ala Cys Pro Ala Val Ser Ala Ala Pro Ser Leu

97 AAT CAG GAT ATT CAC GTT CAA AAG GAA AGT GAA TAT CCT GCA TGG TGG
    Asn Gln Asp Ile His Val Gln Lys Glu Ser Glu Tyr Pro Ala Trp Trp

145 AAA GAA GCT GTT TTT TAT CAG ATC TAT CCT CGC TCA TTT AAA GAC ACC
    Lys Glu Ala Val Phe Tyr Gln Ile Tyr Pro Arg Ser Phe Lys Asp Thr

193 AAT GAT GAT GGC ATT GGC GAT ATT CGC GGT ATT ATT GAA AAG CTG GAC
    Asn Asp Asp Gly Ile Gly Asp Ile Arg Gly Ile Ile Glu Lys Leu Asp

241 TAT CTG AAA TCG CTC GGT ATT GAC GCT ATC TGG ATC AAT CCC CAT TAC
    Tyr Leu Lys Ser Leu Gly Ile Asp Ala Ile Trp Ile Asn Pro His Tyr

289 GAC TCT CCG AAC ACC GAT AAC GGC TAT GAC ATC AGT AAT TAT CGT CAG
    Asp Ser Pro Asn Thr Asp Asn Gly Tyr Asp Ile Ser Asn Tyr Arg Gln

337 ATA ATG AAA GAG TAT GGC ACA ATG GAG GAT TTT GAT AGC CTT GTT GCC
    Ile Met Lys Glu Tyr Gly Thr Met Glu Asp Phe Asp Ser Leu Val Ala

385 GAA ATG AAA AAA CGA AAT ATG CGC TTA ATG ATC GAC GTG GTC ATT AAC
    Glu Met Lys Lys Arg Asn Met Arg Leu Met Ile Asp Val Val Ile Asn

433 CAT ACC AGT GAT CAA CAC CCG TGG TTT ATT CAG AGT AAA AGC GAT AAA
    His Thr Ser Asp Gln His Pro Trp Phe Ile Gln Ser Lys Ser Asp Lys

481 AAC AAC CCT TAT CGT GAC TAT TAT TTC TGG CGT GAC GGA AAA GAT AAT
    Asn Asn Pro Tyr Arg Asp Tyr Tyr Phe Trp Arg Asp Gly Lys Asp Asn

529 CAG CCA CCT AAT AAT TAC CCC TCA TTT TTC GGC GGC TCG GCA TGG CAA
    Gln Pro Pro Asn Asn Tyr Pro Ser Phe Phe Gly Gly Ser Ala Trp Gln

577 AAA GAT GCA AAG TCA GGA CAG TAC TAT TTA CAC TAT TTT GCC AGA CAG
    Lys Asp Ala Lys Ser Gly Gln Tyr Tyr Leu His Tyr Phe Ala Arg Gln

625 CAA CCT GAT CTC AAC TGG GAT AAC CCG AAA GTA CGT GAG GAT CTT TAC
    Gln Pro Asp Leu Asn Trp Asp Asn Pro Lys Val Arg Glu Asp Leu Tyr

673 GCA ATG CTC CGC TTC TGG CTG GAT AAA GGC GTT TCA GGC ATG CGA TTT
    Ala Met Leu Arg Phe Trp Leu Asp Lys Gly Val Ser Gly Met Arg Phe

721 GAT ACG GTG GCA ACT TAT TCC AAA ATC CCG GGA TTT CCC AAT CTG ACA
    Asp Thr Val Ala Thr Tyr Ser Lys Ile Pro Gly Phe Pro Asn Leu Thr
```

```
 769 CCT GAA CAA CAG AAA AAT TTT GCT GAA CAA TAC ACC ATG GGD CCT AAT
     Pro Glu Gln Gln Lys Asn Phe Ala Glu Gln Tyr Thr Met  ?  Pro Asn

817 ATT CAT CGA TAC ATT CAG GAA ATG AAC CGG AAA GTT CTG TCC CGG TAT
     Ile His Arg Tyr Ile Gln Glu Met Asn Arg Lys Val Leu Ser Arg Tyr

865 GAT GTG GCC ACC GCG GGT GAA ATT TTT GGC GTC CCG CTG GAT CGT TCG
     Asp Val Ala Thr Ala Gly Glu Ile Phe Gly Val Pro Leu Asp Arg Ser

913 TCG CAG TTT TTT GAT CGC CGC CGA CAT GAG CTG AAT ATG GCG TTT ATG
     Ser Gln Phe Phe Asp Arg Arg Arg His Glu Leu Asn Met Ala Phe Met

961 TTT GAC CTC ATT CGT CTC GAT CGC GAC AGC AAT GAA CGC TGG CGT CAC
     Phe Asp Leu Ile Arg Leu Asp Arg Asp Ser Asn Glu Arg Trp Arg His

1009 AAG TCG TGG TCG CTC TCT CAG TTC CGC CAG ATC ATC AGC AAA ATG GAT
     Lys Ser Trp Ser Leu Ser Gln Phe Arg Gln Ile Ile Ser Lys Met Asp

1057 GTC ACG GTC GGA AAG TAT GGC TGG AAC ACG TTC TTC TTA GAC AAC CAT
     Val Thr Val Gly Lys Tyr Gly Trp Asn Thr Phe Phe Leu Asp Asn His

1105 GAC AAC CCC CGT GCG GTA TCT CAC TTC GGG GAT GAC AGG CCG CAA TGG
     Asp Asn Pro Arg Ala Val Ser His Phe Gly Asp Asp Arg Pro Gln Trp

1153 CGG GAG GCG TCG GCT AAG GCA CTG GCG ACG ATT ACC CTC ACT CAG CGG
     Arg Glu Ala Ser Ala Lys Ala Leu Ala Thr Ile Thr Leu Thr Gln Arg

1201 GCG ACG CCG TTT ATT TAT CAG GGT TCA GAG CTG GGA ATG ACT AAT TAT
     Ala Thr Pro Phe Ile Tyr Gln Gly Ser Glu Leu Gly Met Thr Asn Tyr

1249 CCC TTC AGG CAA CTC AAC GAA TTT GAC GAC ATC GAG GTC AAA GGT TTC
     Pro Phe Arg Gln Leu Asn Glu Phe Asp Asp Ile Glu Val Lys Gly Phe

1297 TGG CAG GAT TAT GTC CAG AGT GGA AAA GTC ACG GCC ACA GAG TTT CTC
     Trp Gln Asp Tyr Val Gln Ser Gly Lys Val Thr Ala Thr Glu Phe Leu

1345 GAT AAT GTG CGC CTG ACG AGC CGC GAT AAC AGC AGA ACA CCT TTC CAG
     Asp Asn Val Arg Leu Thr Ser Arg Asp Asn Ser Arg Thr Pro Phe Gln

1393 TGG AAT GAC ACC CTG AAT GCT GGT TTT ACT CGC GGA AAG CCG TGG TTT
     Trp Asn Asp Thr Leu Asn Ala Gly Phe Thr Arg Gly Lys Pro Trp Phe

1441 CAC ATC AAC CCA AAC TAT GTG GAG ATC AAC SCC GAA CGC GAA GAA ACC
     His Ile Asn PrQ Asn Tyr Val Glu Ile Asn  ?  Glu Arg Glu Glu Thr

1489 CGC GAA GAT TCA GTG CTG AAT TAC TAT AAA AAA ATG ATT CAG CTA CGC
     Arg Glu Asp Ser Val Leu Asn Tyr Tyr Lys Lys Met Ile Gln Leu Arg

1537 CAC CAT ATC CCT GCT CTG GTA TAT GGC GCC TAT CAG GAT CTT AAT CCA
     His His Ile Pro Ala Leu Val Tyr Gly Ala Tyr Gln Asp Leu Asn Pro

1585 CAG GAC AAT ACC GTT TAT GCC TAT ACC CGA ACG CTG GGT AAC GAG CGT
     Gln Asp Asn Thr Val Tyr Ala Tyr Thr Arg Thr Leu Gly Asn Glu Arg

1633 TAT CTG GTC GTG GTG AAC TTT AAG GAG TAC CCG GTC CGC TAT ACT CTC
     Tyr Leu Val Val Val Asn Phe Lys Glu Tyr Pro Val Arg Tyr Thr Leu

1681 CCG GCT AAT GAT GCC ATC GAG GAA GTG GTC ATT GAT ACT CAG CAG CAA
     Pro Ala Asn Asp Ala Ile Glu Glu Val Val Ile Asp Thr Gln Gln Gln

1729 GGT GCG CCG CAC AGC ACA TCC CTG TCA TTG AGC CCC TGG CAG GCA GGT
     Gly Ala Pro His Ser Thr Ser Leu Ser Leu Ser Pro Trp Gln Ala Gly

1777 GCG TAT AAG CTGCGG TAA
     Ala Tyr Lys Leu Arg ---
```

SEQ ID NO. 13

DESCRIPTION:  MX 45 isomerase

LENGTH: 1782 bases

* S E Q U E N C E *

```
  1 ATGCTTATGA AGAGATTATT CGCCGCGTCT CTGATGCTTG CTTTTTCAAG CGTCTCCTCT

61 GTGAGGGCTG AGGAGGCCGT AAAGCCGGGC GCGCCATGGT GGAAAAGTGC TGTCTTCTAT

121 CAGGTCTATC CGCGCTCGTT CAAGGATACC AACGGTGATG GGATCGGCGA TTTCAAAGGA
```

-continued

```
 181 CTGACGGAGA AGCTCGACTA TCTCAAGGGG CTCGGCATAG ACGCCATCTG GATCAATCCA
 241 CATTACGCGT CTCCCAACAC CGATAATGGC TACGATATCA GCGACTATCG AGAGGTCATG
 301 AAGGAATATG GGACGATGGA GGACTTCGAT CGTCTGATGG CTGAGTTGAA GAAGCGCGGC
 361 ATGCGGCTCA TGGTTGATGT CGTGATCAAC CATTCGAGTG ACCAACACGA ATGGTTCAAG
 421 AGCAGCCGGG CCTCCAAAGA CAATCCCTAC CGTGACTATT ATTTCTGGCG TGACGGCAAA
 481 GACGGTCACG AGCCAAACAA TTACCCTTCC TTCTTCGGCG GTTCGGCATG GGAGAAGGAC
 541 CCCGTAACCG GCAATATTA CCTGCATTAT TTCGGTCGTC AGCAGCCAGA TCTGAACTGG
 601 GACACGCCGA AGCTTCGCGA GGAACTCTAT GCGATGCTGC GGTTCTGGCT CGACAAGGGC
 661 GTATCAGGCA TGCGGTTCGA TACGGTGGCT ACCTACTCGA AGACACCGGG TTTCCCGGAT
 721 CTGACACCGG AGCAGATGAA GAACTTCGCG GAGGCCTATA CCCAGGGGCC GAACCTTCAT
 781 CGTTACCTGC AGGAAATGCA CGAGAAGGTC TTCGATCATT ATGACGCGGT CACGGCCGGC
 841 GAAATCTTCG GCGCTCCGCT CAATCAAGTG CCGCTGTTCA TCGACAGCCG GAGGAAAGAG
 901 CTGGATATGG CTTTCACCTT CGATCTGATC CGTTATGATC GCGCACTGGA TCGTTGGCAT
 961 ACCATTCCGC GTACCTTAGC GGACTTCCGT CAAACGATCG ATAAGGTCGA CGCCATCGCG
1021 GGCGAATATG GCTGGAACAC GTTCTTCCTC GGCAATCACG ACAATCCCCG TGCGGTATCG
1081 CATTTTGGTG ACGATCGGCC GCAATGGCGC GAAGCCTCGG CCAAGGCTCT GGCCACCGTC
1141 ACCTTGACCC AGCGAGGAAC GCCGTTCATC TTCCAAGGAG ATGAACTCGG AATGACCAAC
1201 TACCCCTTCA GACGCTGCA GGACTTTGAT GATATCNNNN NNNNNNNNN NNNNNNNNNN
1261 NNNNNNNNNN NNNNNNNNNN NNNNNNNNNN NNNNNNNNNN NNNNNNNNNN NNNNNNNNNN
1321 NNNNNNNNNN NTGTGGCGTT GACTAGCCGA GCAAACGCCC GCACGCCCTT TCAATGGGAT
1381 GACAGTGCTA ATGCGGGATT CACAACTGGC AAGCCTTGGC TAAAGGTCAA TCCAAACTAC
1441 ACTGAGATCA ACGCCGCGCG GGAAATTGGC GATCCTAAAT CGGTCTACAG CTTTTACCGC
1501 AACCTGATCT CAATCCGGCA TGAAACTCCC GCTCTTTCGA CCGGGAGCTA TCGCGACATC
1561 GATCCGAGTA ATGCCGATGT CTATGCCTAT ACGCGCAGCC AGGATGGCGA GACCTATCTG
1621 GTCGTAGTCA ACTTCAAGGC AGAGCCAAGG AGTTTCACGC TTCCGGACGG CATGCATATT
1681 GCCGAAACCC TGATTGAGAG CAGTTCGCCA GCAGCTCCGG CGGCGGGGGC TGCAAGCCTT
1741 GAGCTGCAGC CTTGGCAGTC CGGCATCTAC AAGGTGAAGT AA
```

SEQ ID NO. 14

DESCRIPTION: MX 45 isomerase

LENGTH: 1782 bases or 593 amino acids

* SEQUENCE *

```
  1 ATG CTT ATG AAG AGA TTA TTC GCC GCG TCT CTG ATG CTT GCT TTT TCA
    Met Leu Met Lys Arg Leu Phe Ala Ala Ser Leu Met Leu Ala Phe Ser

49 AGC GTC TCC TCT GTG AGG GCT GAG GAG GCC GTA AAG CCG GGC GCG CCA
    Ser Val Ser Ser Val Arg Ala Glu Glu Ala Val Lys Pro Gly Ala Pro

97 TGG TGG AAA AGT GCT GTC TTC TAT CAG GTC TAT CCG CGC TCG TTC AAG
    Trp Trp Lys Ser Ala Val Phe Tyr Gln Val Tyr Pro Arg Ser Phe Lys

145 GAT ACC AAC GGT GAT GGG ATC GGC GAT TTC AAA GGA CTG ACG GAG AAG
    Asp Thr Asn Gly Asp Gly Ile Gly Asp Phe Lys Gly Leu Thr Glu Lys

193 CTC GAC TAT CTC AAG GGG CTC GGC ATA GAC GCC ATC TGG ATC AAT CCA
    Leu Asp Tyr Leu Lys Gly Leu Gly Ile Asp Ala Ile lrp Ile Asn Pro 241 CAT TAC GCG TCT CCC AAC ACC GAT AAT GGC TAC GAT ATC AGC GAC TAT
    His Tyr Ala Ser Pro Asn Thr Asp Asn Gly Tyr Asp Ile Ser Asp Tyr
```

```
 289 CGA GAG GTC ATG AAG GAA TAT GGG ACG ATG GAG GAC TTC GAT CGT CTG
     Arg Glu Val Met Lys Glu Tyr Gly Thr Met Glu Asp Phe Asp Arg Leu

337 ATG GCT GAG TTG AAG AAG CGC GGC ATG CGG CTC ATG GTT GAT GTC GTG
     Met Ala Glu Leu Lys Lys Arg Gly Met Arg Leu Met Val Asp Val Val

385 ATC AAC CAT TCG AGT GAC CAA CAC GAA TGG TTC AAG AGC AGC CGG GCC
     Ile Asn His Ser Ser Asp Gln His Glu Trp Phe Lys Ser Ser Arg Ala

433 TCC AAA GAC AAT CCC TAC CGT GAC TAT TAT TTC TGG CGT GAC GGC AAA
     Ser Lys Asp Asn Pro Tyr Arg Asp Tyr Tyr Phe Trp Arg Asp Gly Lys

481 GAC GGT CAC GAG CCA AAC AAT TAC CCT TCC TTC TTC GGC GGT TCG GCA
     Asp Gly His Glu Pro Asn Asn Tyr Pro Ser Phe Phe Gly Gly Ser Ala

529 TGG GAG AAG GAC CCC GTA ACC GGG CAA TAT TAC CTG CAT TAT TTC GGT
     Trp Glu Lys Asp Pro Val Thr Gly Gln Tyr Tyr Leu His Tyr Phe Gly

577 CGT CAG CAG CCA GAT CTG AAC TGG GAC ACG CCG AAG CTT CGC GAG GAA
     Arg Gln Gln Pro Asp Leu Asn Trp Asp Thr Pro Lys Leu Arg Glu Glu

625 CTC TAT GCG ATG CTG CGG TTC TGG CTC GAC AAG GGC GTA TCA GGC ATG
     Leu Tyr Ala Met Leu Arg Phe Trp Leu Asp Lys Gly Val Ser Gly Met

673 CGG TTC GAT ACG GTG GCT ACC TAC TCG AAG ACA CCG GGT TTC CCG GAT
     Arg Phe Asp Thr Val Ala Thr Tyr Ser Lys Thr Pro Gly Phe Pro Asp

721 CTG ACA CCG GAG CAG ATG AAG AAC TTC GCG GAG GCC TAT ACC CAG GGG
     Leu Thr Pro Glu Gln Met Lys Asn Phe Ala Glu Ala Tyr Thr Gln Gly

769 CCG AAC CTT CAT CGT TAC CTG CAG GAA ATG CAC GAG AAG GTC TTC GAT
     Pro Asn Leu His Arg Tyr Leu Gln Glu Met His Glu Lys Val Phe Asp

817 CAT TAT GAC GCG GTC ACG GCC GGC GAA ATC TTC GGClGCT CCG CTC AAT
     His Tyr Asp Ala Val Thr Ala Gly Glu Ile Phe Gly Ala Pro Leu Asn

865 CAA GTG CCG CTG TTC ATC GAC AGC CGG AGG AAA GAG CTG GAT ATG GCT
     Gln Val Pro Leu Phe Ile Asp Ser Arg Arg Lys Glu Leu Asp Met Ala

913 TTC ACC TTC GAT CTG ATC CGT TAT GAT CGC GCA CTG GAT CGT TGG CAT
     Phe Thr Phe Asp Leu Ile Arg Tyr Asp Arg Ala Leu Asp Arg Trp His

961 ACC ATT CCG CGT ACC TTA GCG GAC TTC CGT CAA ACG ATC GAT AAG GTC
     Thr Ile Pro Arg Thr Leu Ala Asp Phe Arg Gln Thr Ile Asp Lys Val

1009 GAC GCC ATC GCG GGC GAA TAT GGC TGG AAC ACG TTC TTC CTC GGC AAT
     Asp Ala Ile Ala Gly Glu Tyr Gly Trp Asn Thr Phe Phe Leu Gly Asn

1057 CAC GAC AAT CCC CGT GCG GTA TCG CAT TTT GGT GAC GAT CGG CCG CAA
     His Asp Asn Pro Arg Ala Val Ser His Phe Gly Asp Asp Arg Pro Gln

1105 TGG CGC GAA GCC TCG GCC AAG GCT CTG GCC ACC GTC ACC TTG ACC CAG
     Trp Arg Glu Ala Ser Ala Lys Ala Leu Ala Thr Val Thr Leu Thr Gln

1153 CGA GGA ACG CCG TTC ATC TTC CAA GGA GAT GAA CTC GGA ATG ACC AAC
     Arg Gly Thr Pro Phe Ile Phe Gln Gly Asp Glu Leu Gly Met Thr Asn

1201 TAC CCC TTC AAG ACG CTG CAG GAC TTT GAT GAT ATC NNN NNN NNN NNN
     Tyr Pro Phe Lys Thr Leu Gln Asp Phe Asp Asp Ile  ?   ?   ?   ?

1249 NNN NNN NNN NNN NNN NNN NNN NNN NNN NNN NNN NNN NNN NNN NNN NNN
      ?   ?   ?   ?   ?   ?   ?   ?   ?   ?   ?   ?   ?   ?   ?   ?

1297 NNN NNN NNN NNN NNN NNN NNN NNN NNN NNN NNN NNT GTG GCG TTG ACT
      ?   ?   ?   ?   ?   ?   ?   ?   ?   ?   ?   ?  Val Ala Leu Thr

1345 AGC CGA GCA AAC GCC CGC ACG CCC TTT CAA TGG GAT GAC AGT GCT AAT
     Ser Arg Ala Asn Ala Arg Thr Pro Phe Gln Trp Asp Asp Ser Ala Asn

1393 GCG GGA TTC ACA ACT GGC AAG CCT TGG CTA AAG GTC AAT CCA AAC TAC
     Ala Gly Phe Thr Thr Gly Lys Pro Trp Leu Lys Val Asn Pro Asn Tyr

1441 ACT GAG ATC AAC GCC GCG CGG GAA ATT GGC GAT CCT AAA TCG GTC TAC
     Thr Glu Ile Asn Ala Ala Arg Glu Ile Gly Asp Pro Lys Ser Val Tyr

1489 AGC TTT TAC CGC AAC CTG ATC TCA ATC CGG CAT GAA ACT CCC GCT CTT
     Ser Phe Tyr Arg Asn Leu Ile Ser Ile ArglHis Glu Thr Pro Ala Leu 1537 TCG ACC GGG AGC TAT CGC GAC ATC GAT CCG AGT AAT GCC GAT GTC TAT
     Ser Thr Gly Ser Tyr Arg Asp Ile Asp Pro Ser Asn Ala Asp Val Tyr
```

```
1585 GCC TAT ACG CGC AGC CAG GAT GGC GAG ACC TAT CTG GTC GTA CTC AAC
    Ala Tyr Thr Arg Ser Gln Asp Gly Clu Thr Tyr Leu Val Val Val Asn

1633 TTC AAG GCA GAG CCA AGG AGT TTC ACG CTT CCG GAC GGC ATG CAT ATT
    Phe Lys Ala Glu Pro Arg Ser Phe Thr Leu Pro Asp Gly Met His Ile

1681 GCC GAA ACC CTG ATT GAG AGC AGT TCG CCA GCA GCT CCG GCG GCG GGG
    Ala Glu Thr Leu Ile Glu Ser Ser Ser Pro Ala Ala Pro Ala Ala Gly

1729 GCT GCA AGC CTT GAG CTG CAG CCT TGG CAG TCC GGC ATC TAC AAG GTG
    Ala Ala Ser Leu Glu Leu Gln Pro Trp Gln Ser Gly Ile Tyr Lys Val

1777 AAG TAA
    Lys ---
```

SEQ ID NO. 15

DESCRIPTION: MX 45 palatinose hydrolase

LENGTH: 1704 bases

* S E Q U E N C E *

```
   1 ATGACTGAAA AGTTATCCTT CGAGTCGACA ACAATCTCGC GTCGCTGGTG AAAGAGGCT

61 GTTGTCTATC AGGTGTATCC CCGCTCGTTC CAGGATTCGA ACGGGACGG CATCGGCGAC

121 CTTCCGGGCA TAACTGCGAG GCTAGATTAC ATCCTCGGTC TAGGCGTTAG TGTCATCTGG

181 CTCAGCCCCC ATTTCGACTC TCCGAATGCT GACAACGGCT ACGATATCCG TGACTATCGC

241 AAGGTGATGC GCGAATTCGG CACCATGGCG GATTTCGATC ACCTGCTGGC CGAGACGAAA

301 AAGCGCGGCA TGCGGCTGAT CATCGATCTC GTCGTCAACC ATACCAGCGA CGAGCATGTC

361 TGGTTTGCCG AAAGCCGGGC CTCGAAAAAC AGCCCGTACC GTGATTACTA CATCTGGCAT

421 CCCGGCCGGG ACGGCGCCGA GCCGAACGAC TGGCGCTCAT TTTTCTCGGG CTCGGCATGG

481 ACTTTCGACC AGCCAACCGG CGAATACTAC ATGCATCTTT TCGCCGATAA ACAGCCGGAT

541 ATCAACTGGG ACAATCCGGC TGTGCGCGCC GATGTCTATG ACATCATGCG CTTTTGGCTG

601 GACAAGGGCG TCGACGGATT CCGCATGGAT GTCATCCCCT TCATCTCCAA GCAAGACGGC

661 CTGCCCGACT ATCCTGACCA TCATCGCGGC GCGCCGCAGT TTTTCCACGG TTCGGGTCCC

721 CGCTTGCACG ACTATCTTCA GGAAATGAAC CGCGAGGTAT TGTCGCATTA CGATGTGATG

781 ACGGTTGGCG AGGCCTTCGG TGTGACGGCG GATGCGACGC CGCTTCTGGT CGACGAACGG

841 CGCCGCGAAC TGAACATGAT CTTCAATTTC GACGCCGTGC GCATCGGCCG TGGCGAGACC

901 TGGCACACTA AGCCTTGGGC CCTGCCGGAA CTTAAGGCGA TCTATGCCCG TCTGGACGCT

961 GCGACCGACC AGCACTGCTG GGGTACGGTC TTTCTCTCCA ACCACGACAA TCCTCGTCTC

1021 GTCTCCCGGT TCGGTGATGA TCATCCTGAC TGGCGGGTGG CGTCGGCCAA GCTTCTTGCC

1081 ACACTTCTCC TAACGCTGAA GGGCACGCCT TTCATCTACC AAGGCGATGA ATTGGGCATG

1141 ACCAACTATC TCGGCTCGG TCGAGGAGAC GACGATATCG AGGTGCGCAA CGCCTGGCAG

1201 GCTGAGGTCA TGACCGGTAA GGCGGATGCA GCCGAATTTC TCGGGGAGAT GCTGAAGATT

1261 TCCCGCGATC ATTCCCGCAC ACCGATGCAA TGGGACGCCA GTCTCGACGG TGGTTTCACT

1321 CGGGGTGAAA AGCCCTGGCT ATCGGTCAAT CCGAACTATC GGGCGATCAA TGCGGATGCG

1381 GCACTCGCCG ATCCCGATTC GATCTACCAT TATTACGCCG CACTCATCCG TTTCCGGCGC

1441 GAGACACCGG CGCTCATCTA CGGCGATTAT GACGACTTGG CGCCGGATCA TCCGCACCTC

1501 TTCGTCTATA CAAGAACATT GGGGTCCGAG CGCTATCTGG TCGCGCTTAA CTTCTCCGGC

1561 GATGCGCAGG CACTTGTTCT CCCGACAGAC CTGAGCGCCG CGTCACCTGT TATCGGGCGC

1621 GCCCCGCAAG TGGACCGCAT GCAGCATGAT GCTGCACGGA TCGAGCTGAT GGGTTGGGAA
```

1681 GCGCGGGTCT ACCACTGCGC ATGA

SEQ ID NO. 16

DESCRIPTION: MX 45 palatinose hydrolase

LENGTH: 1704 bases or 567 amino acids

* S E Q U E N C E *

```
   1 ATG ACT GAA AAG TTA TCC TTC GAG TCG ACA ACA ATC TCG CGT CGC TGG
     Met Thr Glu Lys Leu Ser Phe Glu Ser Thr Thr Ile Ser Arg Arg Trp

49 TGG AAA GAG GCT GTT GTC TAT CAG GTG TAT CCC CGC TCG TTC CAG GAT
     Trp Lys Glu Ala Val Val Tyr Gln Val Tyr Pro Arg Ser Phe Gln Asp

97 TCG AAC GGG GAC GGC ATC GGC GAC CTT CCG GGC ATA ACT GCG AGG CTA
     Ser Asn Gly Asp Gly Ile Gly Asp Leu Pro Gly Ile Thr Ala Arg Leu

145 GAT TAC ATC CTC GGT CTA GGC GTT AGT GTC ATC TGG CTC AGC CCC CAT
     Asp Tyr Ile Leu Gly Leu Gly Val Ser Val Ile Trp Leu Ser Pro His

193 TTC GAC TCT CCG AAT GCT GAC AAC GGC TAC GAT ATC CGT GAC TAT CGC
     Phe Asp Ser Pro Asn Ala Asp Asn Gly Tyr Asp Ile Arg Asp Tyr Arg

241 AAG GTG ATG CGC GAA TTC GGC ACC ATG GCG GAT TTC GAT CAC CTG CTG
     Lys Val Met Arg Glu Phe Gly Thr Met Ala Asp Phe Asp His Leu Leu

289 GCC GAG ACG AAA AAG CGC GGC ATG CGG CTG ATC ATC GAT CTC GTC GTC
     Ala Glu Thr Lys Lys Arg Gly Met Arg Leu Ile Ile Asp Leu Val Val

337 AAC CAT ACC AGC GAC GAG CAT GTC TGG TTT GCC GAA AGC CGG GCC TCG
     Asn His Thr Ser Asp Glu His Val Trp Phe Ala Glu Ser Arg Ala Ser

385 AAA AAC AGC CCG TAC CGT GAT TAC TAC ATC TGG CAT CCC GGC CGG GAC
     Lys Asn Ser Pro Tyr Arg Asp Tyr Tyr Ile Trp His Pro Gly Arg Asp

433 GGC GCC GAG CCG AAC GAC TGG CGC TCA TTT TTC TCG GGC TCG GCA TGG
     Gly Ala Glu Pro Asn Asp Trp Arg Ser Phe Phe Ser Gly Ser Ala Trp

481 ACT TTC GAC CAG CCA ACC GGC GAA TAC TAC ATG CAT CTT TTC GCC GAT
     Thr Phe Alp Gln Pro Thr Gly Glu Tyr Tyr Met His Leu Phe Ala Asp

529 AAA CAG CCG GAT ATC AAC TGG GAC AAT CCG GCT GTG CGC GCC GAT GTC
     Lys Gln Pro Asp Ile Asn Trp Asp Asn Pro Ala Val Arg Ala Asp Val

577 TAT GAC ATC ATG CGC TTT TGG CTG GAC AAG GGC GTC GAC GGA TTC CGC
     Tyr Asp Ile Met Arg Phe lrp Leu Asp Lys Gly Val Asp Gly Phe Arg 625 ATG GAT GTC ATC CCC TTC ATC TCC AAG CAA GAC GGC CTG CCC GAC TAT
     Met Asp Val Ile Pro Phe Ile Ser Lys Gln Asp Gly Leu Pro Asp Tyr 673 CCT GAC CAT CAT CGC GGC GCG CCG CAG TTT TTC CAC GGT TCG GGT CCC
     Pro Asp His His Arg Gly Ala Pro Gln Phe Phe His Gly Ser Gly Pro 721 CGC TTG CAC GAC TAT CTT CAG GAA ATG AAC CGC GAG GTA TTG TCG CAT
     Arg Leu His Asp Tyr Leu Gln Glu Met Asn Arg Glu Val Leu Ser His 769 TAC GAT GTG ATG ACG GTT GGC GAG GCC TTC GGT GTG ACG GCG GAT GCG
     Tyr Asp Val Met Thr Val Gly Glu Ala Phe Gly Val Thr Ala Asp Ala 817 ACG CCG CTT CTG GTC GAC GAA CGG CGC CGC GAA CTG AAC ATG ATC TTC
     Thr Pro Leu Leu Val Asp Glu Arg Arg Arg Glu Leu Asn Met Ile Phe 865 AAT TTC GAC GCC GTG CGC ATC GGC CGT GGC GAG ACC TGG CAC ACT AAG
     Asn Phe Asp Ala Val Arg Ile Gly Arg Gly Glu Thr Trp His Thr Lys 913 CCT TGG GCC CTG CCG GAA CTT AAG GCG ATC TAT GCC CGT CTG GAC GCT
     Pro Trp Ala Leu Pro Glu Leu Lys Ala Ile Tyr Ala Arg Leu Asp Ala 961 GCG ACC GAC CAG CAC TGC TGG GGT ACG GTC TTT CTC TCC AAC CAC GAC
     Ala Thr Asp Gln His Cys Trp Gly Thr Val Phe Leu Ser Asn His Asp 1009 AAT CCT CGT CTC GTC TCC CGG TTC GGT GAT GAT CAT CCT GAC TGG CGG
     Asn Pro Arg Leu Val Ser Arg Phe Gly Asp Asp His Pro Asp Trp Arg 1057 GTG GCG TCG GCC AAG GTT CTT GCC ACA CTT CTC CTA ACG CTG AAG GGC
     Val Ala Ser Ala Lys Val Leu Ala Thr Leu Leu Leu Thr Leu Lys Gly

1105 ACG CCT TTC ATC TAC CAA GGC GAT GAA TTG GGC ATG ACC AAC TAT CCT
```

-continued

```
         Thr Pro Phe Ile Tyr Gln Gly Asp Glu Leu Gly Met Thr Asn Tyr Pro

1153 CGG CTC GGT CGA GGA GAC GAC GAT ATC GAG GTG CGC AAC GCC TGG CAG
     Arg Leu Gly Arg Gly Asp Asp Asp Ile Glu Val Arg Asn Ala Trp Gln

1201 GCT GAG GTC ATG ACC GGT AAG GCG GAT GCA GCC GAA TTT CTC GGG GAG
     Ala Glu Val Met Thr Gly Lys Ala Asp Ala Ala Glu Phe Leu Gly Glu

1249 ATG CTG AAG ATT TCC CGC GAT CAT TCC CGC ACA CCG ATG CAA TGG GAC
     Met Leu Lys Ile Ser Arg Asp His Ser Arg Thr Pro Met Gln Trp Asp

1297 GCC AGT CTC GAC GGT GGT TTC ACT CGG GGT GAA AAG CCC TGG CTA TCG
     Ala Ser Leu Asp Gly Gly Phe Thr Arg Gly Glu Lys Pro Trp Leu Ser

1345 GTC AAT CCG AAC TAT CGG GCG ATC AAT GCG GAT GCG GCA CTC GCC GAT
     Val Asn Pro Asn Tyr Arg Ala Ile Asn Ala Asp Ala Ala Leu Ala Asp

1393 CCC GAT TCG ATC TAC CAT TAT TAC GCC GCA CTC ATC CGT TTC CGG CGC
     Pro Asp Ser Ile Tyr His Tyr Tyr Ala Ala Leu Ile Arg Phe Arg Arg

1441 GAG ACA CCG GCG CTC ATC TAC GGC GAT TAT GAC GAC TTG GCG CCG GAT
     Glu Thr Pro Ala Leu Ile Tyr Gly Asp Tyr Asp Asp Leu Ala Pro Asp

1489 CAT CCG CAC CTC TTC GTC TAT ACA AGA ACA TTG GGG TCC GAG CGC TAT
     His Pro His Leu Phe Val Tyr Thr Arg Thr Leu Gly Ser Glu Arg Tyr

1537 CTG GTC GCG CTT AAC TTC TCC GGC GAT GCG CAG GCA CTT GTT CTC CCG
     Leu Val Ala Leu Asn Phe Ser Gly Asp Ala Gln Ala Leu Val Leu Pro

1585 ACA GAC CTG AGC GCC GCG TCA CCT GTT ATC GGG CGC GCC CCG CAA GTG
     Thr Asp Leu Ser Ala Ala Ser Pro Val Ile Gly Arg Ala Pro Gln Val

1633 GAC CGC ATG CAG CAT GAT GCT GCA CGG ATC GAG CTG ATG GGT TGG GAA
     Asp Arg Met Gln His Asp Ala Ala Arg Ile Glu Leu Met Gly Trp Glu

1681 GCG CGG GTC TAC CAC TGC GCA TGA
     Ala Arg Val Tyr His Cys Ala ---
```

---

We claim:

1. A process for the production of non-cariogenic sugars comprising:
   (a) contacting an isolated sucrose isomerase protein with sucrose in a suitable medium under conditions such that the sucrose is partly converted to a non-cariogenic sugar by the isolated sucrose-isomerase protein, wherein the protein is encoded by a DNA sequence comprising
      (i) a nucleotide sequence selected from the group consisting of SEQ ID NO:1, SEQ ID NO:2, SEQ ID NO:3, SEQ ID NO:9, SEQ ID NO:11, and any of these sequences without the signal peptide-coding region;
      (ii) a nucleotide sequence corresponding to the sequences from (i) within the scope of the degeneracy of the genetic code, or
      (iii) a nucleotide sequence that hybridizes with a sequence from (i), (ii), or both (i) and (ii); wherein a positive hybridization signal is still observed after washing with 1×SSC and 0.1% SDS at 55° C. for one hour; and
   (b) isolating the non-cariogenic sugar from the medium.

2. A process for the production of non-cariogenic sugars comprising:
   (a) contacting a cell having a reduced palatinose and/or trehalulose metabolism with sucrose in a suitable medium under conditions such that the sucrose is partly converted to a noncariogenic sugar, wherein the reduced palatinose and/or trehalulose metabolism is defined as the cell producing less than 2.5% of glucose plus fructose based on the total of acariogenic disaccharides and monosaccharide degradation products at a temperature of 15 to 65° C., and wherein said cell is transformed with a DNA sequence comprising
      (i) a nucleotide sequence selected from the group consisting of SEQ ID NO:1, SEQ ID NO:2, SEQ ID NO:3, SEQ ID NO:9, SEQ ID NO:11, and any of these sequences without the signal peptide-coding region;
      (ii) a nucleotide sequence corresponding to the sequences from (i) within the scope of the degeneracy of the genetic code, or
      (iii) a nucleotide sequence that hybridizes with a sequence from (i), (ii), or both (i) and (ii); wherein a positive hybridization signal is still observed after washing with 1×SSC and 0.1% at 55° C., for one hour; and
   (b) isolating the non-cariogenic sugar from the cell.

3. The process as claimed in claim 1 wherein step (a) comprises the contacting of the isolated sucrose isomerase protein with sucrose in a suitable medium under conditions such that the sucrose is partly converted to a non-cariogenic sugar, wherein the isolated sucrose isomerase protein is obtained from an extract of a cell, and wherein said cell is transformed with a DNA sequence comprising
   (i) a nucleotide sequence selected from the group consisting of SEQ ID NO:1, SEQ ID NO:2, SEQ ID NO:3, SEQ ID NO:9, SEQ ID NO:11, and any of these sequences without the signal peptide coding region;
   (ii) a nucleotide sequence corresponding to the sequences from (i) within the scope of the degeneracy of the genetic code, or
   (iii) a nucleotide sequence that hybridizes with a sequence from (i), (ii) or both (i) and (ii); wherein a positive hybridization signal is still observed after washing with 1×SSC and 0.1% SDS at 55° C. for one hour.

4. Process as claimed in claims 1, 2, or 3 wherein the non-cariogenic sugars are trehalulose or palatinose.

5. Process as claimed in claims 1, 2, or 3, wherein the organism, the extract, or the protein is used in an immobilized form, and wherein the process is characterized as having reduced palatinose and/or trehalulose metabolism, defined as producing less than 2.5% of glucose plus fructose based on the total of acariogenic disaccharides and monosaccharide degradation products at a temperature of 15 to 65° C.

* * * * *